US008899987B2

(12) United States Patent
Edwards et al.

(10) Patent No.: US 8,899,987 B2
(45) Date of Patent: *Dec. 2, 2014

(54) SIMULATED MEDICAMENT DELIVERY DEVICE HAVING AN ELECTRONIC CIRCUIT SYSTEM

(71) Applicant: kaleo, Inc., Richmond, VA (US)

(72) Inventors: Eric Shawn Edwards, Moseley, VA (US); Evan Thomas Edwards, Charlottesville, VA (US); Mark J. Licata, Doswell, VA (US); Paul F. Meyers, Fishers, IN (US); T. Spencer Williamson, Richmond, VA (US); Kai R. Worrell, Hopkins, MN (US); David A. Weinzierl, Andover, MN (US)

(73) Assignee: kaleo, Inc., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/962,336

(22) Filed: Aug. 8, 2013

(65) Prior Publication Data

US 2013/0323699 A1 Dec. 5, 2013

Related U.S. Application Data

(63) Continuation of application No. 13/550,893, filed on Jul. 17, 2012, which is a continuation of application No. 12/119,016, filed on May 12, 2008, now Pat. No. (Continued)

(51) Int. Cl.
| | |
|---|---|
| *G09B 23/28* | (2006.01) |
| *A61M 5/20* | (2006.01) |
| *G06F 19/00* | (2011.01) |
| *A61M 5/31* | (2006.01) |
| *A61M 5/32* | (2006.01) |
| *A61M 5/24* | (2006.01) |

(52) U.S. Cl.
CPC ............... *A61M 5/31* (2013.01); *A61M 5/3287* (2013.01); *A61M 5/2053* (2013.01); *A61M 5/24* (2013.01); *A61M 2205/50* (2013.01); *G06F 19/3468* (2013.01); *A61M 2205/581* (2013.01); *A61M 2005/2073* (2013.01); *G09B 23/28* (2013.01); *A61M 2205/583* (2013.01)
USPC ........................................................ 434/262

(58) Field of Classification Search
USPC ........................................................ 434/262
See application file for complete search history.

(56) References Cited

U.S. PATENT DOCUMENTS

| | | | |
|---|---|---|---|
| 2,277,907 A | 3/1942 | Goodale, Jr. et al. | |
| 2,960,087 A | 11/1960 | Uytenbogaart | |

(Continued)

FOREIGN PATENT DOCUMENTS

| | | |
|---|---|---|
| EP | 1043037 A2 | 10/2000 |
| EP | 1113700 A2 | 7/2001 |

(Continued)

OTHER PUBLICATIONS

"Solutions for Medical Devices," 3M Brochure, © 3M 2006 80-6201-3490-0.

(Continued)

*Primary Examiner* — Robert J Utama
*Assistant Examiner* — Sadaruz Zaman
(74) *Attorney, Agent, or Firm* — Cooley LLP

(57) ABSTRACT

Medicament delivery devices and simulated medicament delivery devices are described herein. An apparatus includes a simulated medicament injector. The simulated medicament injector includes a battery isolation member and an electronic circuit system having a processor. The battery isolation member is configured to selectively decouple a battery from the processor.

28 Claims, 46 Drawing Sheets

Related U.S. Application Data 8,231,573, which is a continuation-in-part of application No. 11/679,331, filed on Feb. 27, 2007, which is a continuation-in-part of application No. 11/671,025, filed on Feb. 5, 2007, now Pat. No. 8,172,082, which is a continuation-in-part of application No. 11/621,236, filed on Jan. 9, 2007, now Pat. No. 7,731,686, which is a continuation-in-part of application No. 10/572,148, filed as application No. PCT/US2006/003415 on Feb. 1, 2006, now Pat. No. 7,749,194.

(60) Provisional application No. 60/648,822, filed on Feb. 1, 2005, provisional application No. 60/731,886, filed on Oct. 31, 2005, provisional application No. 60/787,046, filed on Mar. 29, 2006.

(56) References Cited

U.S. PATENT DOCUMENTS

| | | |
|---|---|---|
| 3,055,362 A | 9/1962 | Uytenbogaart |
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,108,177 A | 8/1978 | Pistor |
| 4,149,394 A | 4/1979 | Sornes |
| 4,258,713 A | 3/1981 | Wardlaw |
| 4,360,019 A | 11/1982 | Portner et al. |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A * | 2/1987 | Dalling et al. ............... 434/262 |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,865,582 A | 9/1989 | Sibalis |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,394,866 A | 3/1995 | Ritson et al. |
| 5,399,163 A | 3/1995 | Peterson et al. |
| 5,417,660 A | 5/1995 | Martin |
| 5,466,217 A | 11/1995 | Myers et al. |
| 5,505,192 A | 4/1996 | Samiotes et al. |
| 5,514,135 A | 5/1996 | Earle |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,610,992 A | 3/1997 | Hickman |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,692,492 A * | 12/1997 | Bruna et al. ............. 128/200.23 |
| 5,695,476 A | 12/1997 | Harris |
| 5,697,916 A | 12/1997 | Schraga |
| 5,716,338 A | 2/1998 | Hjertman et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A * | 9/1998 | Wever et al. .................. 361/760 |
| 5,809,997 A | 9/1998 | Wolf |
| 5,813,397 A | 9/1998 | Goodman et al. |
| 5,814,020 A | 9/1998 | Gross |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,002,781 A | 12/1999 | Takayama et al. |
| 6,015,438 A | 1/2000 | Shaw |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,144,310 A | 11/2000 | Morris |
| 6,149,626 A | 11/2000 | Bachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |

(56) References Cited

U.S. PATENT DOCUMENTS

| | | |
|---|---|---|
| 6,192,891 B1 | 2/2001 | Gravel et al. |
| 6,193,695 B1 | 2/2001 | Rippstein, Jr. |
| 6,202,642 B1* | 3/2001 | McKinnon et al. ...... 128/200.23 |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,285,757 B1 | 9/2001 | Carroll et al. |
| 6,312,412 B1 | 11/2001 | Saied et al. |
| 6,317,630 B1 | 11/2001 | Gross et al. |
| 6,321,070 B1 | 11/2001 | Clark et al. |
| 6,321,654 B1 | 11/2001 | Robinson |
| 6,323,780 B1 | 11/2001 | Morris |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |
| 6,411,567 B1 | 6/2002 | Niemiec et al. |
| 6,413,236 B1 | 7/2002 | Van Dyke |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,478,771 B1 | 11/2002 | Lavi et al. |
| 6,482,185 B1 | 11/2002 | Hartmann |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,597,794 B2 | 7/2003 | Cole et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,659,980 B2 | 12/2003 | Moberg et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,945,961 B2 | 9/2005 | Miller et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,963,280 B2 | 11/2005 | Eskildsen |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,093,595 B2 | 8/2006 | Nesbitt |
| 7,113,101 B2 | 9/2006 | Petersen et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |
| 7,343,914 B2 | 3/2008 | Abrams et al. |
| 7,351,223 B2 | 4/2008 | Call |
| 7,416,540 B2 | 8/2008 | Edwards et al. |
| 7,544,188 B2 | 6/2009 | Edwards et al. |
| 7,648,482 B2 | 1/2010 | Edwards et al. |
| 7,648,483 B2 | 1/2010 | Edwards et al. |
| 7,682,155 B2 | 3/2010 | Raven et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,871,393 B2 | 1/2011 | Monroe |
| 7,938,802 B2 | 5/2011 | Bicknell et al. |
| 7,947,017 B2 | 5/2011 | Edwards et al. |
| 8,021,344 B2 | 9/2011 | Edwards et al. |
| 8,123,719 B2 | 2/2012 | Edwards et al. |
| 8,149,111 B2 | 4/2012 | Monroe |
| 8,172,082 B2 | 5/2012 | Edwards et al. |
| 8,212,658 B2 | 7/2012 | Monroe |
| 8,231,573 B2 | 7/2012 | Edwards et al. |
| 8,424,517 B2 | 4/2013 | Sutherland et al. |
| 8,556,865 B2 | 10/2013 | Krulevitch et al. |
| 8,556,867 B2 | 10/2013 | Krulevitch et al. |
| 2001/0005781 A1 | 6/2001 | Bergens et al. |
| 2002/0016567 A1* | 2/2002 | Hochman et al. ............ 604/131 |
| 2002/0072784 A1 | 6/2002 | Sheppard, Jr. et al. |
| 2002/0074345 A1* | 6/2002 | Schneider et al. ............ 222/94 |
| 2002/0076679 A1 | 6/2002 | Aman |
| 2002/0090601 A1 | 7/2002 | Strupat et al. |
| 2002/0096543 A1 | 7/2002 | Juselius |

(56) References Cited

U.S. PATENT DOCUMENTS

| | | |
|---|---|---|
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0106824 A1 | 6/2003 | Wilmot et al. |
| 2003/0120212 A1 | 6/2003 | Dedig et al. |
| 2003/0130853 A1 | 7/2003 | Maire |
| 2003/0233070 A1 | 12/2003 | De La Serna et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0069667 A1 | 4/2004 | Tomellini et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1* | 10/2004 | Atterbury et al. ............. 604/224 |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1* | 4/2005 | Baba et al. ................. 604/209 |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1* | 8/2005 | Mahoney ................. 340/539.12 |
| 2005/0171477 A1 | 8/2005 | Rubin et al. |
| 2005/0182358 A1 | 8/2005 | Veit et al. |
| 2005/0186221 A1 | 8/2005 | Reynolds et al. |
| 2005/0190941 A1 | 9/2005 | Yang |
| 2005/0197654 A1 | 9/2005 | Edman et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0111175 A1 | 5/2007 | Raven et al. |
| 2007/0149954 A1 | 6/2007 | Hood et al. |
| 2007/0184847 A1 | 8/2007 | Hansen et al. |
| 2007/0203247 A1 | 8/2007 | Phillips et al. |
| 2007/0210147 A1 | 9/2007 | Morrone et al. |
| 2007/0213598 A1* | 9/2007 | Howard et al. ............... 600/300 |
| 2007/0233001 A1* | 10/2007 | Burroughs et al. ........... 604/131 |
| 2007/0239116 A1 | 10/2007 | Follman et al. |
| 2007/0239140 A1 | 10/2007 | Chechelski et al. |
| 2007/0260210 A1 | 11/2007 | Conroy |
| 2008/0059133 A1 | 3/2008 | Edwards et al. |
| 2008/0111685 A1 | 5/2008 | Olson et al. |
| 2008/0160492 A1 | 7/2008 | Campbell et al. |
| 2008/0230057 A1 | 9/2008 | Sutherland |
| 2009/0024112 A1 | 1/2009 | Edwards et al. |
| 2009/0143761 A1 | 6/2009 | Cantor et al. |
| 2009/0194104 A1 | 8/2009 | Van Sickle |
| 2010/0160894 A1 | 6/2010 | Julian et al. |
| 2010/0192948 A1 | 8/2010 | Sutherland et al. |
| 2010/0211005 A1 | 8/2010 | Edwards et al. |
| 2010/0250280 A1 | 9/2010 | Sutherland |
| 2011/0144574 A1 | 6/2011 | Kamen et al. |
| 2012/0008811 A1 | 1/2012 | Edwards et al. |
| 2012/0015335 A1 | 1/2012 | Smith et al. |
| 2012/0046613 A1 | 2/2012 | Plumptre |
| 2012/0071819 A1 | 3/2012 | Bruggemann et al. |
| 2012/0101444 A1 | 4/2012 | Muller-Pathle et al. |
| 2012/0107783 A1 | 5/2012 | Julian et al. |
| 2012/0165747 A1 | 6/2012 | Lanin et al. |
| 2012/0226226 A1 | 9/2012 | Edwards et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2013/0023822 A1 | 1/2013 | Edwards et al. |
| 2013/0023825 A1 | 1/2013 | Edwards et al. |
| 2013/0079718 A1 | 3/2013 | Shang et al. |
| 2013/0079725 A1 | 3/2013 | Shang |
| 2013/0110050 A1 | 5/2013 | Boyd et al. |
| 2013/0184649 A1 | 7/2013 | Edwards et al. |
| 2013/0190692 A1 | 7/2013 | Edwards et al. |
| 2013/0266919 A1 | 10/2013 | Baker et al. |
| 2013/0280687 A1 | 10/2013 | Edwards et al. |

FOREIGN PATENT DOCUMENTS

| | | |
|---|---|---|
| EP | 1287840 A1 | 3/2003 |
| EP | 1462134 A1 | 9/2004 |
| EP | 1712178 A2 | 10/2006 |
| EP | 1883268 A2 | 2/2007 |
| EP | 1777984 A1 | 4/2007 |
| JP | 2006-034845 | 2/2006 |
| WO | WO 91/04760 A1 | 4/1991 |
| WO | WO93/02720 | 2/1993 |
| WO | WO 95/26009 | 9/1995 |
| WO | WO 96/25965 | 8/1996 |
| WO | WO 96/31106 | 10/1996 |
| WO | WO 97/30742 | 8/1997 |
| WO | WO 99/07425 | 2/1999 |
| WO | WO 99/43283 | 9/1999 |
| WO | WO 01/24690 A2 | 4/2001 |
| WO | WO 01/26020 A1 | 4/2001 |
| WO | WO 01/41849 A2 | 6/2001 |
| WO | WO 01/88828 | 11/2001 |
| WO | WO 01/93926 A2 | 12/2001 |
| WO | WO 02/24257 A1 | 3/2002 |
| WO | WO 03/057283 A1 | 7/2003 |
| WO | WO 03/095001 A1 | 11/2003 |
| WO | WO 03/097133 A1 | 11/2003 |
| WO | WO 2004/041330 A2 | 5/2004 |
| WO | WO 2005/050526 A2 | 6/2005 |
| WO | WO 2005/077441 A2 | 8/2005 |
| WO | WO 2006/045525 A1 | 5/2006 |
| WO | WO 2006/085175 A1 | 8/2006 |
| WO | WO 2006/085204 A1 | 8/2006 |
| WO | WO 2006083876 A2 * | 8/2006 |
| WO | WO 2006/109778 A1 | 10/2006 |
| WO | WO 2006/123956 A1 | 11/2006 |
| WO | WO2006/125692 | 11/2006 |
| WO | WO 2007/088444 A1 | 8/2007 |
| WO | WO 2010/114392 A1 | 10/2010 |
| WO | WO 2013/043063 A1 | 3/2013 |
| WO | WO 2013/044172 A1 | 3/2013 |

OTHER PUBLICATIONS

Merle Tingelstad, "Revolutionary Medical Technology Increases Demand for Flexible Interconnects," [online] May 15, 2006 [retrieved on Nov. 15, 2006] Retrieved from the Internet <URL: http://www.ecmmag.com/index.asp?layout=articlePrint&ArticleID=CA6332947>.

"Flexible circuits / Flex circuits / Flexible Technology Ltd.," Flexible Technology Limited [online] [retrieved on Aug. 28, 2006] Retrieved from the Internet <URL: http://www.flexibletechnology.com/>.

"Flexible circuits capabilities of Flexible Technology Limited," Our Flexible Circuits Capabilities [online] [retrieved on Aug. 28, 2006]

(56) References Cited

OTHER PUBLICATIONS

Retrieved from the Internet <URL: http://www.flexibletechnology.com/Flexible circuits Capability.htm >.
"Flex Circuits/flexible circuits design guide," [online] [retrieved on Aug. 28, 2006] Retrieved from the Internet <URL: http://flexiblecircuit.co.uk/Flex Circuits Design Guide.htm >.
"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >.
"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/productcatalogue.asp >.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >.
Roger Allan, "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>.
RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8.
Dr. Oliver Scholz, "Drug depot in a tooth," [online] [retrieved on Feb. 6, 2007] Retrieved from the Internet <URL: http://www.fraunhofer.de/fbg/EN/press/pi/2007/02Mediendienst22007Thema2.jsp?print=true.
Heartsine Technology, samaritan™ PAD Accessories [online] [retrieved on Jun. 1, 2007] Retrieved from the Internet <URL: http://www.heartsine.com/aboutsam-accessories.htm>.
CliniSense Corporation, "Drug delivery devices a potentially harsh environment for drugs," Stability [online] [retrieved on Jun. 1, 2007] Retrieved from the Internet <URL: http://www.clinisense.com/devices.htm>.
CliniSense Corporation, "LifeTrack Technology a new method to detect improper storage." Stability [online] [retrieved on Jun. 1, 2007] Retrieved from the Internet <URL: http://www.clinisense.com/tech.htm>.
AED Professionals™ Brochure [online] [retrieved on Jun. 1, 2007] Retrieved from the Internet <URL: http://www.aedprofessionals.com/>.
Daniel Ruppar, "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer print?pg=44&pm=8 >.
Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamel_trainer.html/>.
Laura Lin Gosbee, "Nuts! I Can't Figure Out How to Use My Life-Saving Epinephrine Auto-Injector," Joint Commision Journal on Quality and Safety, vol. 30, No. 4, Apr. 2004.
Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>.
Search Report and Written Opinion for International Patent Application No. PCT/US06/03415 mailed Jul. 13, 2006, 10 pages.
Search Report and Written Opinion for International Patent Application No. PCT/US07/007626 mailed Sep. 29, 2008.
Combined Search and Examination Report for GB 0818178.6, mailed Dec. 1, 2008.
Office Action for U.S. Appl. No. 11/621,236, mailed Feb. 3, 2009.
Examination Report for British Patent Application No. GB 0818178.6, mailed Mar. 23, 2009.
Examination Report for British Patent Application No. GB 0905194.7, mailed May 8, 2009.
Final Office Action for U.S. Appl. No. 11/621,236, mailed Jul. 1, 2009.
Examination Report for British Patent Application No. GB 0818178.6, mailed Jul. 9, 2009.
Search Report and Written Opinion for International Patent Application No. PCT/US09/63983, mailed Feb. 25, 2010.
Search Report for European Patent Application No. 09150135.3, mailed Mar. 15, 2010.
IPRP for International Patent Application No. PCT/US2009/043578, mailed Nov. 17, 2010.
Office Action for U.S. Appl. No. 12/180,708, mailed Feb. 28, 2011.
Final Office Action for U.S. Appl. No. 11/679,331, mailed Feb. 15, 2011.
Search and Examination Report for British Patent Application No. 1104754.5, mailed May 18, 2011.
Office Action for Japanese Patent Application No. JP2009-502964, mailed May 23, 2011.
Search and Examination Report for British Patent Application No. 1108993.5, mailed Jun. 17, 2011.
Office Action for European Patent Application No. 09150135.3, mailed Jul. 11, 2011.
Office Action for Israel Patent Application No. 184552, mailed Jul. 28, 2011.
Final Office Action for U.S. Appl. No. 11/671,025, mailed Sep. 8, 2011.
Office Action for U.S. Appl. No. 12/794,020, mailed Oct. 25, 2011.
Office Action for U.S. Appl. No. 12/119,016, mailed Nov. 3, 2011.
Office Action for U.S. Appl. No. 12/615,636, mailed Jan. 25, 2012.
Examination Report for British Patent Application No. 1019599.8, mailed Feb. 7, 2012.
English Translation of Office Action for Japanese Patent Application No. 2009-502964, mailed May 17, 2012.
English Translation of Office Action for Chinese Patent Application No. 200980124254.1, mailed Oct. 30, 2012.
Office Action for U.S. Appl. No. 13/924,037, mailed Feb. 14, 2014.
Office Action for Canadian Patent Application No. 2,644,547, mailed Feb. 14, 2014.
Office Action for U.S. Appl. No. 11/679,331, mailed Feb. 15, 2011.
Office Action for U.S. Appl. No. 11/679,331, mailed May 12, 2010.
Non-Final Office Action for U.S. Appl. No. 13/404,699, mailed Mar. 10, 2014.

\* cited by examiner

SIMULATED MEDICAMENT DELIVERY DEVICE HAVING AN ELECTRONIC CIRCUIT SYSTEM

CROSS-REFERENCE TO RELATED APPLICATIONS

This application is a continuation of U.S. patent application Ser. No. 13/550,893, entitled "Medicament Delivery Device having an Electronic Circuit System," filed Jul. 17, 2012, which is a continuation of U.S. patent application Ser. No. 12/119,016, now U.S. Pat. No. 8,231,573, entitled "Medicament Delivery Device Having an Electronic Circuit System," filed May 12, 2008, which is a continuation-in-part of U.S. patent application Ser. No. 11/679,331, entitled "Medical Injector Simulation Device," filed Feb. 27, 2007, which is a continuation-in-part of U.S. patent application Ser. No. 11/671,025, now U.S. Pat. No. 8,172,082, entitled "Devices, Systems and Methods for Medicament Delivery," filed Feb. 5, 2007, which is a continuation-in-part of U.S. patent application Ser. No. 11/621,236, now U.S. Pat. No. 7,731,686, entitled "Devices, Systems and Methods for Medicament Delivery," filed Jan. 9, 2007, which is a continuation-in-part of U.S. patent application Ser. No. 10/572,148, now U.S. Pat. No. 7,749,194, entitled "Devices, Systems and Methods for Medicament Delivery," filed Mar. 16, 2006, which is a national stage filing under 35 U.S.C. §371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005, each of which is incorporated herein by reference in its entirety. U.S. patent application Ser. Nos. 11/621, 236, 11/679,331 and 11/671,025 also claim priority to U.S. Provisional Application Ser. No. 60/787,046, entitled "Devices, Systems and Methods for Medicament Delivery," filed Mar. 29, 2006, which is incorporated herein by reference in its entirety.

BACKGROUND

The invention relates generally to a medical device, and more particularly to a medicament delivery device, and/or a simulated medicament delivery device having an electronic circuit system.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Because emergency medical facilities may not be available when an individual is suffering from an allergic reaction, some individuals carry a medicament delivery device, such as, for example, a auto-injector, to rapidly self-administer a medicament in response to an allergic reaction.

To actuate such a medicament delivery device, however, the user may be required to execute a series of operations. For example, to actuate some known auto-injectors, the user must remove a protective cap, remove a locking device, place the auto-injector in a proper position against the body and then press a button to actuate the auto-injector. Failure to complete these operations properly can result in an incomplete injection and/or injection into an undesired location of the body. In certain instances, for example, users who have become confused in the operation of some known auto-injectors have inadvertently injected the medicament into their thumb by improperly positioning the auto-injector.

The likelihood of improper use of known medicament delivery devices can be compounded by the nature of the user and/or the circumstances under which such devices are used. For example, many users are not trained medical professionals and may have never been trained in the operation of such devices. Moreover, in certain situations, the user may not be the patient, and may therefore have no experience with the medicament delivery device. Similarly, because some known medicament delivery devices are configured to be used relatively infrequently in response to an allergic reaction or the like, even those users familiar with the device and/or who have been trained may not be well practiced at operating the device. Finally, such devices are often used during an emergency situation, during which even experienced and/or trained users may be subject to confusion, panic, and/or the physiological effects of the condition requiring treatment.

Some known medicament delivery devices include printed instructions to inform the user of the steps required to properly deliver the medicament. Such printed instructions, however, can be inadequate for the class of users and/or the situations described above. Moreover, because some known medicament delivery devices, such as, for example, auto-injectors, pen injectors, inhalers or the like, can be compact, such printed instructions may be too small to read and comprehend during an emergency situation.

Some known medicament delivery devices are associated with simulated medicament delivery devices (e.g., "trainers") to provide a method for users to practice using the medicament delivery device without being exposed to the medicament and/or needles typically contained therein. Such simulated medicament delivery devices, however, can also include inadequate use instructions as described above.

Monitoring the patient's compliance with known medicament delivery devices can also be problematic. For example, some known medicament delivery systems include a medicament delivery device and an electronic system to assist the user in setting the proper dosage and/or maintaining a compliance log. Such known medicament delivery systems and the accompanying electronic systems can be large and therefore not conveniently carried by the user. Such known medicament delivery systems and the accompanying electronic systems can also be complicated to use and/or expensive to manufacture. Moreover, some known medicament delivery systems include sensors disposed within the medicament delivery path, which can interfere with the delivery, result in contamination, or the like.

Thus, a need exists for medicament delivery systems and/or devices that provide instructions that can be easily understood by a user in any type of situation. Additionally, a need exists for simulated medicament delivery systems and/or devices that can provide instructions and that can be reused multiple times. Moreover, a need exists for medicament delivery systems and/or devices that can provide compliance information associated with the use of the device and/or that can communicate electronically with other communications devices.

SUMMARY

Medicament delivery devices are described herein. In some embodiments, an apparatus includes a medical injector and an electronic circuit system. The medical injector includes a housing, a medicament container, and a medicament delivery member. The housing defines a first region and a second region. The first region includes the medicament container and is physically isolated from the second region. The electronic circuit system is configured to be disposed within the second region defined by the housing. The electronic circuit system is configured to output an electronic output associated with a use of the medical injector.

DETAILED DESCRIPTION

Figure 1:
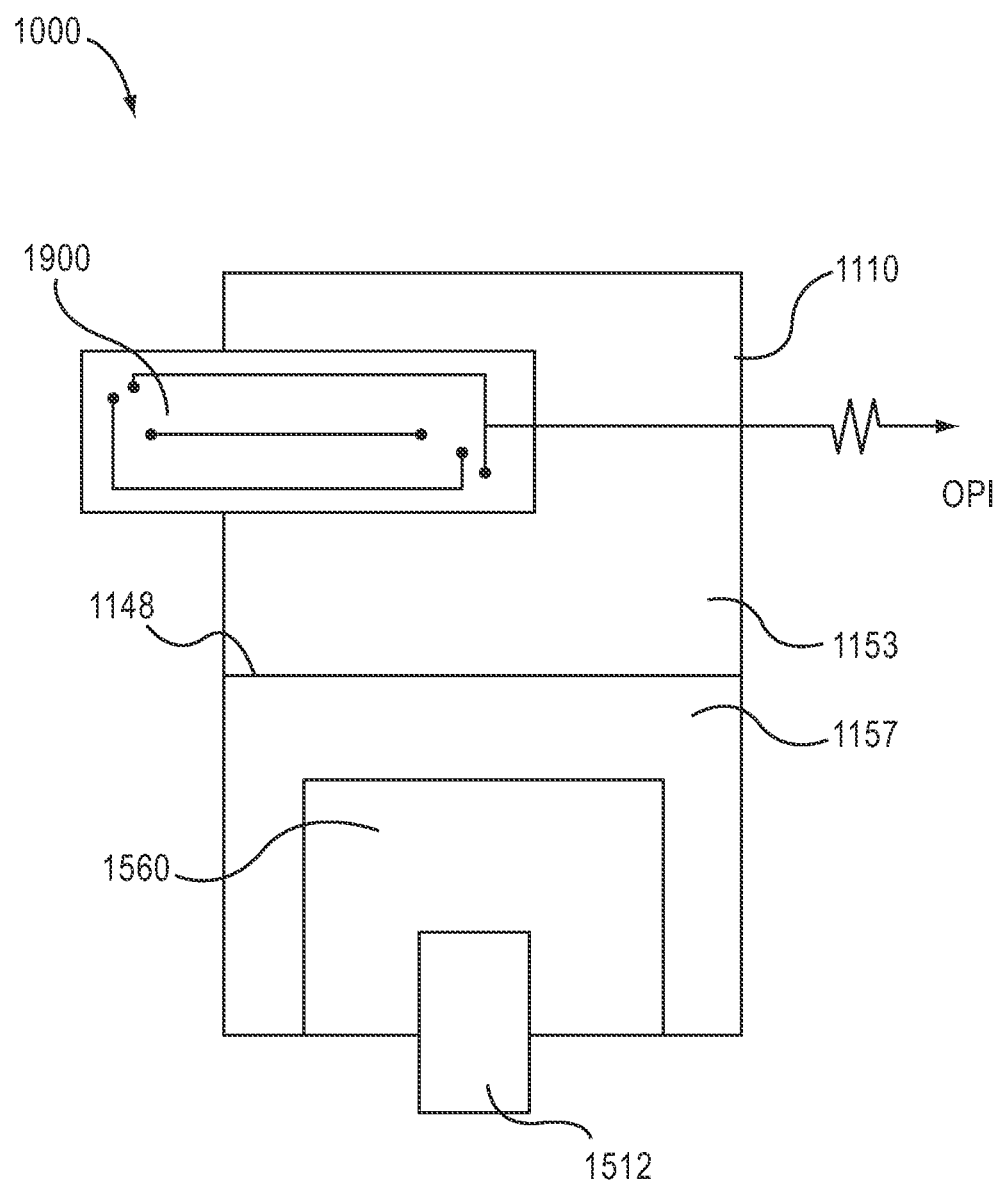
FIG. 1 is a schematic illustration of a medicament delivery device according to an embodiment of the invention.

In some embodiments, an apparatus includes a medical injector and an electronic circuit system. The medical injector includes a housing, a medicament container, and a medicament delivery member. The housing defines a first region and a second region. The first region includes the medicament container and is physically isolated from the second region. The electronic circuit system is configured to be disposed within the second region defined by the housing. The electronic circuit system is configured to output an electronic output associated with a use of the medical injector.

In some embodiments, an apparatus includes a medical injector and an electronic circuit system. The medical injector includes a housing, a medicament container, and a medicament delivery member. The medicament delivery member can be, for example, a needle or an injection nozzle. The housing defines a first region and a second region. The first region includes the medicament container and is physically isolated from the second region. The electronic circuit system is configured to be disposed within the second region defined by the housing. The electronic circuit system includes a printed circuit board having a substrate and an electrical conductor disposed on the substrate. The substrate of the printed circuit board is configured to receive an actuator configured to disrupt the electrical conductor. The actuator can be, for example, an actuator configured to initiate delivery of a medicament from the medical injector. The electronic circuit system is configured to output an electronic output associated with a use of the medical injector when the electrical conductor is disrupted. In some embodiments, the electronic output can be, for example, associated with recorded speech.

In some embodiments, an apparatus includes a medicament delivery device and an electronic circuit. The medicament delivery device, which can be, for example, a pen injector, an auto-injector, an inhaler or a transdermal delivery device, includes a housing, a medicament container, and a medicament delivery member. The medicament container and at least a portion of the medicament delivery member are disposed within the housing. The medicament container and the medicament delivery member define a medicament delivery path. The electronic circuit system is coupled to the housing and is physically isolated from the medicament delivery path. The electronic circuit system is configured to output an electronic output in response to a delivery of a medicament via the medicament delivery path. In some embodiments, the electronic output can be, for example, a visual output, an audible output, and/or a haptic output.

In some embodiments, an apparatus includes a medical injector having a housing, a medicament container and a medicament delivery member. The housing defines a first region including at least the medicament container and a second region configured to receive an electronic circuit system. The first region of the housing is physically isolated from the second region of the housing. The electronic circuit system is configured to output an electronic output associated with a use of the medical injector. In some embodiments, the medical injector is configured to deliver only a single dose of medicament into a body. In other embodiments, the medical injector is configured to be reusable.

In some embodiments, an apparatus includes an electronic circuit system configured to be coupled to a medical injector such that, the electronic circuit system is physically isolated from a medicament delivery path. The electronic circuit system is configured to output an electronic output in response to the delivery of a medicament via the medicament delivery path. The electronic output can be, for example, a visual output, an audible output, and/or a haptic output.

In some embodiments, a method includes assembling a medical device configured to deliver a medicament into a body of a patient. The medical device includes a housing, a medicament container, an actuator and a safety lock. The medicament container is disposed within the housing. The actuator is configured to initiate delivery of the medicament from the medicament container when the actuator is actuated. The safety lock is configured to prevent actuation of the actuator. An electronic circuit system is coupled to the housing of the assembled medical device such that an opening defined by a substrate of the electronic circuit system is disposed about a portion of the safety lock. The electronic circuit system is configured to output an electronic output in response to a movement of the safety lock within the opening.

In some embodiments, a method includes coupling an electronic circuit system to a simulated medicament delivery device such that a portion of the housing actuates a switch of the electronic circuit system. The simulated medicament delivery device is configured to simulate an actual medicament delivery device. The electronic system is configured to output an electronic output associated with a use of the simulated medicament delivery device and a state of the switch. The electronic output can be, for example, a visual output, an audible output, and/or a haptic output.

In some embodiments, an apparatus includes a simulated medicament delivery device and an electronic circuit system. The simulated medicament delivery device, which can be, for example, a pen injector, an auto-injector, an inhaler or a transdermal delivery device, is configured to simulate an actual medicament delivery device. The simulated medicament delivery device includes a housing, a safety lock and a cover. The safety lock is configured to simulate a safety lock of the actual medicament delivery device. The cover is removably disposed about at least a portion of the housing. The electronic circuit system is configured to output a first plurality of electronic outputs when the cover is removed from the housing a first time. The electronic circuit system is configured to output a second plurality of electronic outputs when the cover is removed from the housing a second time. The second plurality of electronic outputs are different from the first plurality of electronic outputs. In some embodiments, the first and/or the second plurality of electronic outputs can be, for example, visual outputs, audible outputs, and/or haptic outputs.

In some embodiments, a processor-readable medium storing code representing instructions to cause a processor to perform a process includes code to output a first electronic output associated with a use of a simulated medicament delivery device when a cover is removed from the simulated medicament delivery device a first time. The processor-readable medium includes code to output a second electronic output associated with a use of the simulated medicament delivery device when the cover is removed a second time. The second electronic output is different from the first electronic output. The simulated medicament delivery device can be, for example, a pen injector, an auto-injector, an inhaler or a transdermal delivery device. In some embodiments, the first and/or second electronic outputs can be, for example, a visual output, an audible output, and/or a haptic output.

As used in this specification and the appended claims, the words "proximal" and "distal" refer to direction closer to and away from, respectively, an operator (e.g., surgeon, physician, nurse, technician, etc.) of the medical device. Thus, for example, the end of the medicament delivery device contacting the patient's body would be the distal end of the medicament delivery device, while the end opposite the distal end would be the proximal end of the medicament delivery device.

FIG. 1 is a schematic illustration of a medical injector 1000, according to an embodiment of the invention. The medical injector 1000 includes a housing 1110, a medicament container 1560, a medicament delivery member 1512 and an electronic circuit system 1900. The housing 1110 includes a sidewall 1148 that defines a first region 1157 and a second region 1153 within the housing 1110. More particularly, the sidewall 1148 physically isolates the first region 1157 from the second region 1153. Said another way, the sidewall 1148 is devoid of openings such that the first region 1157 is fluidically and/or physically isolated from the second region 1153. Said yet another way, the sidewall 1148 is disposed between the first region 1157 and the second region 1153 such that the first region 1157 is separated from the second region 1153. Although the first region 1157 and the second region 1153 are shown in FIG. 1 as being two-dimensional areas, in some embodiments, the first region 1157 and/or the second region 1153, can be fully enclosed volumes within the housing, and/or volumes within the housing 1110 having an opening to an area outside of the housing. Similarly stated, the first region and/or the second region can be cavities, defined by the housing 1110 and/or the sidewall 1148.

The medicament container 1560, which can be, for example, a pre-filled cartridge, a vial, an ampule or the like, is disposed within the first region 1157 of the housing 1110. At least a portion of the medicament delivery member 1512 is disposed within the first region 1157 of the housing 1110. In some configurations, the medicament delivery member 1512 can be in fluid communication with the medicament container 1560. In this manner, a medicament can be conveyed from the medicament container 1560 to a region outside the housing 1110 via the medicament delivery member 1512. The medicament delivery member 1512 can include, for example, a needle and/or a nozzle.

At least a portion of the electronic circuit system 1900 is disposed within the second region 1153 of the housing 1110. Accordingly, the portion of the electronic circuit system 1900 is disposed within the housing 1110 such that the portion of the electronic circuit system 1900 is fluidically and/or physically isolated from the medicament container 1560 and/or the medicament delivery member 1512.

The electronic circuit system 1900 is configured to output an electronic output OP1 associated with a use of the medical injector 1000. For example, in some embodiments, the electronic output OP1 can be associated with an instruction for using the medical injector 1000. In other embodiments, the electronic output OP1 can be a post-use instruction, such as, for example, a recorded message notifying the user that the injection is complete, instructing the user on post-injection disposal and safety procedures, instructing the user to seek post-injection medical treatment, and/or the like. In yet other embodiments, the electronic output OP1 can be associated with the patient's compliance in using medical injector 1000. In some embodiments, the electronic output OP1 can be associated with an actuation of the medical injector 1000. Said another way, the electronic circuit system 1900 can be configured to output the electronic output OP1 in response to actuation of the medical injector 1000.

The electronic output OP1 can be, for example, a visual output such as, for example, a text message to display on a screen (not shown), and/or an LED. In some embodiments, the electronic output OP1 can be an audio output, such as, for example, recorded speech, a series of tones, and/or the like. In other embodiments, the electronic output OP1 can be a wireless signal configured to be received by a remote device.

The medical injector 1000 can be any suitable medical injector for injecting medicament into a body of a patient. For example, the medical injector 1000 can be a syringe, pen injector, auto-injector or the like. In some embodiments, the medical injector 1000 can be a chronic-care injector. Said another way, the medical injector 1000 can be a reusable device containing multiple doses of medicament. For example, a medical injector 1000 having multiple doses of medicament can be used to manage insulin delivery and/or delivery of other medicaments (e.g., to treat Multiple Sclerosis, Anemia, Rhuematoid Arthritis, Osteoporosis or the like), which can require daily, weekly, and/or monthly injections. In other embodiments, the medical injector 1000 can be a single-use device. Said another way, the medical injector 1000 can contain a single dose of medicament. In some embodiments, medical injector 1000 can include the same dosage of a medicament, and can be prescribed as a part of a chronic-care medicament regimen, clinical trial, or the like. In other embodiments, medical injector 1000 can include different dosages, and/or different medicament compositions.

The sidewall 1148 can be any suitable structure to isolate the first region 1157 within the housing 1110 from the second region 1153 within the housing 1110. In some embodiments, the sidewall 1148 can be rigid. In other embodiments, the sidewall 1148 can be a movable member such as, for example, a piston. In yet other embodiments, the sidewall 1148 can be a flexible member such as, for example, a diaphragm. In some embodiments, the sidewall 1148 can be constructed from a transparent material such that light can pass from the first region 1157 to the second region 1153, and vice versa. A transparent sidewall can be used in conjunction with an optical sensor. The sidewall 1148 can be integrally formed with the housing 1110 or can be formed separately from the housing 1110.

The electronic circuit system 1900 can include any suitable electronic components operatively coupled to produce and/or output the electronic output OP1 and/or to perform the functions described herein. The electronic circuit system 1900 can be similar to the electronic circuit systems described in U.S. patent application Ser. No. 11/621,236, entitled "Devices, Systems and Methods for Medicament Delivery," filed Jan. 9, 2007, which is incorporated herein by reference in its entirety.

Figure 2:
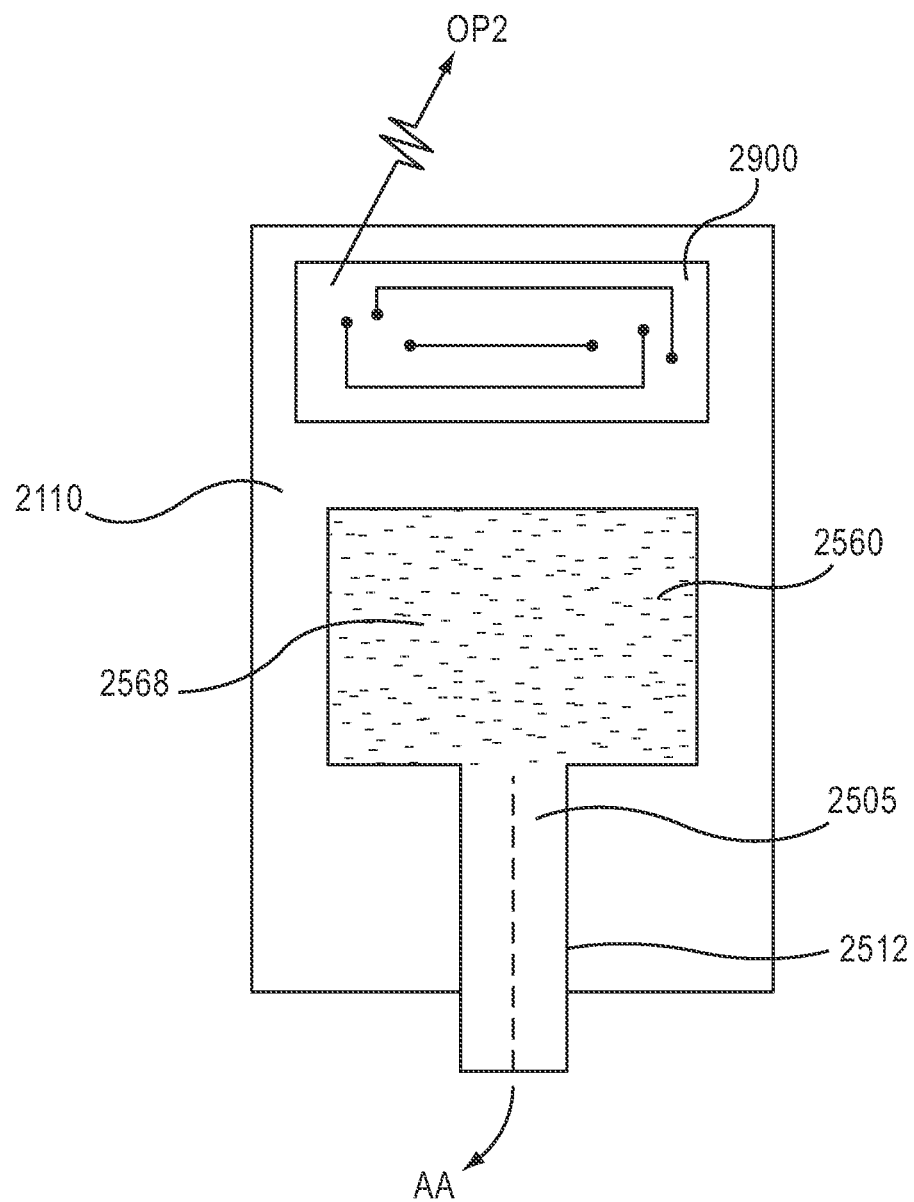
FIG. 2 is a schematic illustration of a medicament delivery device according to an embodiment of the invention.

FIG. 2 is a schematic illustration of a medicament delivery device 2000, according to an embodiment of the invention. The medicament delivery device 2000 includes a housing 2110, a medicament container 2560, a medicament delivery member 2512 and an electronic circuit system 2900. The medicament container 2560, which can be, for example, a pre-filled cartridge, a vial, an ampule or the like, is disposed within the housing 2110. At least a portion of the medicament delivery member 2512 is disposed within the housing 2110. The medicament delivery member 2512 can include any suitable member configured to convey a medicament from the medicament container 2560 to a location within a patient's body. For example, in some embodiments, the medicament delivery member 2512 can be a needle, a nozzle, and/or an inhaler mouth piece.

In use, the medicament delivery member 2512 can be in fluid communication with the medicament container 2560. In this manner, the medicament delivery member 2512 and the medicament container 2560 can define a medicament delivery path 2505 through which a medicament 2568 can be conveyed from the medicament container 2560 to a location outside the housing 2110 via the medicament delivery member 2512 as shown by arrow AA. In some embodiments, the medicament delivery path 2505 can include portions of a lumen defined by the medicament delivery member 2512 and/or the connection between the medicament delivery member 2512 and the medicament container 2560.

The electronic circuit system 2900 is coupled to the housing 2110 and is fluidically and/or physically isolated from the medicament delivery path 2505. The electronic circuit system 2900 is configured to output an electronic output OP2 in response to a delivery of the medicament 2568 via the medicament delivery path 2505. In this manner, the electronic circuit system 2900 can output the electronic output OP2 in an unobtrusive manner and/or without impeding the delivery of the medicament 2568 through the medicament delivery path 2505. In some embodiments, for example, the electronic output OP2 can be a post-use instruction, such as, for example, a recorded message notifying the user that the injection is complete, instructing the user on post-injection disposal and safety procedures, instructing the user on post-injection medical treatment, and/or the like. In other embodiments, the electronic output OP2 can be associated with the patient's compliance in using the medicament delivery device 2000. For example, in some embodiments, the electronic output OP2 can be a signal sent to a compliance tracking monitor to record the data and/or time of use of the medicament delivery device 2000.

The electronic output OP2 can be, for example, a visual output such as, for example, a text message to display on a screen (not shown), and/or an LED. In some embodiments, the electronic output OP2 can be an audio output, such as, for example, recorded speech, a series of tones, and/or the like. In other embodiments, the electronic output OP2 can be a wireless signal configured to be received by a remote device.

The medicament delivery device 2000 can be any suitable medicament delivery device for delivering the medicament 2568 to a body of a patient. For example, the medicament delivery device 2000 can be a syringe, pen injector, auto-injector, inhaler or the like. In some embodiments, the medicament delivery device 2000 can be a chronic-care delivery device. Said another way, the medicament delivery device 2000 can be a reusable device containing multiple doses of medicament 2568. In other embodiments, the medicament delivery device 2000 can be a single-use device. Said another way, the medicament delivery device 2000 can contain a single dose of medicament 2568.

The electronic circuit system 2900 can include any suitable electronic components operatively coupled to produce and/or output the electronic output OP2 and/or to perform the functions described herein. The electronic circuit system 1900 can be similar to the electronic circuit system 1900 as described above with reference to FIG. 1.

Figure 3:
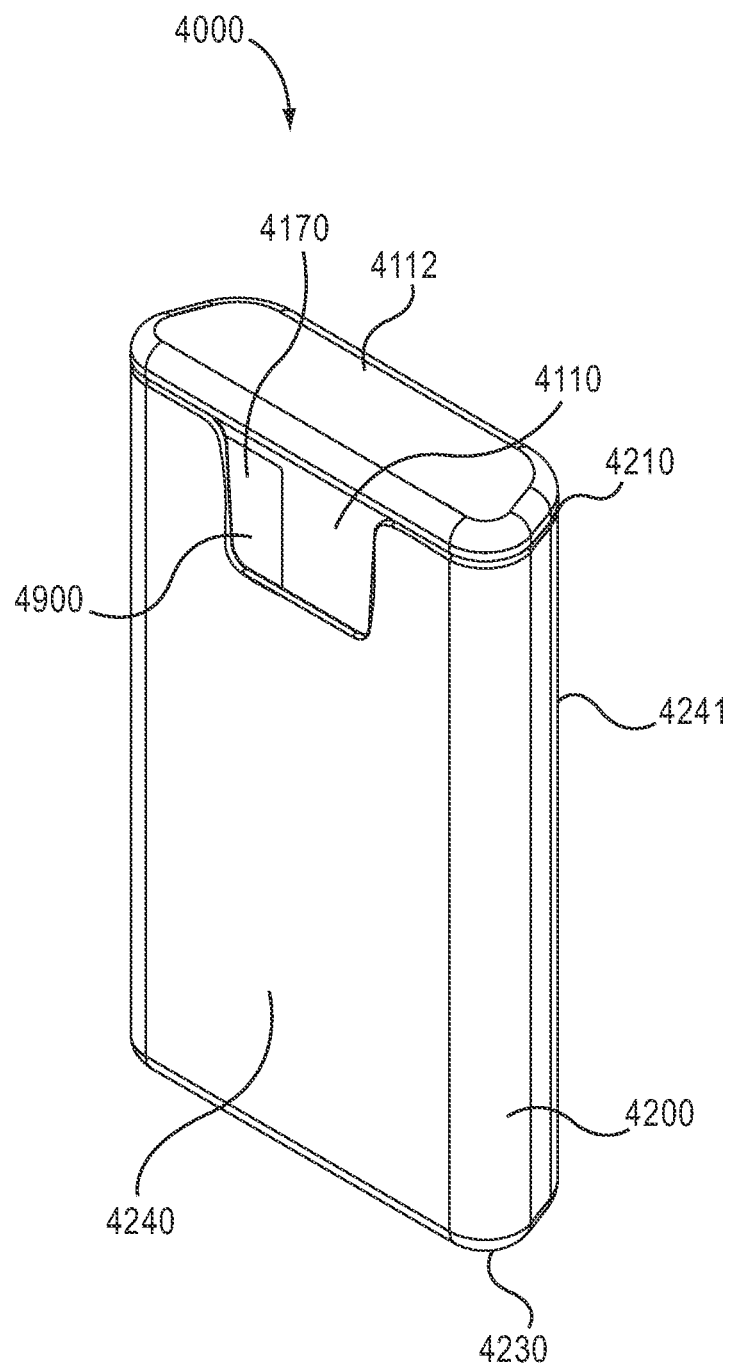
FIGS. 3 and 4 are perspective views of a medical injector according to an embodiment of the invention, in a first configuration.
Figure 4:
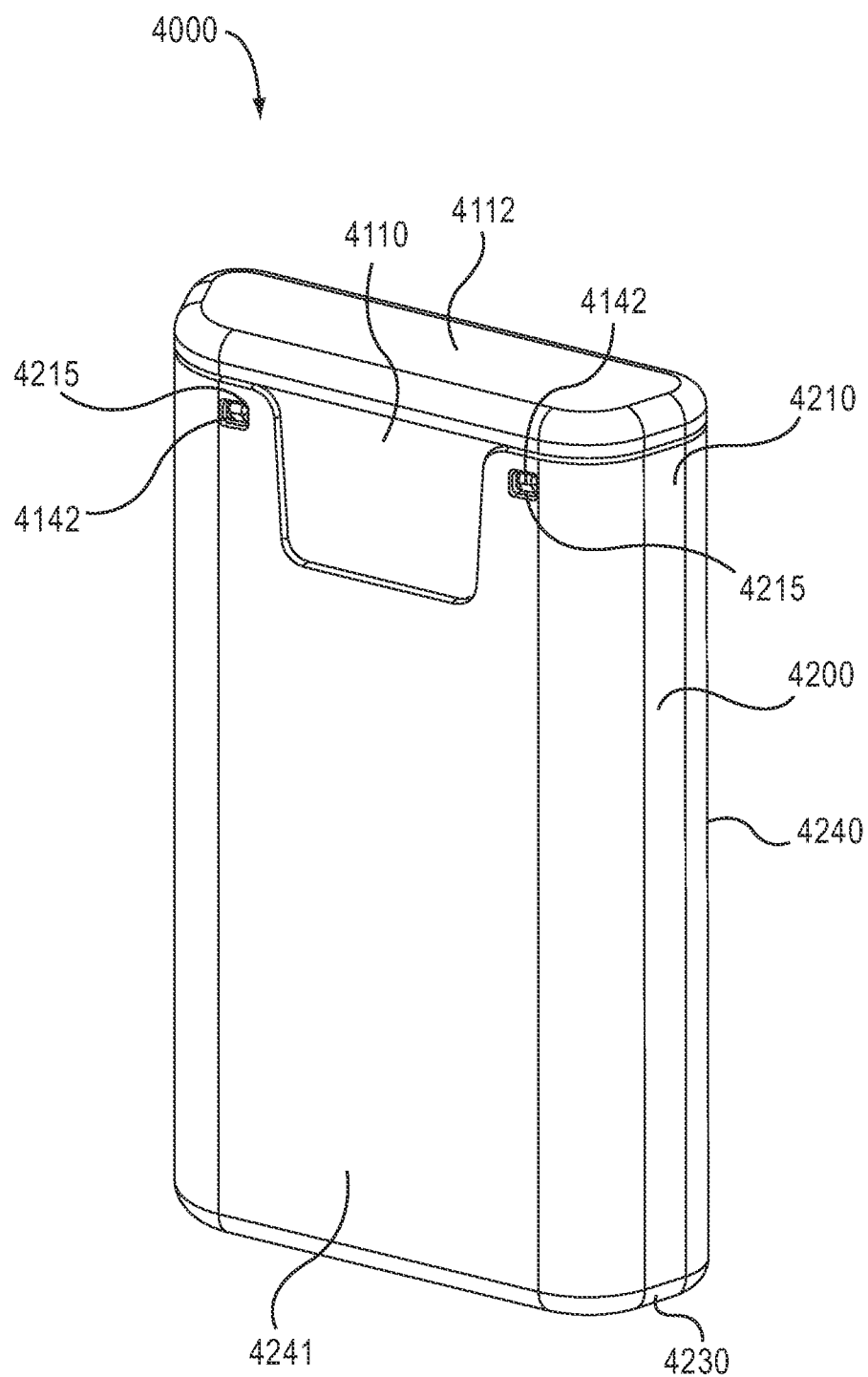
Figure 5:
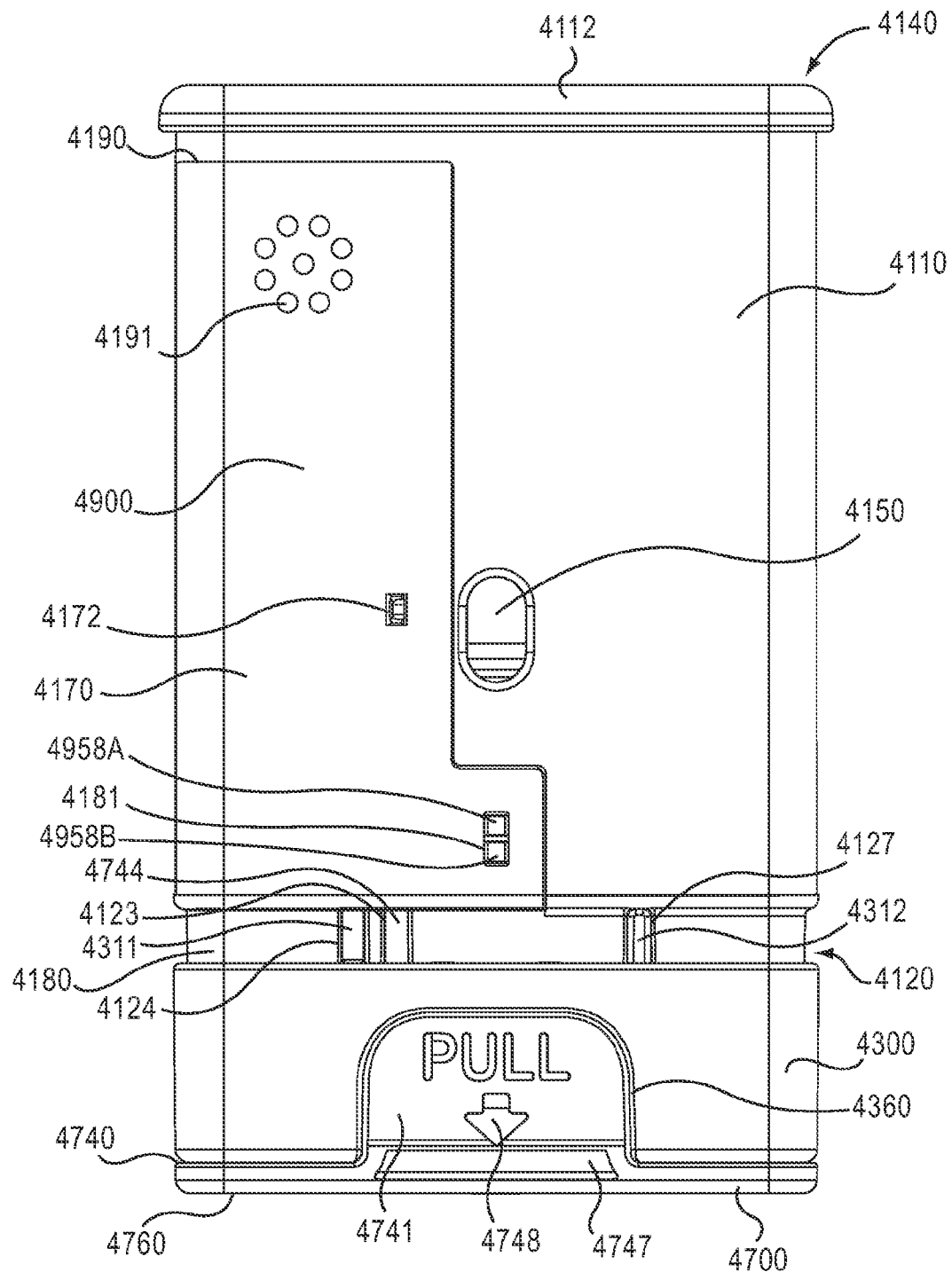
FIG. 5 is a front view of the medical injector illustrated in FIG. 3 with the cover removed.

FIGS. 3-34 show a medical injector 4000, according to an embodiment of the invention. FIGS. 3-4 are perspective views of the medical injector 4000 in a first configuration (i.e., prior to use). The medical injector 4000 includes a housing 4110, a delivery mechanism 4500 (see e.g., FIG. 12), an electronic circuit system 4900 (see e.g., FIGS. 13-23), a cover 4200 (see e.g., FIGS. 24-25), a safety lock 4700 (see e.g., FIGS. 26-29) and a base 4300 (see e.g., FIGS. 30-31). A discussion of the components of the medical injector 4000 will be followed by a discussion of the operation of the medical injector 4000.

As shown in FIGS. 5-11, the housing 4110 has a proximal end portion 4140 and a distal end portion 4120. The housing 4110 defines a first status indicator aperture 4150 and a second status indicator aperture 4151. The first status indicator aperture 4150 defined by the housing 4110 is located on a first side of the housing 4110, and the second status indicator aperture 4151 of the housing 4110 is located on a second side of the housing 4110. The status indicator apertures 4150, 4151 can allow a patient to monitor the status and/or contents of a medicament container 4560. For example, by visually inspecting the status indicator apertures 4150, 4151, a patient can determine whether the medicament container 4560 contains a medicament and/or whether a medicament has been dispensed.

Figure 9:
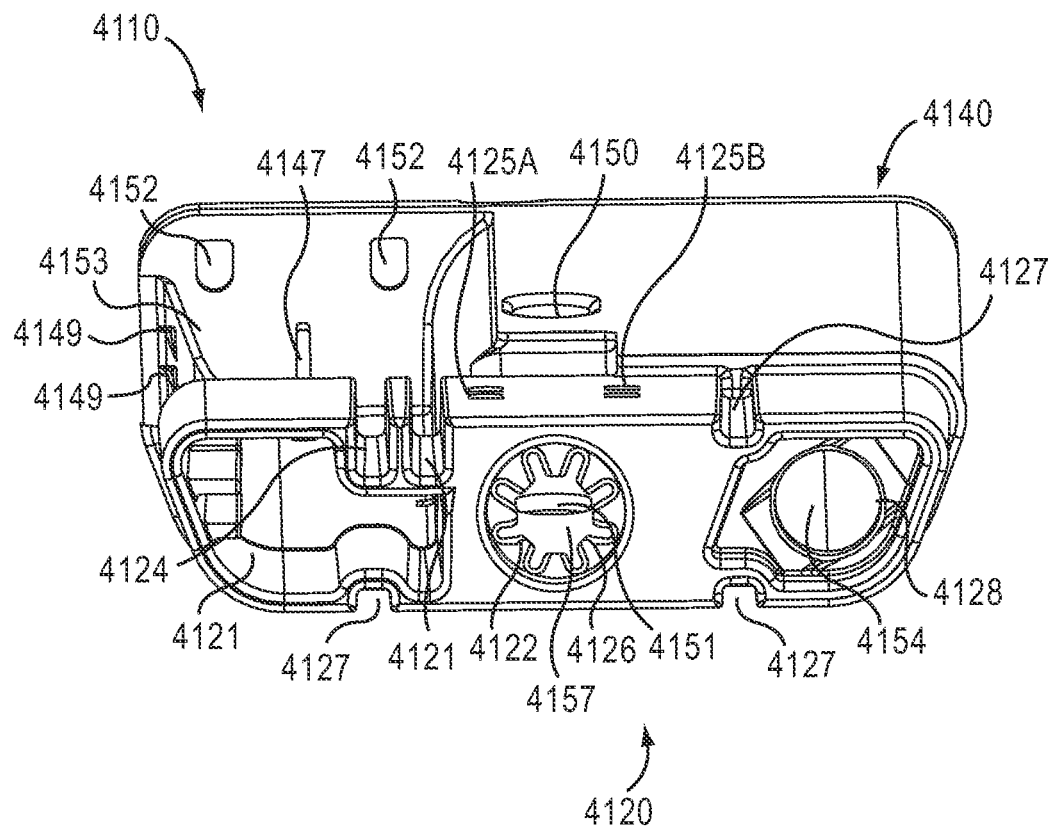
FIG. 9 is a bottom perspective view of a housing of the medical injector illustrated in FIG. 3.
Figure 10:
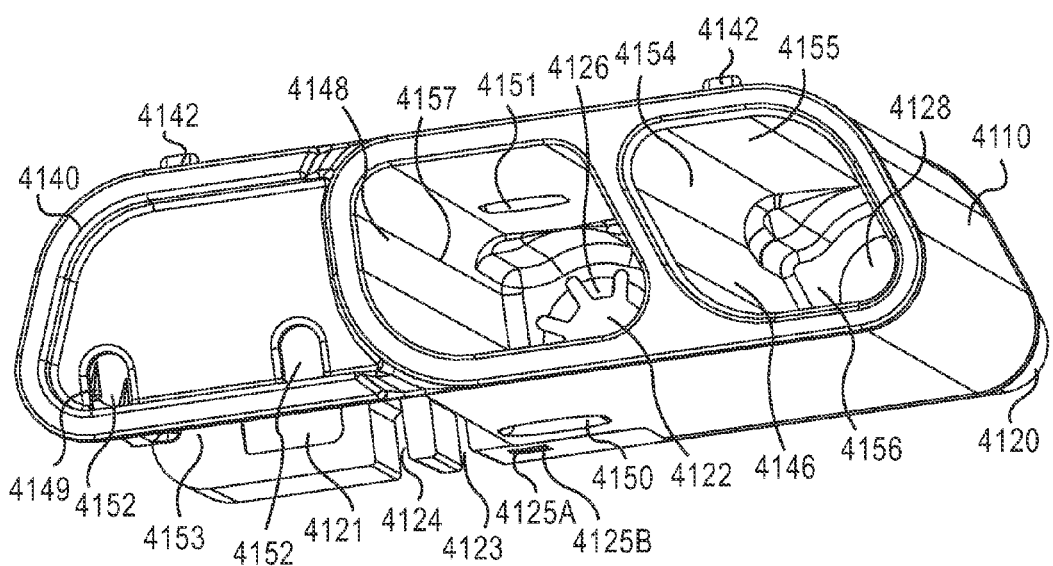
FIG. 10 is a top perspective view of a housing of the medical injector illustrated in FIG. 3.

As shown in FIGS. 9 and 10, the housing 4110 defines a gas cavity 4154, a medicament cavity 4157 and an electronic circuit system cavity 4153. The gas cavity 4154 has a proximal end portion 4155 and a distal end portion 4156. The gas cavity 4154 is configured to receive the gas container 4570 and the release member 4540 of the medicament delivery mechanism 4500 (see e.g., FIG. 12) as described in further detail herein. The proximal end portion 4155 of the gas cavity 4154 is configured to receive the gas container retention member 4580 of the proximal cap 4112 of the housing 4110, as described in further detail herein. The gas cavity 4154 is in fluid communication with the medicament cavity 4157 via a gas passageway 4144, as described in further detail herein, and the gas cavity 4154 is in fluid communication with a region outside the housing 4110 via a safety lock aperture 4128.

The medicament cavity 4157 is configured to receive a portion of the delivery mechanism 4500. In particular, the carrier 4520, the moveable member 4530 and the needle 4512 of the medicament delivery mechanism 4500 are movably disposed in the medicament cavity 4157. The medicament cavity 4157 is in fluid communication with a region outside the housing 4110 via a needle aperture 4122.

The electronic circuit system cavity 4153 is configured to receive the electronic circuit system 4900. The housing 4110 has protrusions 4149 (see e.g., FIG. 8) configured to stabilize the electronic circuit system 4900 when the electronic circuit system 4900 is disposed within the electronic circuit system cavity 4153. The housing 4110 also defines connection apertures 4152 configured to receive connection protrusions 4171 of the electronic circuit system 4900, and aperture 4145 (see e.g., FIG. 6) configured to receive a portion of a protrusion 4174 of the electronic circuit system 4900. In this manner, the electronic circuit system 4900 can be coupled to the housing 4110 within the electronic circuit system cavity 4153. In other embodiments, the electronic circuit system 4900 can be coupled within the electronic circuit system cavity 4153 by other suitable means such as an adhesive, a clip and/or the like.

The electronic circuit system cavity 4153 is fluidically and/or physically isolated from the gas cavity 4154 and/or the medicament cavity 4157 by a sidewall 4148. The sidewall 4148 can be any suitable structure to isolate the electronic circuit system cavity 4153 within the housing 4110 from the gas cavity 4154 and/or the medicament cavity 4157 within the housing 4110. Similarly, the gas cavity 4154 and the medicament cavity 4157 are separated by a sidewall 4146. In some embodiments, sidewall 4146 can be similar to the sidewall 4148, which isolates the gas cavity 4154 and the medicament cavity 4157 from the electronic circuit system cavity 4153. In other embodiments the gas cavity 4154 can be fluidically and/or physically isolated from the medicament cavity 4157.

Figure 6:
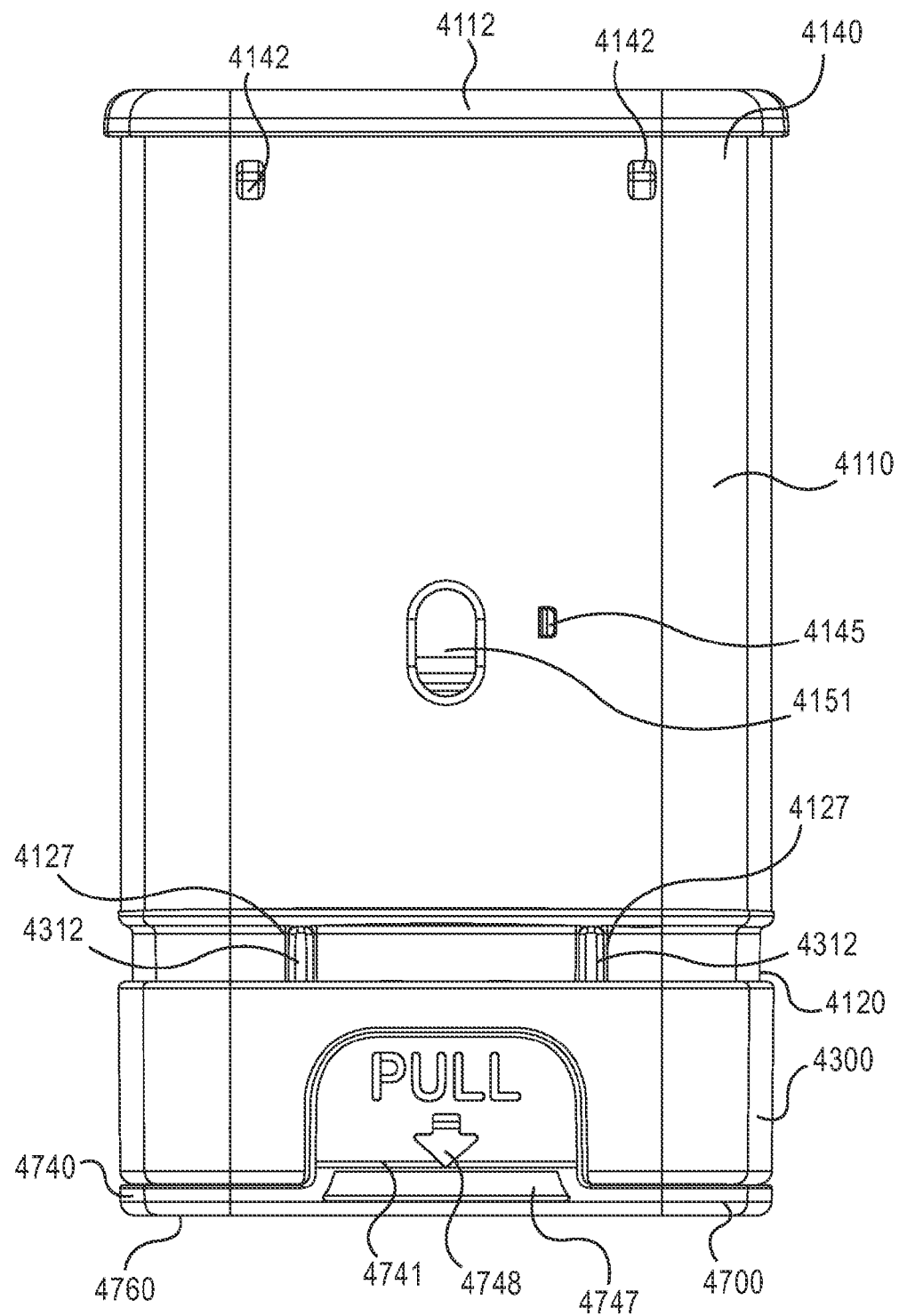
FIG. 6 is a back view of the medical injector illustrated in FIG. 3 with the cover removed.

The proximal end portion 4140 of the housing 4110 includes a proximal cap 4112, a speaker protrusion 4147 (see e.g., FIGS. 8 and 9), and cover retention protrusions 4142 (see e.g., FIGS. 4 and 6). The speaker protrusion 4147 is configured to maintain a position of an audio output device 4956 of the electronic circuit system 4900 relative to the housing 4110 when the electronic circuit system 4900 is attached to the housing 4110, as described herein. Cover retention protrusions 4142 are configured to be received within corresponding openings 4215 on the cover 4200. In this manner, as described in more detail herein, the cover 4200 can be removably coupled to and disposed about at least a portion of the housing 4110.

Figure 11:
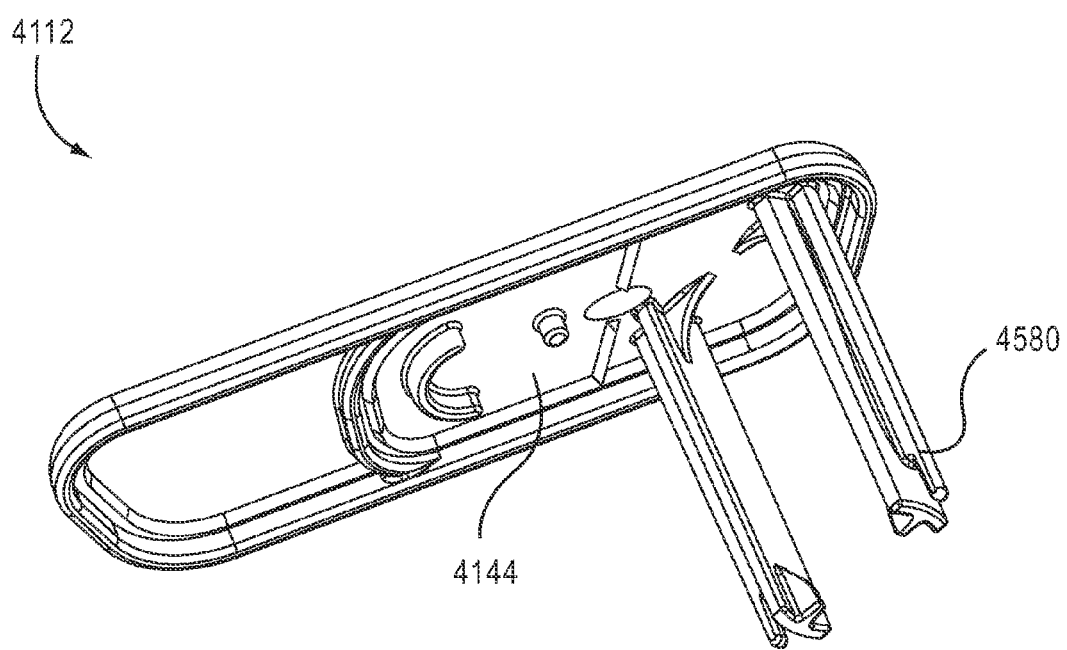
FIG. 11 is a perspective view of a proximal cap of the medical injector illustrated in FIG. 3.

As shown in FIG. 11, the proximal cap 4112 includes a gas container retention member 4580 and defines a gas passageway 4144. The gas container retention member 4580 is configured to receive and/or retain a gas container 4570 that can contain a pressurized gas. The gas passageway 4144 is configured to allow for the passage of gas contained in the gas container 4570 from the gas cavity 4154 to the medicament cavity 4157, as further described herein. Said another way, the gas passageway 4144 places the gas cavity 4154 in fluid communication with the medicament cavity 4157.

Figure 7:
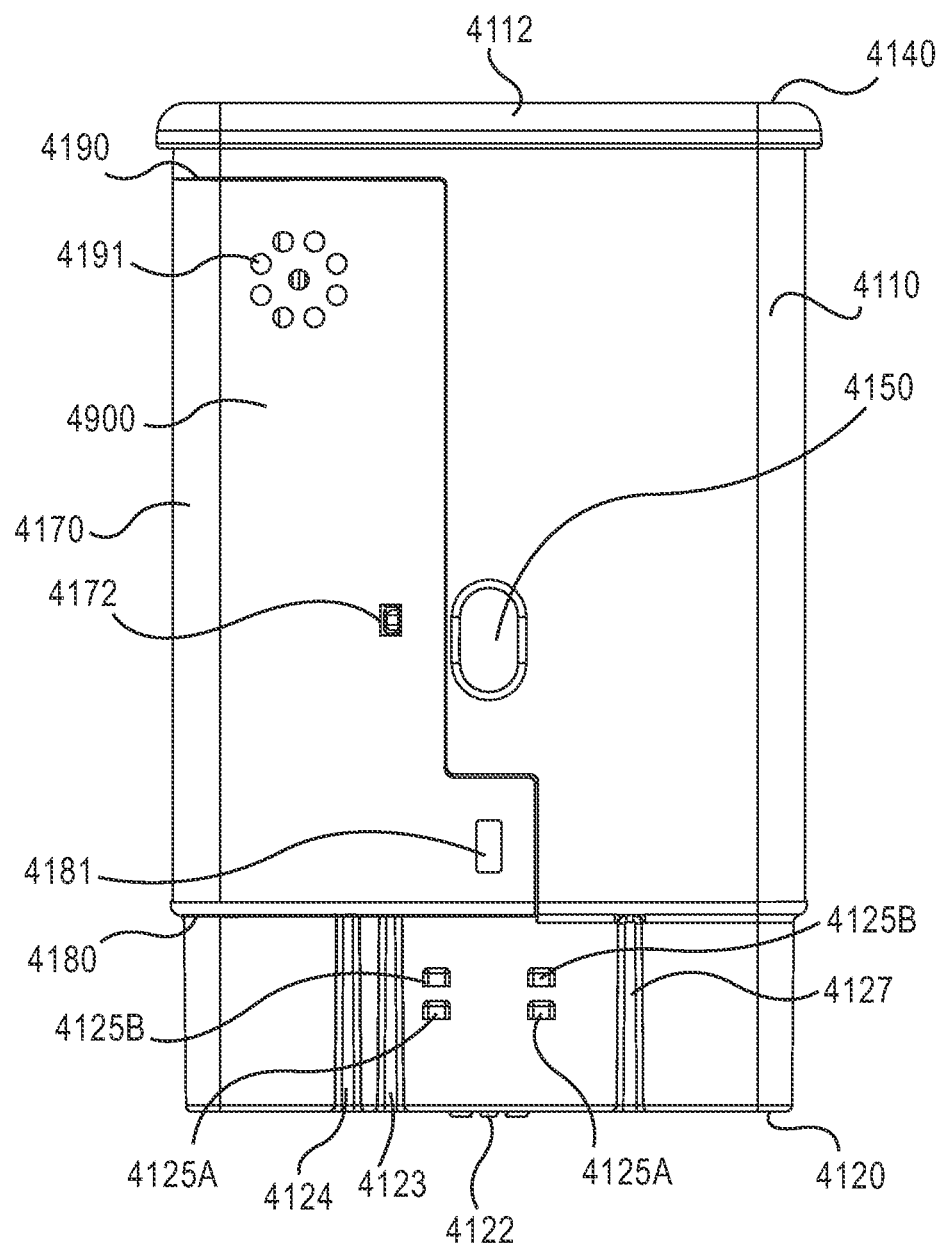
FIG. 7 is a front view of a portion of the medical injector illustrated in FIG. 3.
Figure 8:
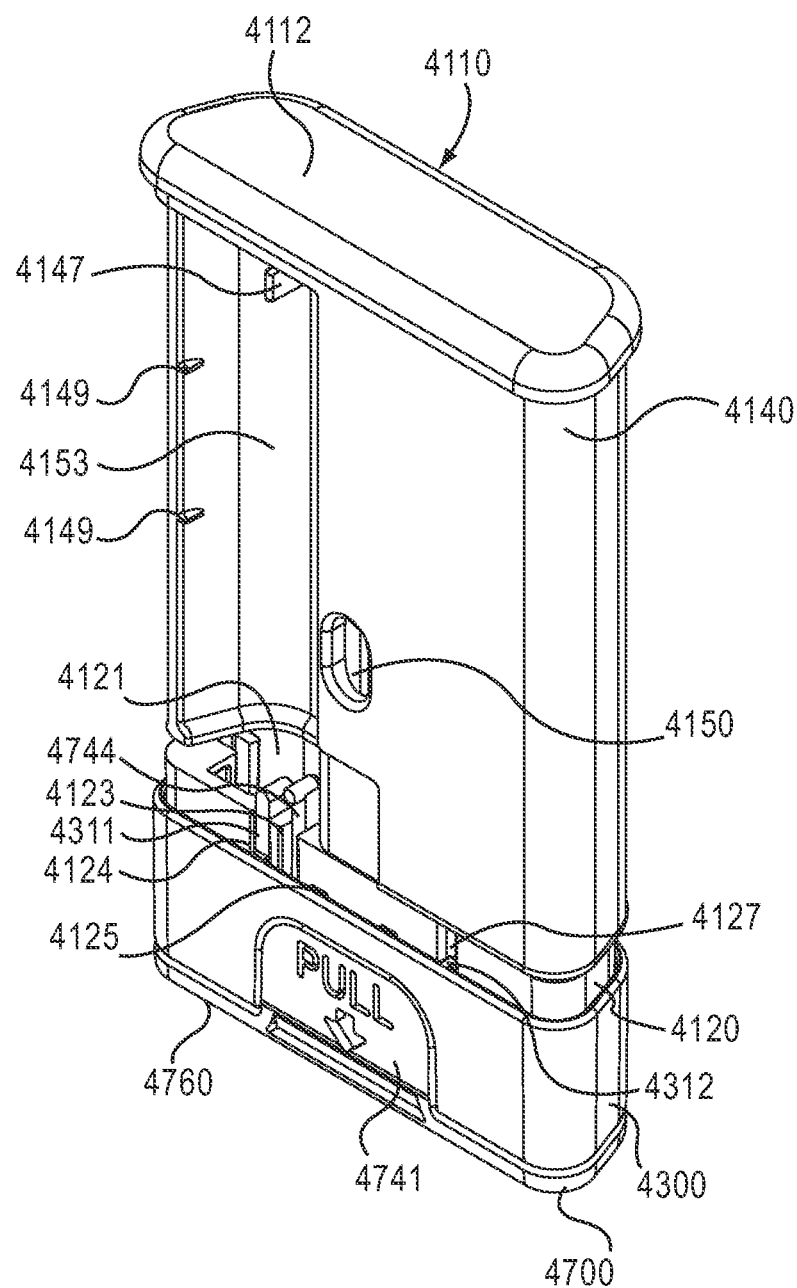
FIG. 8 is a perspective view of a portion of the medical injector illustrated in FIG. 3.

As shown in FIGS. 7 and 9, the distal end portion 4120 of the housing 4110 defines a battery isolation protrusion aperture 4121, a needle aperture 4122, a safety lock actuator groove 4123, a safety lock aperture 4128, a base actuator groove 4124, base retention recesses 4125A, 4125B, and base rail grooves 4127. The battery isolation protrusion aperture 4121 is configured to receive the battery isolation protrusion 4235 of the cover 4200 (see e.g., FIG. 25), as described in further detail herein.

The needle aperture 4122 is configured to allow the needle 4512 (see e.g., FIG. 12) to exit the housing 4110 when the medical injector 4000 is actuated. The portion of the sidewall of the housing 4110 that defines the needle aperture 4122 includes multiple sheath retention protrusions 4126. In some embodiments, the sheath retention protrusions can interact with the a plurality of ribs 4728 of the needle sheath 4720 (see e.g. FIG. 29) to maintain a position of the needle sheath 4720 relative to the safety lock 4700 when the safety lock 4700 is coupled to the housing 4110 and/or when the safety lock 4700 is being removed from the housing 4110.

The safety lock actuator groove 4123 is configured to receive an actuator 4744 of the safety lock 4700. As described in more detail herein, the actuator 4744 is configured to engage and/or activate the electronic circuit system 4900 when the safety lock 4700 is moved with respect to the housing 4110. The safety lock aperture 4128 is configured to receive a safety lock protrusion 4742 (see e.g., FIGS. 25 and 26). As described in more detail below, the safety lock protrusion 4742 is received within an opening 4554 between extensions 4552 of a release member 4540 such that activation of the medical injector 4000 is prevented when the safety lock 4700 is in place. The safety lock 4700, its components and functions are further described herein.

The distal base retention recesses 4125A are configured to receive the base connection knobs 4358 of the base 4300 (see e.g., FIG. 30) when the base 4300 is in a first position relative to the housing 4110. The proximal base retention recesses 4125B are configured to receive the base connection knobs 4358 of the base 4300 when the base 4300 is in a second position relative to the housing 4110. The base retention recesses 4125A, 4125B have a tapered proximal sidewall and a non-tapered distal sidewall. This allows the base retention recesses 4125A, 4125B to receive the base connection knobs 4358 such that the base 4300 can move proximally relative to the housing 4110, but cannot move distally relative to the housing 4110. Said another way, the distal base retention recesses 4125A are configured to prevent the base 4300 from moving distally when the base 4300 is in a first position and the proximal base retention recesses 4125B are configured to prevent the base 4300 from moving distally when the base 4300 is in a second position. Similarly stated, the proximal base retention recesses 4125B and the base connection knobs 4358 cooperatively prevent "kickback" after the medical injector 4000 is actuated.

The base actuator groove 4124 is configured to receive an actuator 4311 of the base 4300. As described in more detail herein, the actuator 4311 of the base 4300 is configured to engage the electronic circuit system 4900 when the base 4100 is moved with respect to the housing 4110. The base rail grooves 4127 are configured to receive the guide members 4312 of the base 4300. The guide members 4312 of the base 4300 and the base rail grooves 4127 of the housing 4110 engage each other in a way that allows the guide members 4312 of the base 4300 to slide in a proximal and/or distal direction within the base rail grooves 4127 while limiting lateral movement of the guide members 4312. This arrangement allows the base 4300 to move in a proximal and/or distal direction with respect to the housing 4110 but prevents the base 4300 from moving in a lateral direction with respect to the housing 4110.

Figure 12:
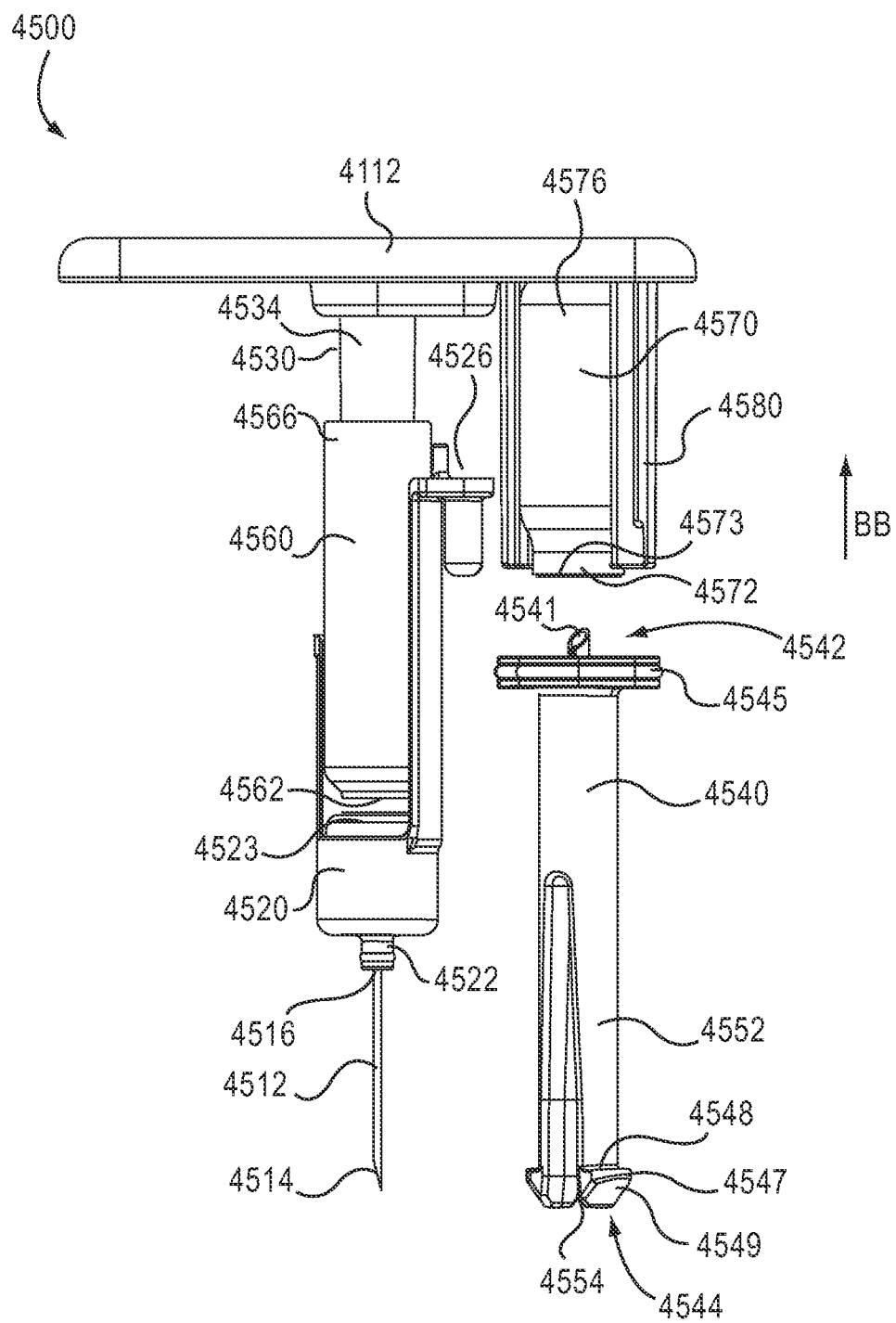
FIG. 12 is a front view of a medicament delivery mechanism of the medical injector illustrated in FIG. 3.
Figure 13:
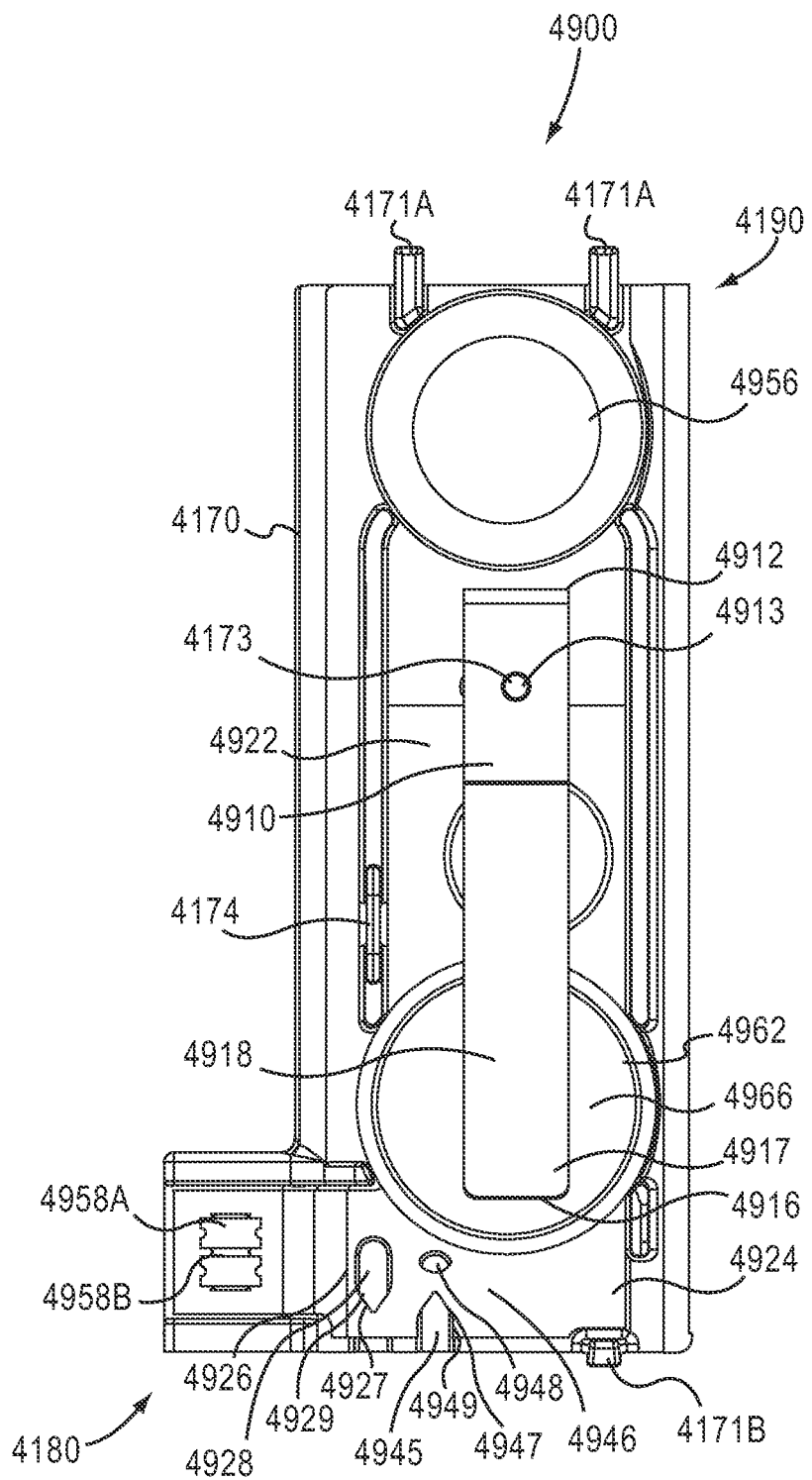
FIG. 13 is a back view of an electronic circuit system of the medical injector illustrated in FIG. 3.
Figure 14:
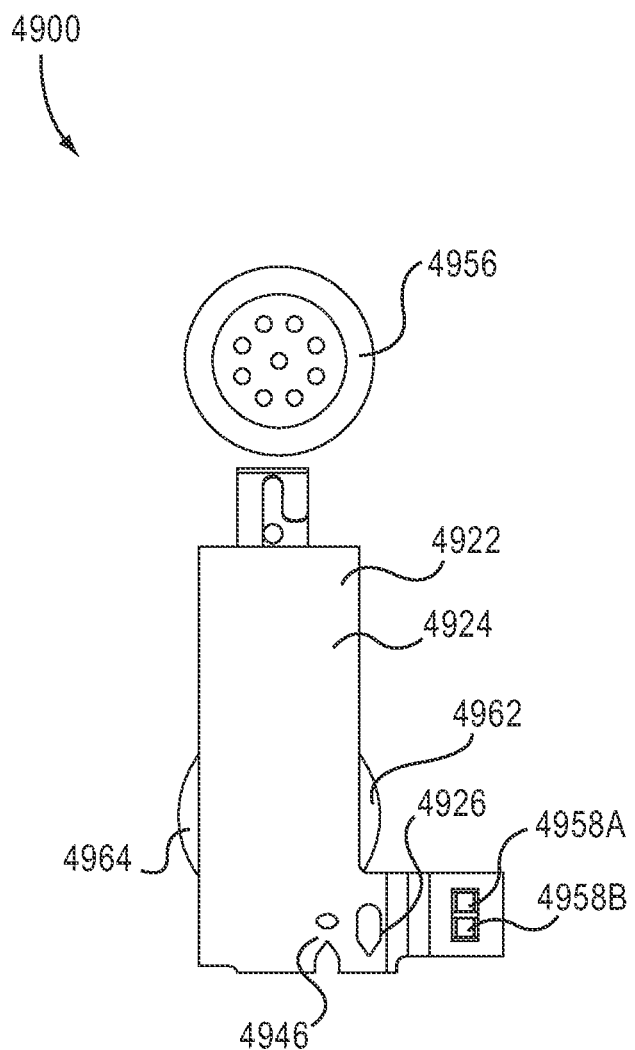
FIG. 14 is a front view of a portion of the electronic circuit system of the medical injector illustrated in FIG. 13.
Figure 15:
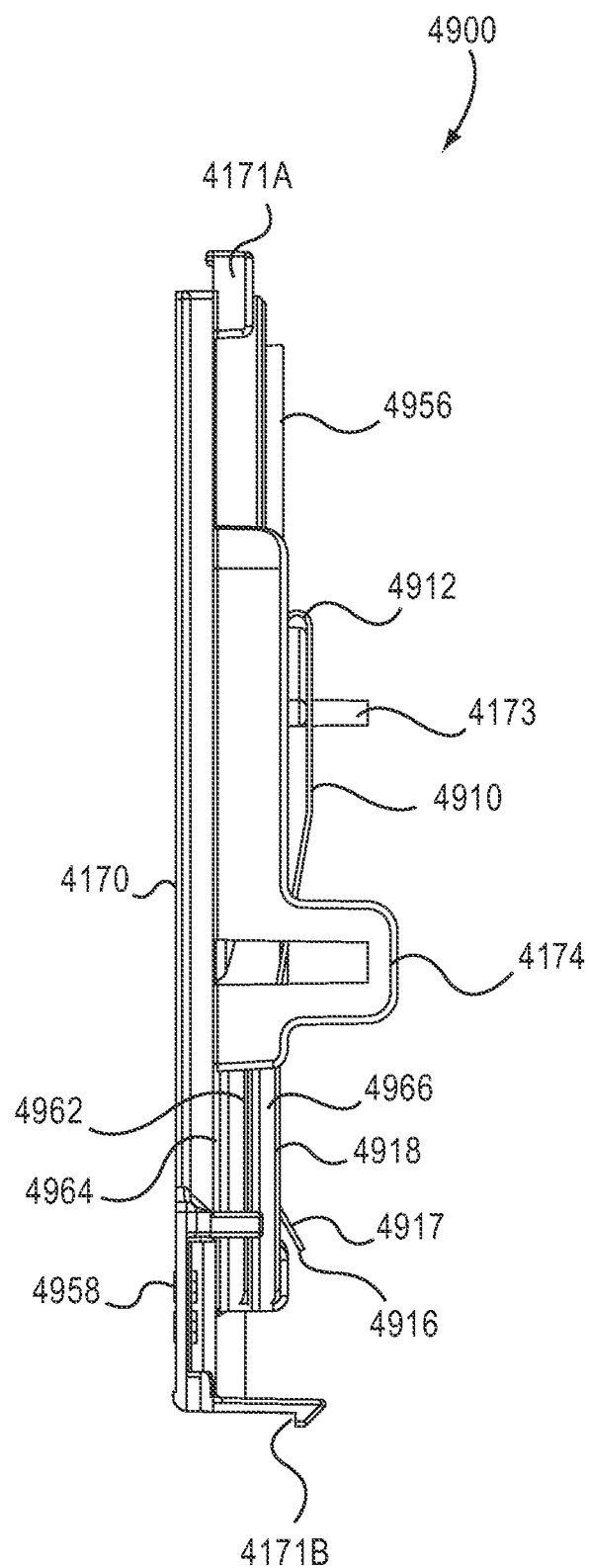
FIG. 15 is a side view of the electronic circuit system of the medical injector illustrated in FIG. 13.

FIG. 12 shows the medicament delivery mechanism 4500 of the medical injector 4000. The medical injector 4000 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, only an overview of the medicament delivery mechanism 4500 and related operation of the medical injector 4000 is included below.

The medicament delivery mechanism 4500 includes a needle 4512, a carrier 4520, a movable member 4530, a medicament container 4560, a gas container 4570, and a release member 4540. As described above, the needle 4512, carrier 4520, movable member 4530 and medicament container 4560 are disposed within the medicament cavity 4157 of the housing 4110. The gas container 4570 and the release member 4540 are disposed within the gas cavity 4154 of the housing 4110.

The release member 4540 has a proximal end portion 4542 and a distal end portion 4544, and is movably disposed within the distal end portion 4156 of the gas cavity 4154. The proximal end portion 4542 of the release member 4540 includes a sealing member 4545 and a puncturer 4541. The sealing member 4545 is configured to engage the sidewall of the housing 4110 defining the gas cavity 4154 such that the proximal end portion 4155 of the gas cavity 4154 is fluidically isolated from the distal end portion 4156 of the gas cavity 4154. In this manner, when gas is released from the gas container 4570, the gas contained in the proximal end portion 4155 of the gas cavity 4154 is unable to enter the distal end portion 4156 of the gas cavity 4154. The puncturer 4541 of the proximal end portion 4542 of the release member 4540 is configured to contact and puncture a frangible seal 4573 on the gas container 4570 when the release member 4540 moves proximally within the gas cavity 4154, as shown by the arrow BB in FIG. 12.

The distal end portion 4544 of the release member 4540 includes extensions 4552. The extensions 4552 include projections 4547 that include tapered surfaces 4549 and engagement surfaces 4548. Further, the extensions 4552 define an opening 4554 between the extensions 4552. The tapered surfaces 4549 of the projections 4547 are configured to contact protrusions 4313 on a proximal surface 4310 of the base 4300 (see e.g., FIG. 30). The engagement surfaces 4548 of the projections 4547 are configured to extend through the safety lock aperture 4128 of the housing 4110 and contact a distal surface of the housing 4110. In this manner, the engagement surfaces 4548 of the projections 4547 limit proximal movement of the release member 4540 when the engagement surfaces 4548 are in contact with the distal surface of the housing 4110.

Figure 27:
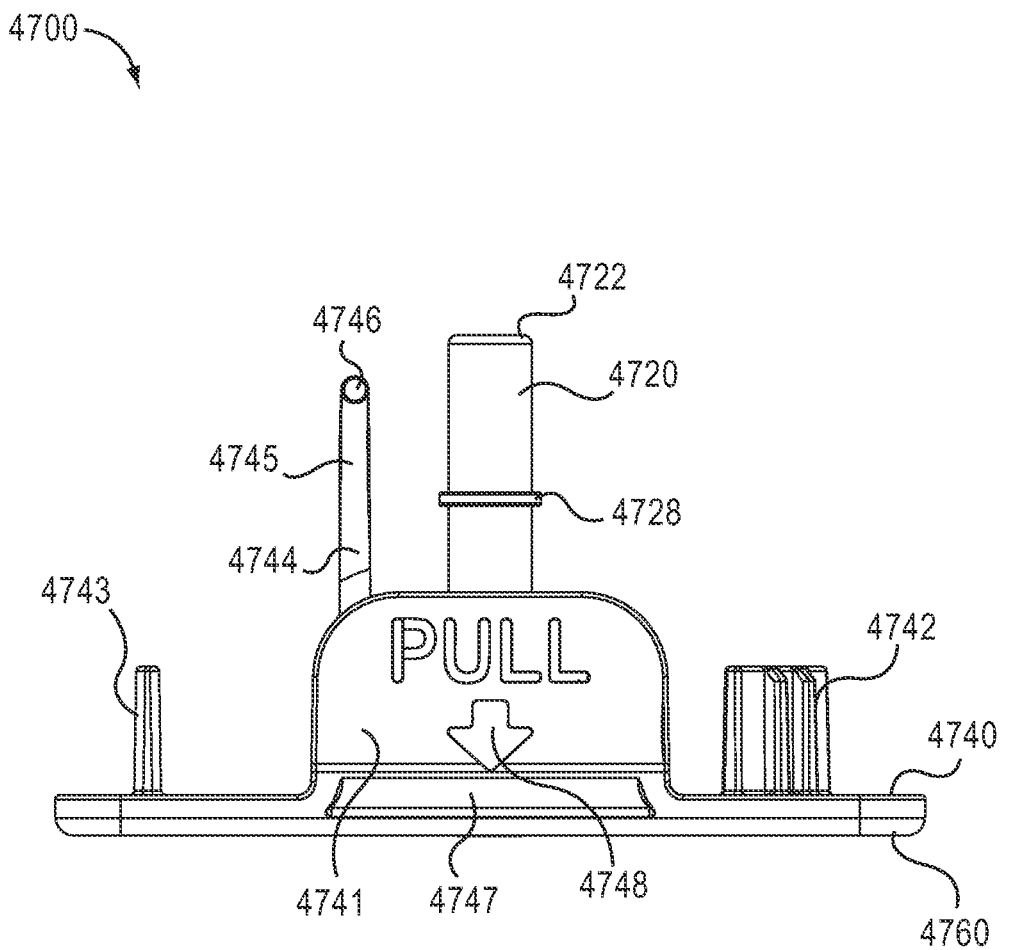
FIG. 27 is a front view of the safety lock of the medical injector illustrated in FIG. 26.

The opening 4554 defined by the extensions 4552 is configured to receive the safety lock protrusion 4742 of the safety lock 4700 (see e.g., FIG. 27). The safety lock protrusion 4742 is configured to prevent the extensions 4552 from moving closer to each other. Said another way, the safety lock protrusion 4742 is configured to ensure that the extensions 4552 remain apart and the engagement surfaces 4548 of the projections 4547 remain in contact with the distal end portion 4120 of the housing 4110. In some embodiments, for example, the release member 4540 and/or the extensions 4552 can be constructed from any suitable material configured to withstand deformation that may occur when exposed to a load over an extended period of time. In some embodiments, for example, the release member 4540 and/or the extensions 4552 can be constructed from brass.

The gas container 4570 includes a distal end portion 4572 and a proximal end portion 4576, and is configured to contain a pressurized gas. The distal end portion 4572 of the gas container 4570 contains a frangible seal 4573 configured to break when the puncturer 4541 of the proximal end portion 4542 of the release member 4540 contacts the frangible seal 4573. The gas container retention member 4580 of the proximal cap 4112 of the housing 4110 is configured to receive and/or retain the proximal end portion 4576 of the gas container 4570. Said another way, the position of the gas container 4570 within the gas cavity 4154 is maintained by the gas container retention member 4580.

The medicament container 4560 of the medicament delivery mechanism 4500 has a distal end portion 4562 and a proximal end portion 4566, and is configured to contain a medicament. The distal end portion 4562 of the medicament container 4560 contains a seal 4523. The seal 4523 is configured to burst when punctured by the proximal end 4516 of the needle 4512, as described below. The proximal end portion 4566 of the medicament container 4560 is configured to receive a piston portion 4534 of the movable member 4530.

The movable member 4530 of the medicament delivery mechanism 4500 is movably disposed within the medicament cavity 4157. The movable member 4530 includes a piston portion 4534 having a plunger at the distal end portion of the piston portion 4534. The piston portion 4534 is configured to move within the medicament container 4560. In this manner, the piston portion 4534 of the movable member 4530 can apply pressure to a medicament contained in the medicament container 4560. The piston portion 4534 can be constructed of a resilient, durable, and/or sealing material, such as a rubber.

The carrier 4520 of the medicament delivery mechanism 4500 includes a distal end portion 4522 and a proximal end portion 4526. The medicament container 4560 is coupled to the carrier 4520 via a "snap-fit" connection (not shown) such that the medicament container 4560 can move relative to the carrier 4520 between a first configuration and a second configuration during an injection event. In the first configuration, the carrier 4520 is configured to move within the medicament cavity 4157 such that movement of the carrier 4520 within the medicament cavity 4157 causes contemporaneous movement of the medicament container 4560 within the medicament cavity 4157. The proximal end portion 4516 of the needle 4512 is spaced apart from the seal 4523 of the medicament container 4560 when the carrier 4520 is in the first configuration. In the second configuration, the medicament container 4560 releases from the "snap-fit" causing the medicament container 4560 to move distally with respect to the carrier 4520, causing the proximal end portion 4516 of the needle 4512 to pierce the seal 4523. In this manner, the needle 4512 can be selectively placed in fluid communication with the medicament container 4560 to define a medicament delivery path (not shown).

Figure 20:
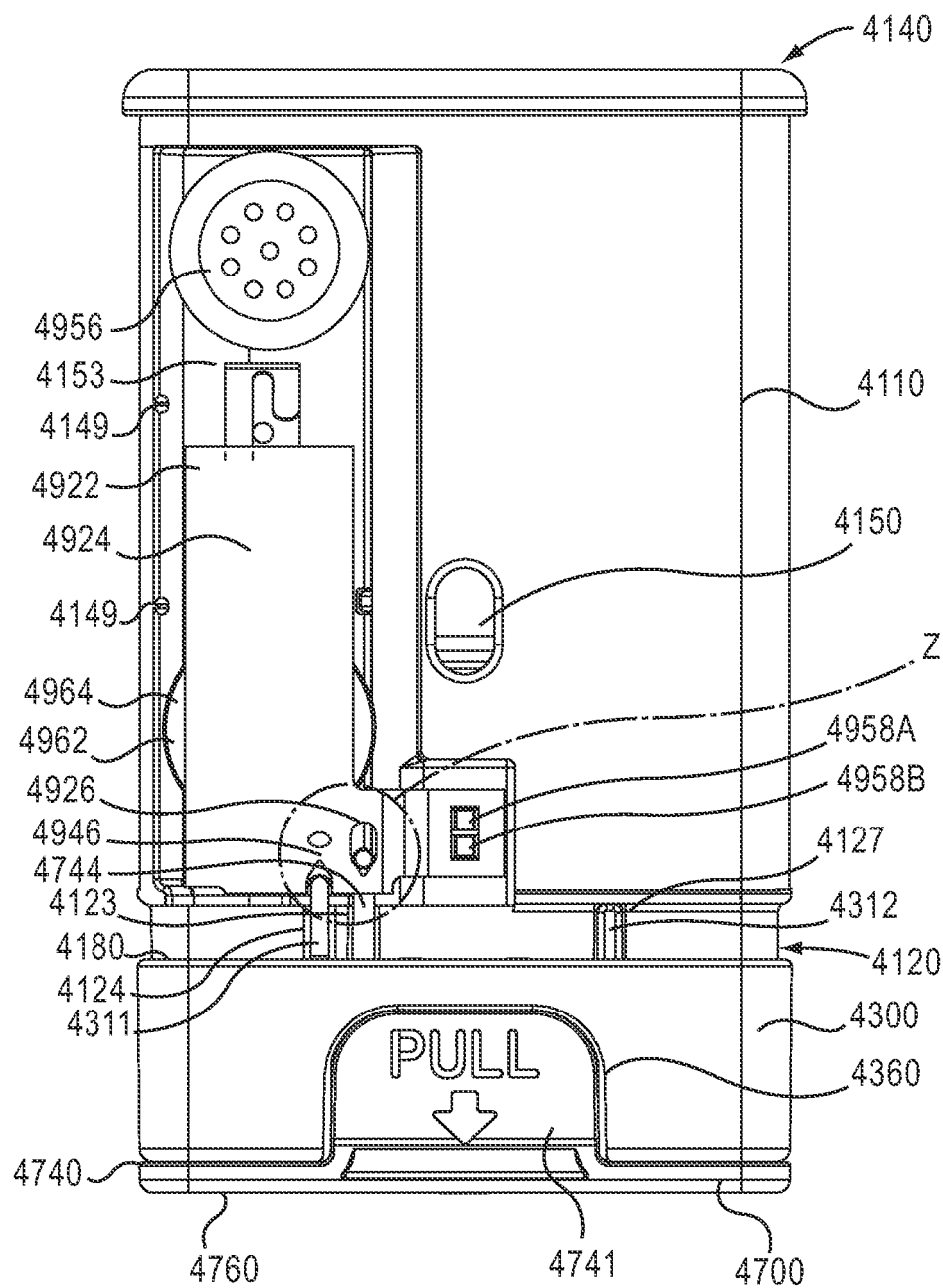
FIG. 20 is a front view of the medical injector illustrated in FIG. 3 in a first configuration showing the electronic circuit system.

FIGS. 13-22 show the electronic circuit system 4900. The electronic circuit system 4900 of the medical injector 4000 includes an electronic circuit system housing 4170, a printed circuit board 4922, a battery assembly 4962, an audio output device 4956, two light emitting diodes (LEDs) 4958A, 4958B and a battery clip 4910. As shown in FIG. 20, the electronic circuit system 4900 is configured to fit within the electronic circuit system cavity 4153 of the housing 4110. Accordingly, as described above, the electronic circuit system 4900 is physically and/or fluidically isolated from the medicament cavity 4157, the gas cavity 4154 and/or the medicament delivery device 4500. As described herein, the electronic circuit system 4900 is configured to output an electronic output associated with the use of the medical injector 4000.

The electronic circuit system housing 4170 of the electronic circuit system 4900 includes a distal end portion 4180 and a proximal end portion 4190. The proximal end portion 4190 includes connection protrusions 4171A and a battery clip protrusion 4173. The connection protrusions 4171A extend from the proximal end portion 4190 of the electronic circuit system housing 4170, and are configured to be disposed within the connection apertures 4152 of the housing 4110, as described above. In this manner, the electronic circuit system 4900 can be coupled to the housing 4110 within the electronic circuit system cavity 4153. In other embodiments, the electronic circuit system 4900 can be coupled to the housing 4110 by other suitable means such as an adhesive, a clip and/or the like. As described in more detail herein, the battery clip protrusion 4173 is configured to hold the battery clip 4910 in place.

The proximal end portion 4190 of the electronic circuit system housing 4170 defines multiple sound apertures 4191. The audible output device 4956 is disposed against the proximal end portion 4190 of the electronic circuit system housing 4170 such that the front face of the audible output device 4956 is disposed adjacent the sound apertures 4191. In this manner, the sound apertures 4191 are configured to allow sound from an audio output device 4956 to pass from the audio output device 4956 to a region outside of the housing 4110.

Figure 16:
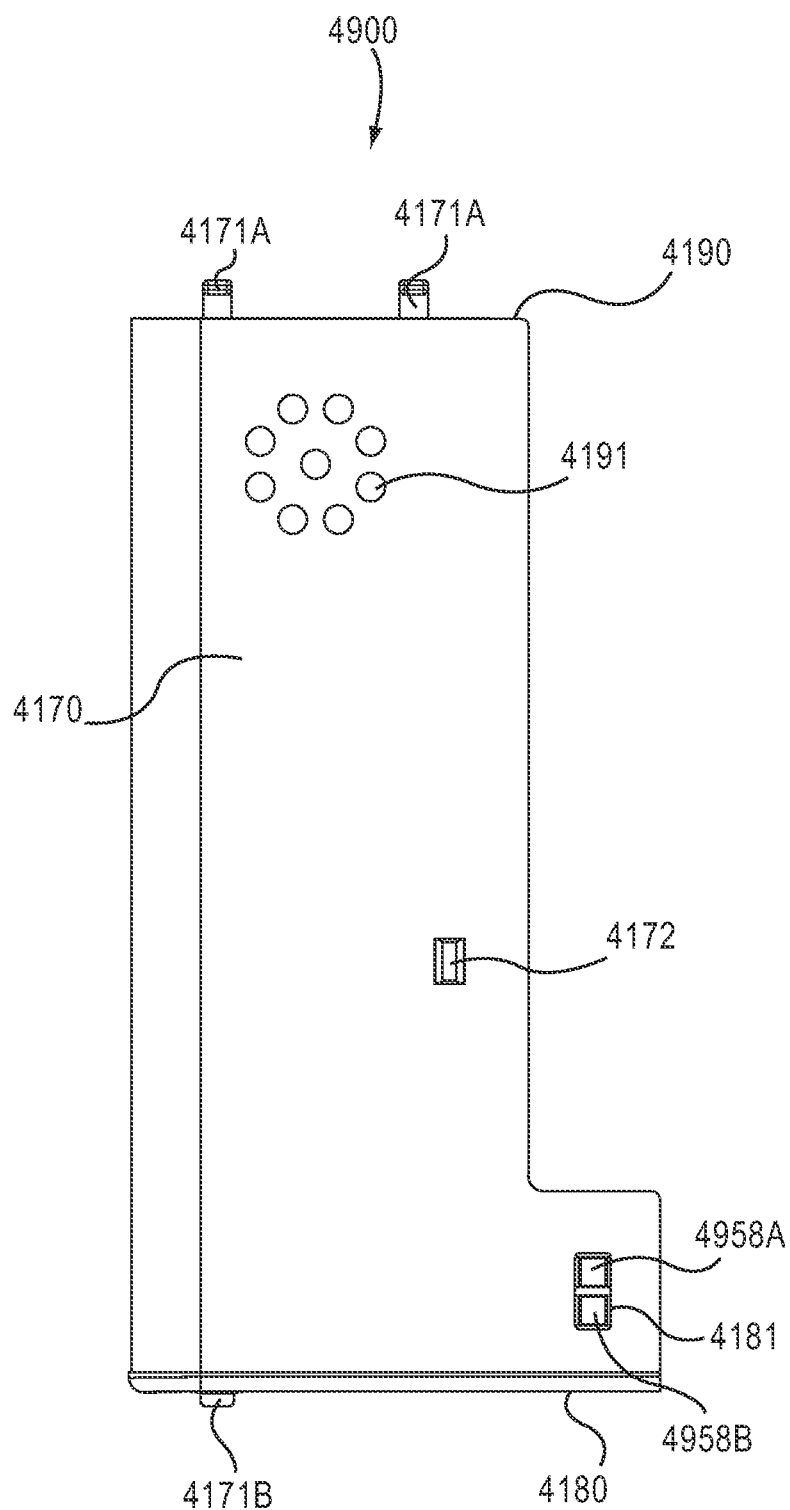
FIG. 16 is a front view of an electronic circuit system housing of the medical injector illustrated in FIG. 13.
Figure 17:
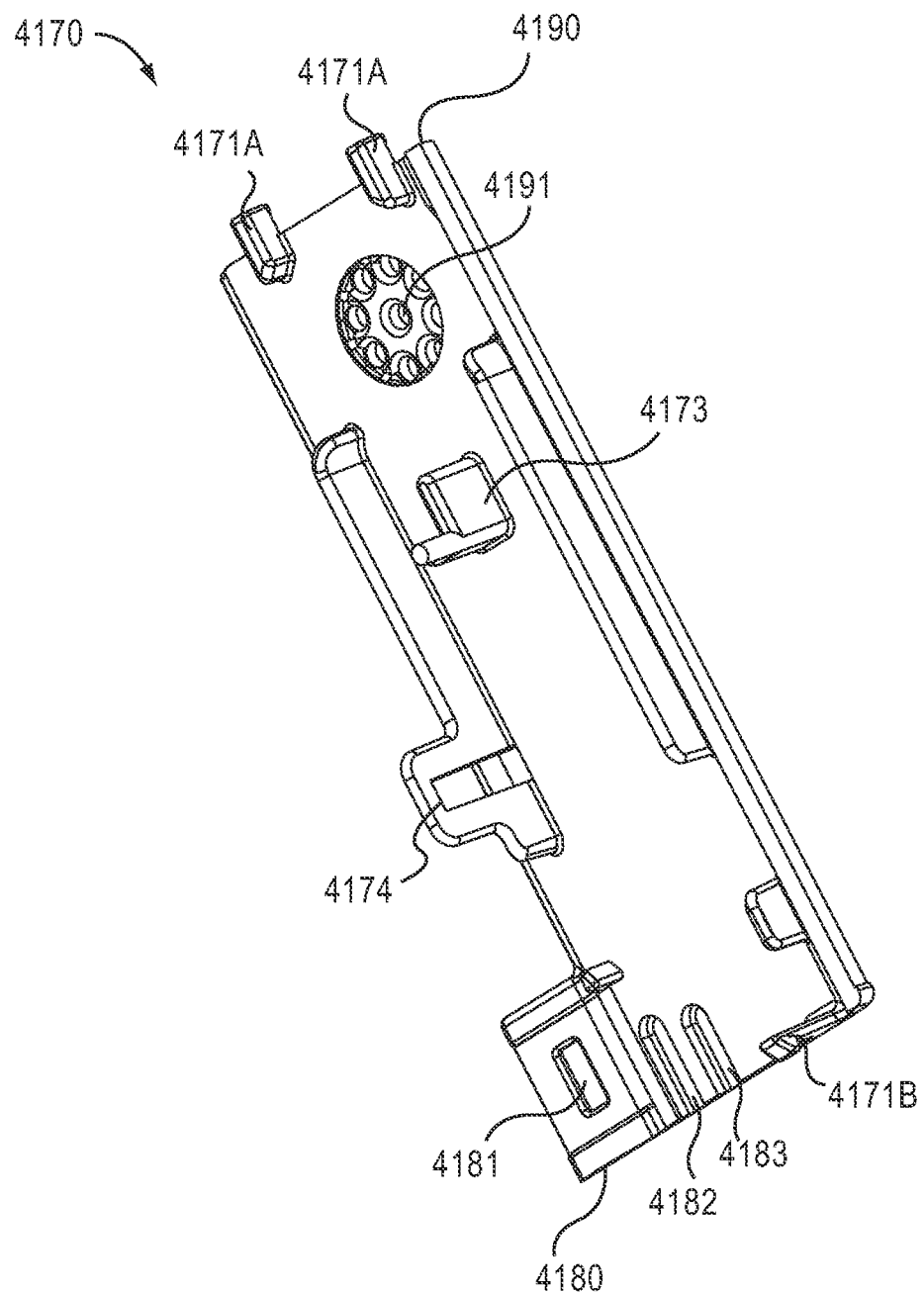
FIG. 17 is a perspective view of the electronic circuit system housing of the medical injector illustrated in FIG. 16.
Figure 18:
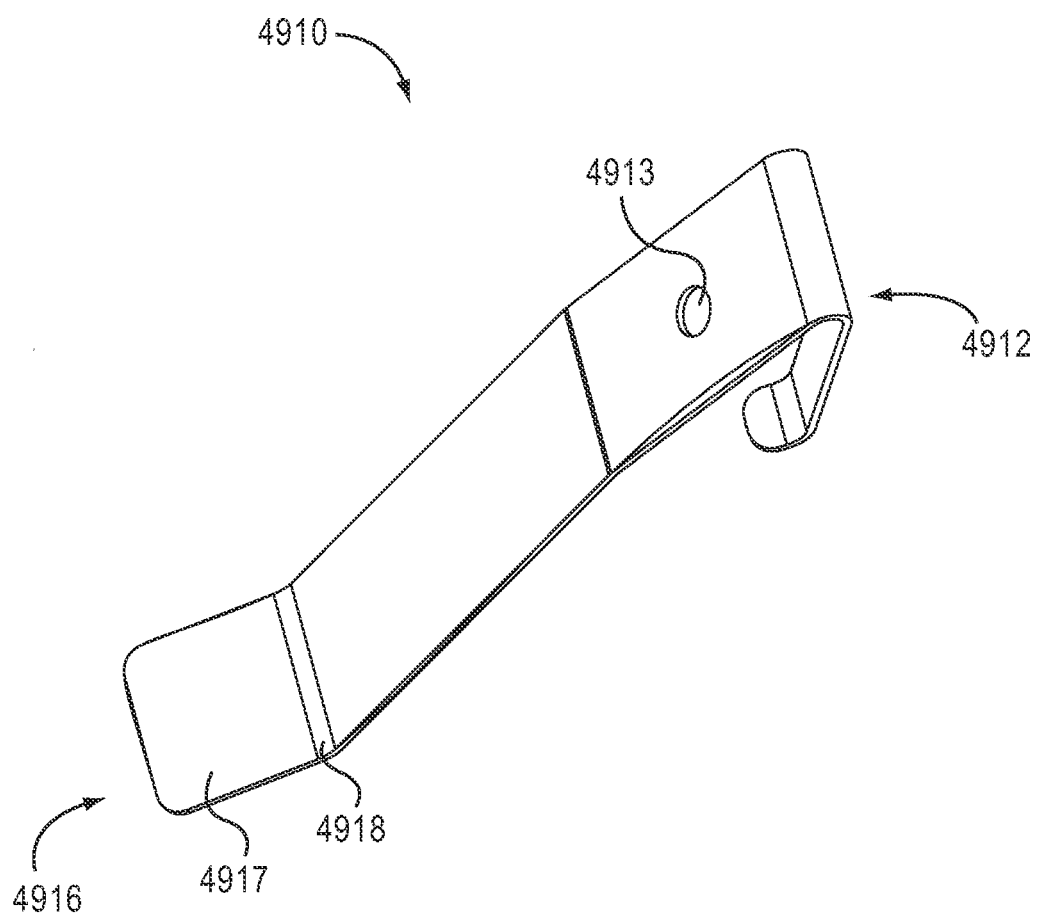
FIG. 18 is a perspective view of a battery clip of the medical injector illustrated in FIG. 13.
Figure 19:
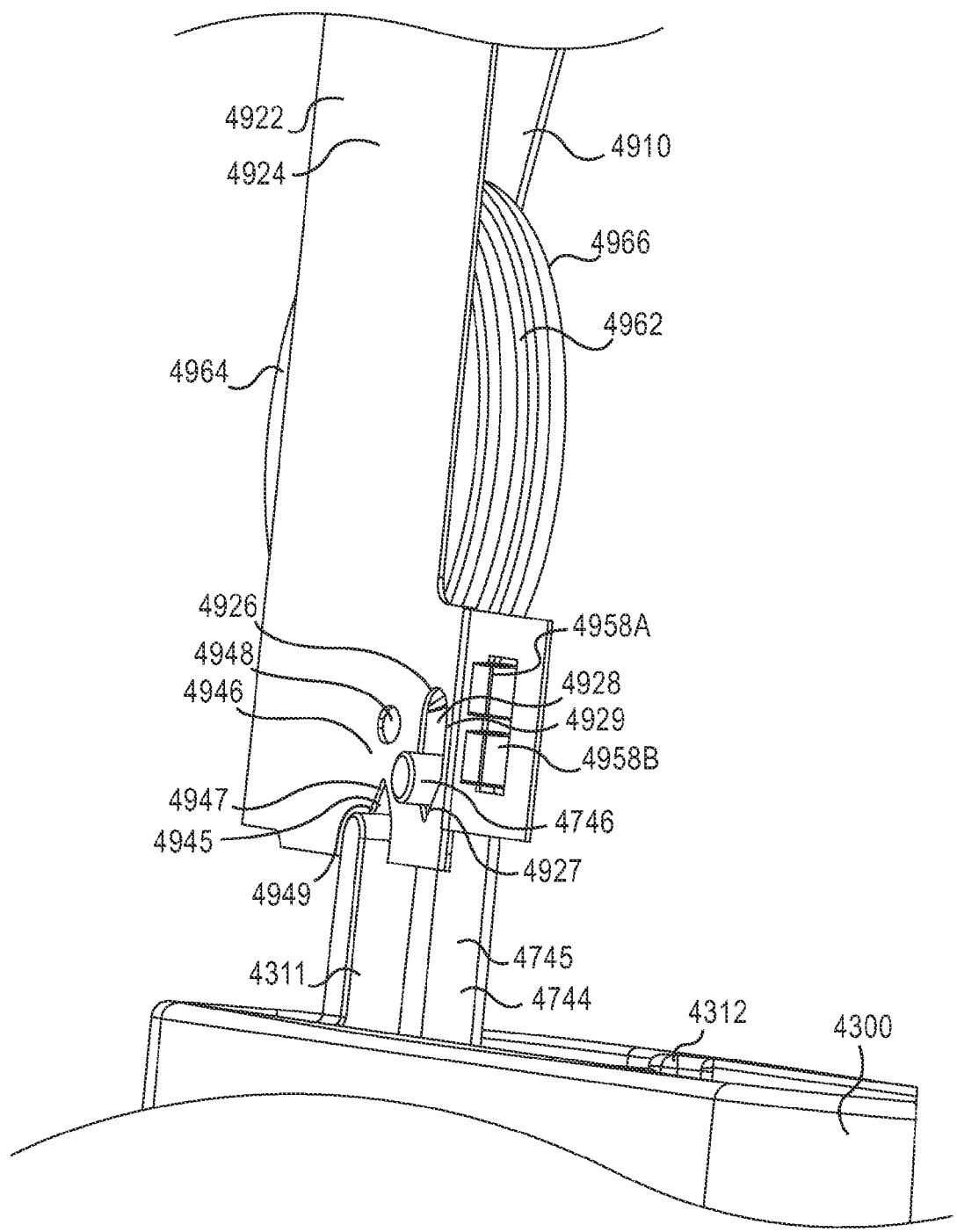
FIG. 19 is a perspective view of a portion of an electronic circuit system of the medical injector illustrated in FIG. 3, in a first configuration.

As shown in FIGS. 16 and 17, the distal end portion 4180 of the electronic circuit system housing 4170 includes a connection protrusion 4171B, a stiffening protrusion 4174, and defines an LED aperture 4181, an aperture 4172, a safety lock actuator groove 4182, and a base actuator groove 4183. The LED aperture 4181 is configured to receive the LEDs 4958A, 4958B such that a user can view the LEDs 4958A, 4958B, which are described in more detail herein.

The connection protrusion 4171B extends from the distal end portion 4180 of the electronic circuit system housing 4170, and is configured to attach the electronic circuit system 4900 to the housing 4110, as described above. The stiffening protrusion 4174 is configured to have at least a portion received within and/or accessible via the aperture 4145 in the housing 4110 (see e.g., FIG. 6). The stiffening protrusion 4174 is configured to limit the bending (e.g., buckling) of the electronic circuit system housing 4170 when the electronic circuit system housing 4170 is coupled to the housing 4110. Moreover, a user can access the stiffening protrusion 4174 via the aperture 4172. In this manner, for example, the user can disengage the stiffening protrusion 4174 from the aperture 4145.

The safety lock actuator groove 4182 of the electronic circuit system housing 4170 is configured to be disposed adjacent the safety lock actuator groove 4123 of the distal end portion 4120 of the housing 4110. In this manner, the safety lock actuator groove 4182 of the electronic circuit system housing 4170 and the safety lock actuator groove 4123 of the distal end portion 4120 of the housing 4110 collectively receive the actuator 4744 of the safety lock 4700, which is described in more detail herein. Similarly, the base actuator groove 4183 of the electronic circuit system housing 4170 is configured to be disposed about the base actuator groove 4124 of the distal end portion 4120 of the housing 4110. The base actuator groove 4183 of the electronic circuit system housing 4170 and the base actuator groove 4124 of the distal end portion 4120 of the housing 4110 collectively receive the actuator 4311 of the base 4300, which is described in more detail herein.

The printed circuit board 4922 of the electronic circuit system 4900 includes a substrate 4924, a first actuation portion 4926 and a second actuation portion 4946. The substrate 4924 of the printed circuit board 4922 includes the electrical components necessary for the electronic circuit system 4900 to operate as desired. For example, the electrical components can be resistors, capacitors, inductors, switches, microcontrollers, microprocessors and/or the like.

Figure 21:
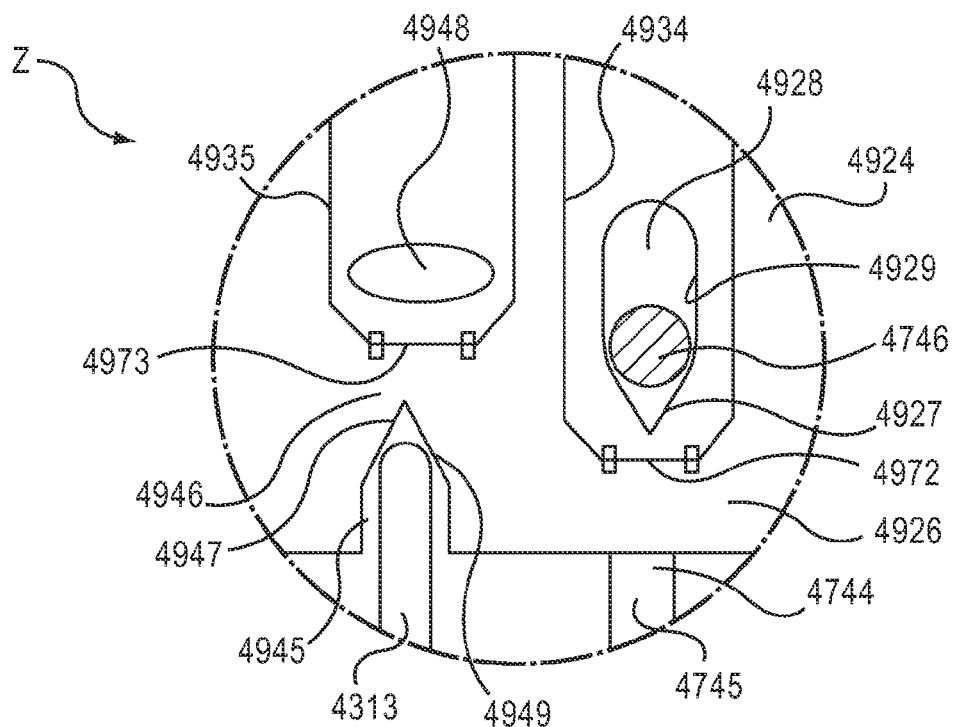
FIGS. 21, 22, and 23 are front views of a portion of the electronic circuit system of the medical injector labeled as Region Z in FIG. 20 in a first configuration, a second configuration, and a third configuration, respectively.
Figure 22:
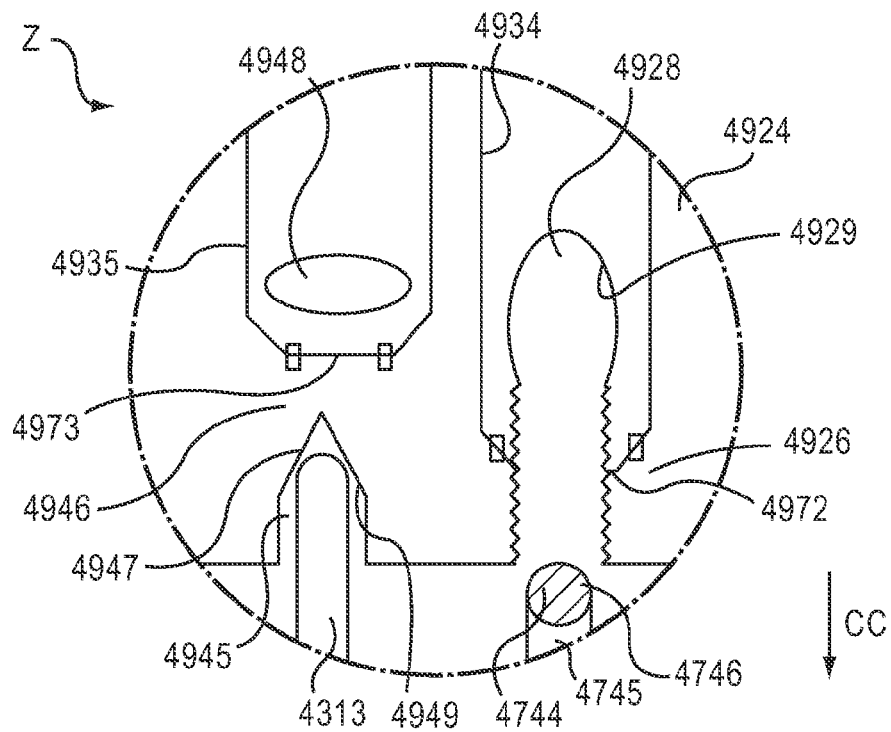
Figure 23:
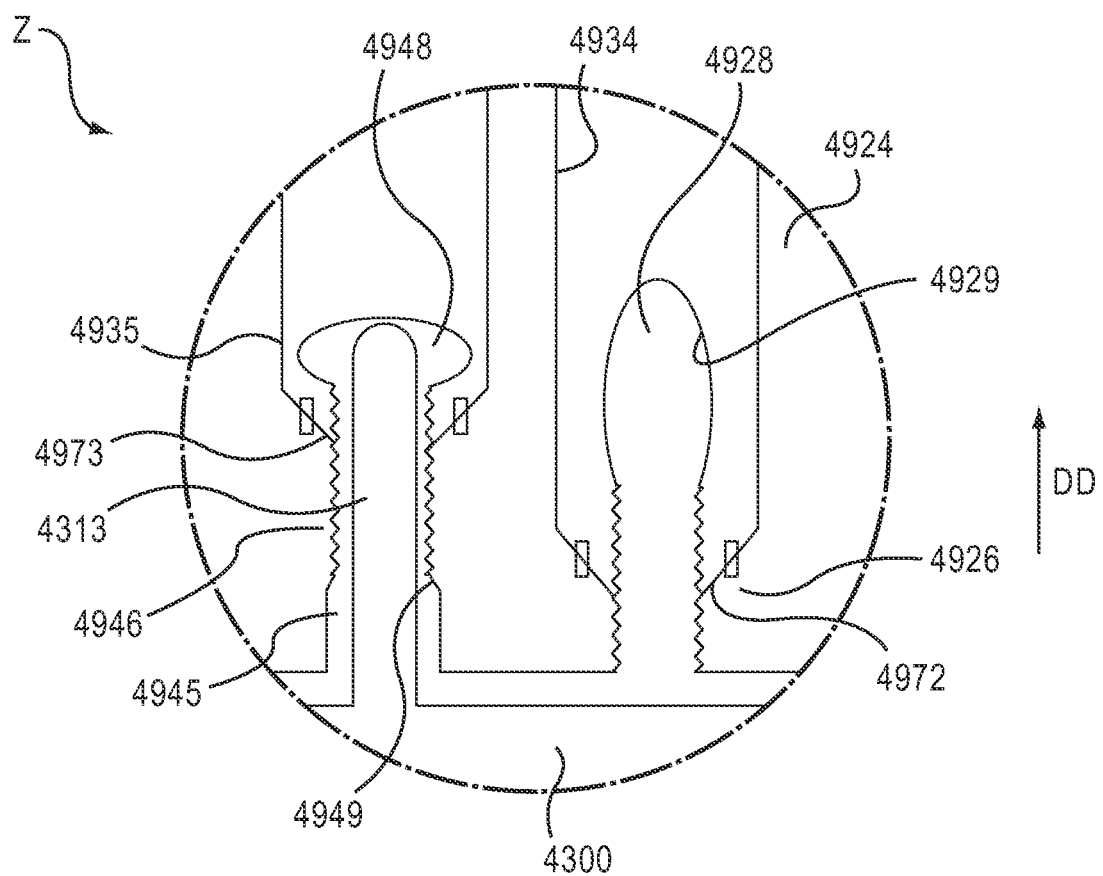

As shown in FIGS. 21-23, the first actuation portion 4926 includes a first electrical conductor 4934 and defines an opening 4928 having a boundary 4929. The opening 4928 of the first actuation portion 4926 is configured to receive a protrusion 4746 of the actuator 4744 of the safety lock 4700. The boundary 4929 of the first opening 4928 has a discontinuous shape, such as, for example, a teardrop shape, that includes a stress concentration riser 4927. The discontinuity and/or the stress concentration riser 4927 of the boundary 4929 can be of any suitable shape to cause the substrate 4924 to deform in a predetermined direction when the protrusion 4746 of the actuator 4744 of the safety lock 4700 is moved relative to the opening 4928, as shown by the arrow CC in FIG. 22.

The opening 4928 is defined adjacent the first electrical conductor 4934 that electronically couples the components included in the electronic circuit system 4900. The first electrical conductor 4934 includes a first switch 4972, which can be, for example a frangible portion of the first electrical conductor 4934. In use, when the safety lock 4700 is moved from a first position (see e.g., FIG. 21) to a second position (see e.g., FIG. 22), the actuator 4744 moves in a direction substantially parallel to a plane defined by a surface of the first actuation portion 4926 of the substrate 4924. The movement of the actuator 4744 causes the protrusion 4746 to move within the first opening 4928, as indicated by the arrow CC in FIG. 22. The movement of the protrusion 4746 tears the first actuation portion 4926 of the substrate 4924, thereby separating the portion of the first electrical conductor 4934 including the first switch 4972. Said another way, when the safety lock 4700 is moved from its first position to its second position (see e.g., FIG. 33), the actuator 4744 moves irreversibly the first switch 4972 from a first state (e.g., a state of electrical continuity) to a second state (e.g., a state of electrical discontinuity). Said yet another way, when the safety lock 4700 is moved from its first position to its second position, the actuator 4744 disrupts the first electrical conductor 4934.

The second actuation portion 4946 includes a second electrical conductor 4935 and defines an opening 4945, having a boundary 4949 and a tear propagation limit aperture 4948. As shown in FIGS. 20-23, the opening 4945 of the second actuation portion 4946 is configured to receive a portion of an actuator 4311 of the base 4300. The boundary 4949 of the opening 4945 has a discontinuous shape that includes a stress concentration riser 4947. The discontinuity and/or the stress concentration riser 4947 of the boundary 4949 can be of any suitable shape to cause the substrate 4924 to deform in a predetermined direction when the actuator 4311 of the base 4300 is moved in a proximal direction relative to the opening 4945, as shown by the arrow DD in FIG. 23.

The second electrical conductor 4935 includes a second switch 4973 disposed between the opening 4945 and the tear propagation limit aperture 4948, which can be, for example, a frangible portion of the second electrical conductor 4935. In use, when the base 4300 is moved from its first position to its second position (see e.g., FIG. 34), the actuator 4311 moves in a proximal direction, substantially parallel to a plane defined by a surface of the second actuation portion 4946 of the substrate 4924. The proximal movement of the actuator 4311 tears the second actuation portion 4946 of the substrate 4924, thereby separating the portion of the second electrical conductor 4935 including the second switch 4973. Said another way, when the base 4300 is moved from its first position to its second position, the actuator 4311 moves irreversibly the second switch 4973 from a first state (e.g., a state of electrical continuity) to a second state (e.g., a state of electrical discontinuity). The tear propagation limit aperture 4948 is configured to limit the propagation of the tear in the substrate 4924 in the proximal direction. Said another way, the tear propagation limit aperture 4948 is configured to ensure that the tear in the substrate 4924 does not extend beyond the tear propagation limit aperture 4948. The tear propagation limit aperture 4948 can be any shape configured to stop the propagation of a tear and/or disruption of the substrate 4924. For example, the tear propagation limit aperture 4948 can be oval shaped. In other embodiments, the proximal boundary of the tear propagation limit aperture 4948 can be reinforced to ensure that the tear in the substrate 4924 does not extend beyond the tear propagation limit aperture 4948.

The battery assembly 4962 of the electronic circuit system 4900 comprises two batteries stacked on top of one another. The battery assembly 4962 has a first surface 4964 and a second surface 4966. The first surface 4964 of the battery assembly 4962 can contact an electrical contact (not shown) disposed on the substrate 4924. The second surface 4966 of the battery assembly 4962 is configured to contact a contact portion 4918 of a distal end portion 4916 of a battery clip 4910. When both the electrical contact of the substrate 4924 and the contact portion 4918 of the distal end portion 4916 of the battery clip 4910 contact the battery assembly 4962, the batteries of the battery assembly 4962 are placed in electrical communication with the electronic circuit system 4900. Said another way, when the electrical contact of the substrate 4924 and the contact portion 4918 of the distal end portion 4916 of the battery clip 4910 contact the battery assembly 4962, the battery assembly 4962 is configured to supply power to the electronic circuit system 4900.

The battery clip 4910 (shown in FIG. 18) includes a proximal end portion 4912 and a distal end portion 4916. The proximal end portion 4912 defines a retention aperture 4913. The retention aperture 4913 is configured to receive the battery clip protrusion 4173 of the electronic circuit system housing 4170. In this manner, the battery clip protrusion 4173 maintains the position of the battery clip 4910 with respect to the electronic circuit system housing 4170 and/or the battery assembly 4962.

The distal end portion 4916 of the battery clip 4910 includes a contact portion 4918 and an angled portion 4917. As described above, the contact portion 4918 is configured to contact the second surface 4916 of the battery assembly 4962 to place the battery assembly 4962 in electrical communication with the electronic circuit system 4900. The angled portion 4917 of the distal end portion 4916 of the battery clip 4910 is configured to allow a proximal end portion 4236 of a battery isolation protrusion 4235 (see e.g., FIG. 25) to be disposed between the second surface 4966 of the battery assembly 4962 and the contact portion 4918 of the distal end portion 4916 of the battery clip 4910. When the battery isolation protrusion 4235 is disposed between the second surface 4966 of the battery assembly 4962 and the contact portion 4918 of the distal end portion 4916 of the battery clip 4910, the electrical path between the battery assembly 4962 and the remainder of the electrical circuit system 4900 is severed, thereby removing power from the electronic circuit system 4900. The contact portion 4918 of the distal end portion 4916 of the battery clip 4910 is biased such that when the battery isolation protrusion 4235 is removed, the contact portion 4918 will move into contact the second surface 4916 of the battery assembly 4962, thereby restoring electrical communication between the battery assembly 4962 and the electronic circuit system 4900. In some embodiments, the battery isolation protrusion 4235 can be repeatedly removed from between the second surface 4966 of the battery assembly 4962 and the contact portion 4918 of the distal end portion 4916 of the battery clip 4910 and reinserted. Said another way, the battery isolation protrusion 4235 and the battery clip 4910 collectively form a reversible on/off switch.

The audio output device 4956 of the electronic circuit system 4900 is configured to output audible sound to a user in response to a use of the medical injector 4000. In some embodiments, the audible output device 4956 can be a speaker. In some embodiments, the audible sound can be, for example, associated with a recorded message and/or a recorded speech. In other embodiments, the audible instructions can be an audible beep, a series of tones and/or or the like.

In other embodiments, the medical injector 4000 can have a network interface device (not shown) configured to operatively connect the electronic circuit system 4900 to a remote device (not shown) and/or a communications network (not shown). In this manner, the electronic circuit system 4900 can send information to and/or receive information from the remote device. The remote device can be, for example, a remote communications network, a computer, a compliance monitoring device, a cell phone, a personal digital assistant (PDA) or the like. Such an arrangement can be used, for example, to download replacement processor-readable code from a central network to the electronic circuit system 4900. In some embodiments, for example, the electronic circuit system 4900 can download information associated with a medical injector 4000, such as an expiration date, a recall notice, updated use instructions or the like. Similarly, in some embodiments, the electronic circuit system 4900 can upload compliance information associated with the use of the medical injector 4000 via the network interface device.

Figure 24:
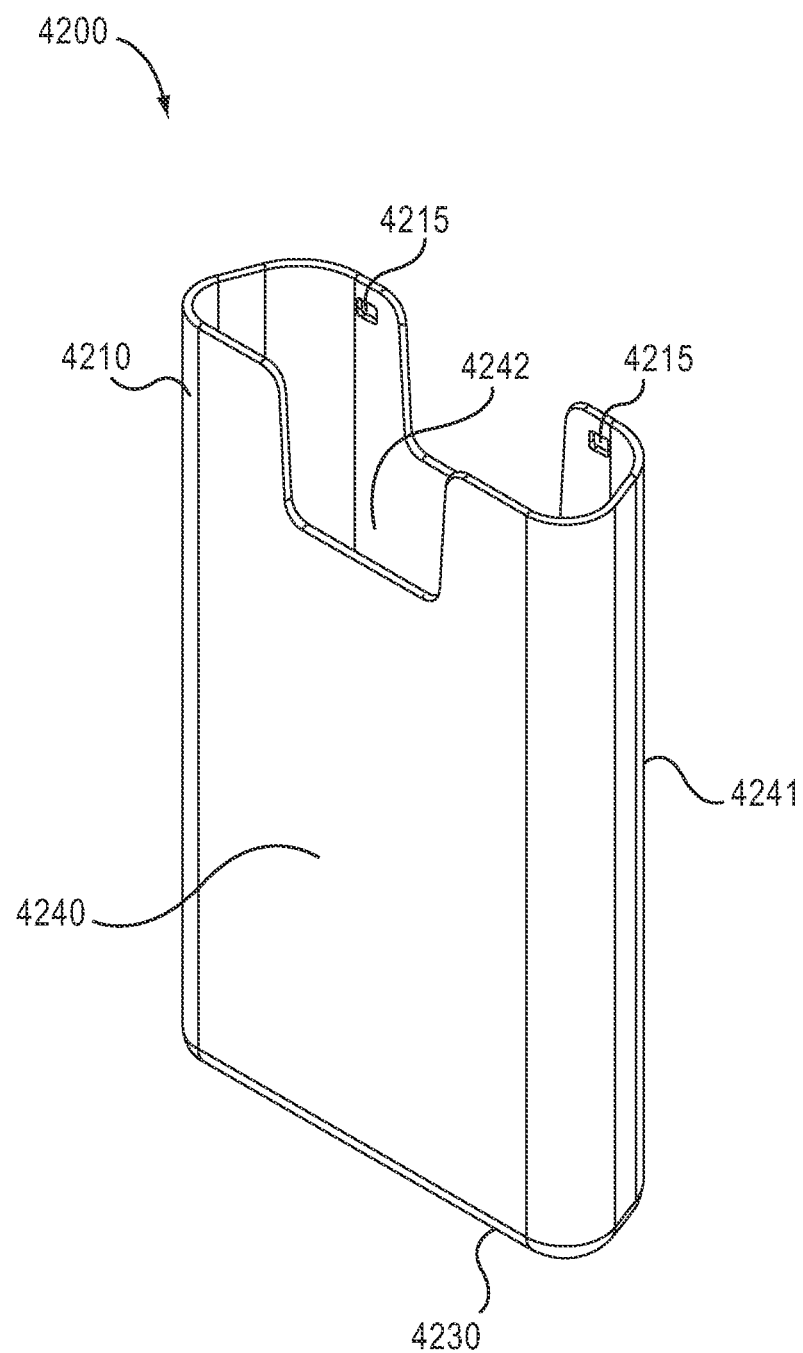
FIGS. 24 and 25 are perspective views of a cover of the medical injector illustrated in FIG. 3.
Figure 25:
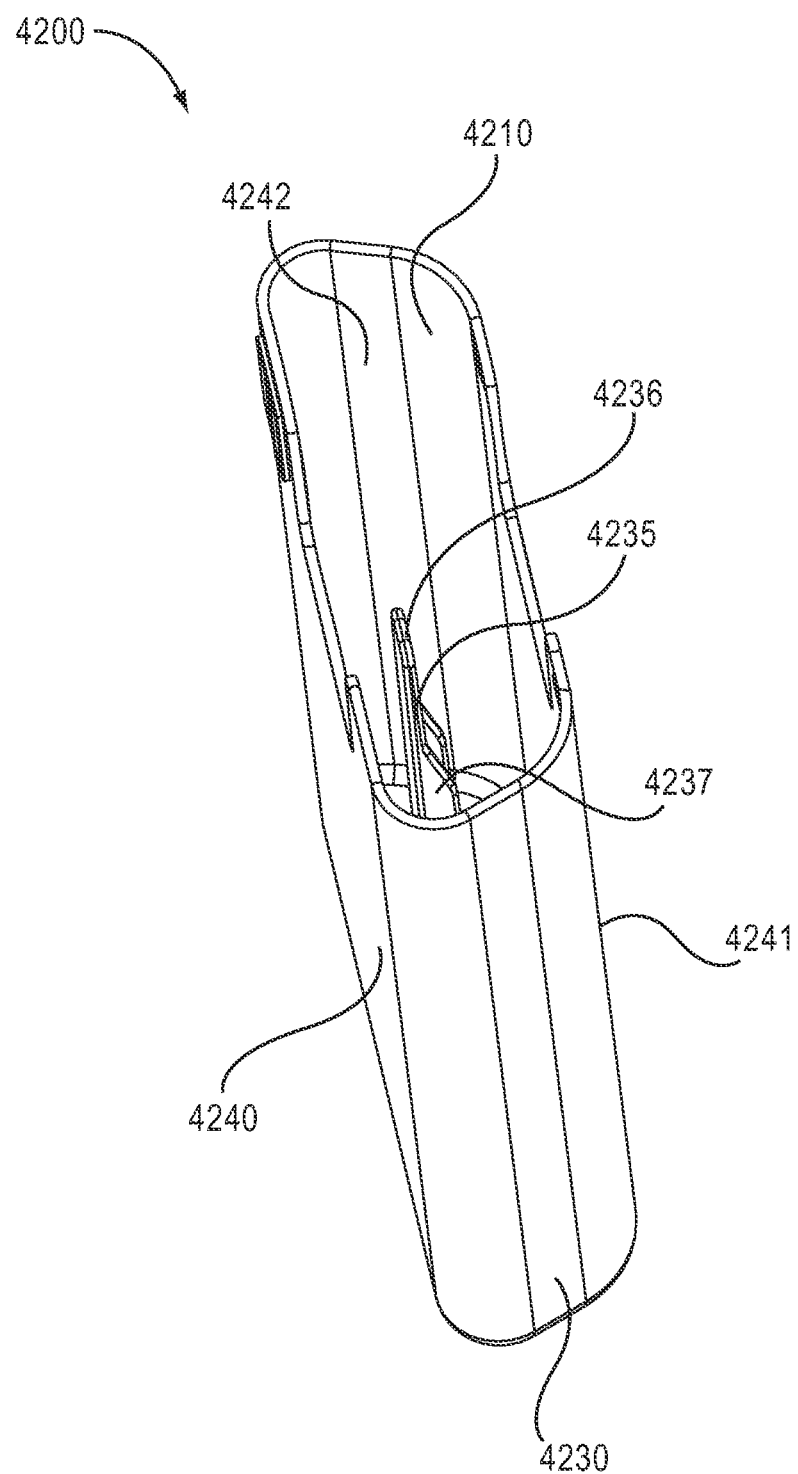
Figure 26:
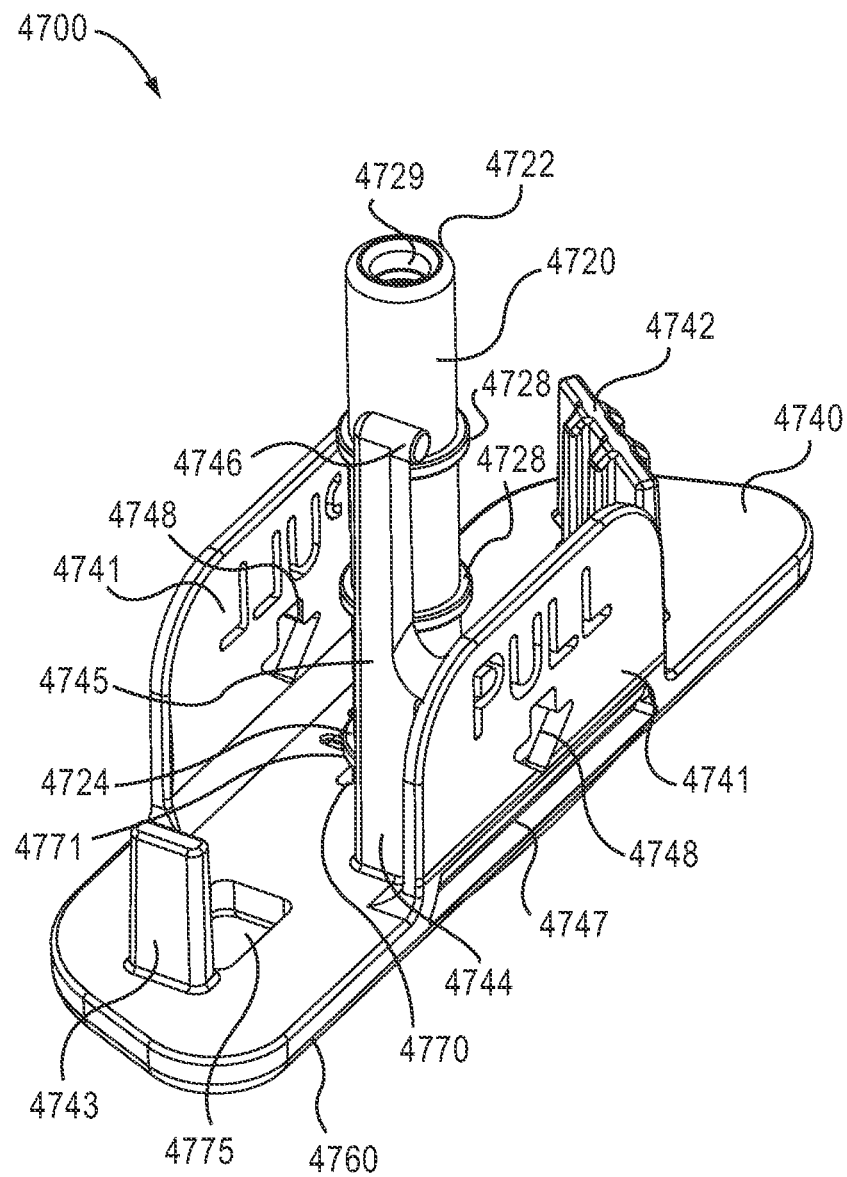
FIG. 26 is a perspective view of a safety lock of the medical injector illustrated in FIG. 3.

FIGS. 24 and 25 show the cover 4200 of the medical injector 4000. The cover 4200 includes a proximal end portion 4210 and a distal end portion 4230, and defines a cavity 4242. The cavity 4242 of the cover 4200 is configured to receive at least a portion of the housing 4110. The proximal end portion 4210 defines apertures 4215 configured to receive the cover retention protrusions 4142 of the housing 4110 (shown in FIGS. 4 and 6). In this manner, the apertures 4215 and the cover retention protrusions 4142 of the housing 4110 removably retain the cover 4200 about at least a portion of the housing 4110. Said another way, the apertures 4215 and the cover retention protrusions 4142 of the housing 4110 are configured such that the cover 4200 can be removed from a portion of the housing 4110 and then replaced about the portion of the housing 4110.

The distal end portion 4230 of the cover 4200 includes a battery isolation protrusion 4235. The battery isolation protrusion 4235 includes a proximal end portion 4236 and a tapered portion 4237. The proximal end portion 4236 of the battery isolation protrusion 4235 is configured to be removably disposed between the second surface 4966 of the battery assembly 4962 and the contact portion 4918 of the distal end portion 4916 of the battery clip 4910, as described above.

FIGS. 26-29 show the safety lock 4700 of the medical injector 4000. The safety lock 4700 of the medical injector 4000 includes a proximal surface 4740, a distal surface 4760 opposite the proximal surface 4740 and a needle sheath 4720. The safety lock 4700 defines a needle sheath aperture 4770 and a battery isolation protrusion aperture 4775. The battery isolation protrusion aperture 4775 is configured to receive the battery isolation protrusion 4235 of the cover 4200 such that the battery isolation protrusion 4235 can be disposed within the electronic circuit system cavity 4153 or the electronic circuit system 4900, as described above. Similarly stated, the battery isolation protrusion aperture 4775 of the safety lock 4700 is aligned with the battery isolation protrusion aperture 4121 of the housing 4110, such that the battery isolation protrusion 4235 can be disposed within the electronic circuit system cavity 4153 when the cover 4200 is disposed about a portion of the housing 4110.

The proximal surface 4740 of the safety lock 4700 includes a safety lock protrusion 4742, a stopper 4743, an actuator 4744 and two opposing pull tabs 4741. As described above, when the safety lock 4700 is in a first (locked) position, the safety lock protrusion 4742 is configured to be disposed in the opening 4554 defined by the extensions 4552 of the distal end portion 4544 of the release member 4540. Accordingly, the safety lock protrusion 4742 is configured to prevent the extensions 4552 from moving closer to each other, thereby preventing proximal movement of the release member 4540 of the medicament delivery mechanism 4500 and/or delivery of a medicament. The stopper 4743 of the safety lock 4700 is a protrusion extending from the proximal surface 4740 of the safety lock 4700. The stopper 4743 is configured to contact a portion of the housing 4110 to limit the proximal movement of the safety lock 4700 relative to the housing 4110. In other embodiments, the stopper 4743 can be any structure configured to limit the proximal movement of the safety lock 4700.

The actuator 4744 of the safety lock 4700 has an elongated portion 4745 and a protrusion 4746. The elongated portion 4745 extends in a proximal direction from the proximal surface 4740. In this manner, the elongated portion 4745 can extend through a safety lock actuator opening 4356 of the base 4300 (see e.g., FIG. 30) and within the safety lock actuator groove 4123 of the housing 4110 and the safety lock actuator groove 4182 of the electronic circuit system housing 4170. The protrusion 4746 extends in a direction substantially transverse to the elongated portion 4745 and/or substantially parallel to the proximal surface 4740 of the safety lock 4700. As described above, the opening 4928 of the first actuation portion 4926 is configured to receive the protrusion 4746 of the actuator 4744 of the safety lock 4700.

The pull tabs 4741 of the safety lock 4700 include a grip portion 4747 and indicia 4748. The grip portion 4747 of the pull tabs 4741 provides an area for the user to grip and/or remove the safety lock 4700 from the rest of the medicament delivery system 4700. The indicia 4748 provides instruction on how to remove the safety lock 4700. In some embodiments, for example, the indicia 4748 can indicate the direction the user should pull the safety lock 4700 to remove the safety lock 4700.

Figure 28:
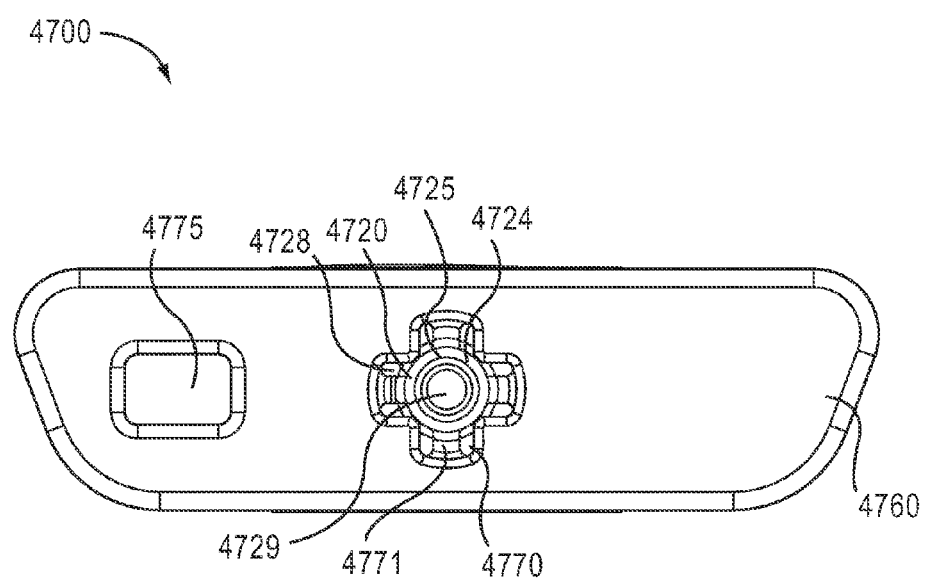
FIG. 28 is a bottom view of the safety lock of the medical injector illustrated in FIG. 26.
Figure 29:
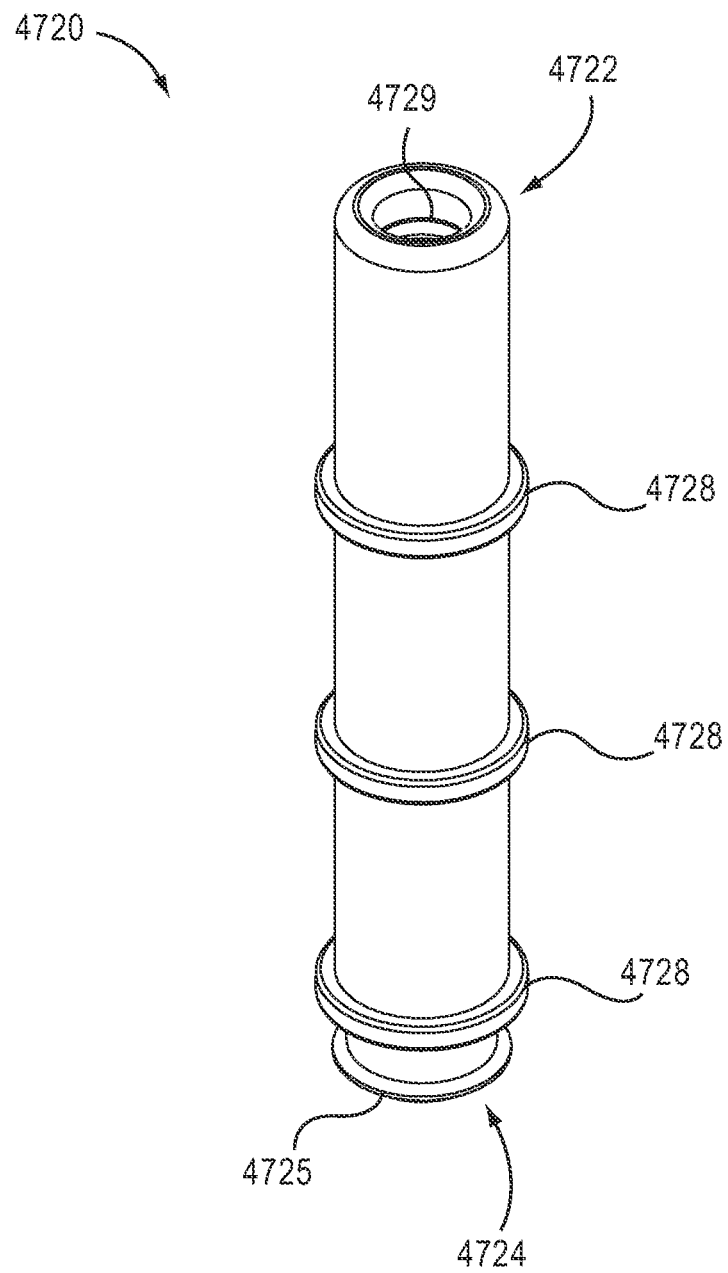
FIG. 29 is a perspective view of a needle sheath of the safety lock of the medical injector illustrated in FIG. 26.

As shown in FIG. 28, the needle sheath 4720 of the safety lock 4700 includes a distal end portion 4724, a proximal end portion 4722 and a plurality of ribs 4728. The needle sheath 4720 can also define a lumen 4729. The lumen 4729 of the safety lock 4700 is configured to receive the needle 4512. In this manner, the needle sheath 4720 can protect the user from the needle 4512 and/or can keep the needle 4512 sterile before the user uses the medical injector 4000. The proximal end portion 4722 of the needle sheath is configured to contact the distal end portion 4522 of the carrier 4520 of the medicament delivery mechanism 4500.

Figure 33:
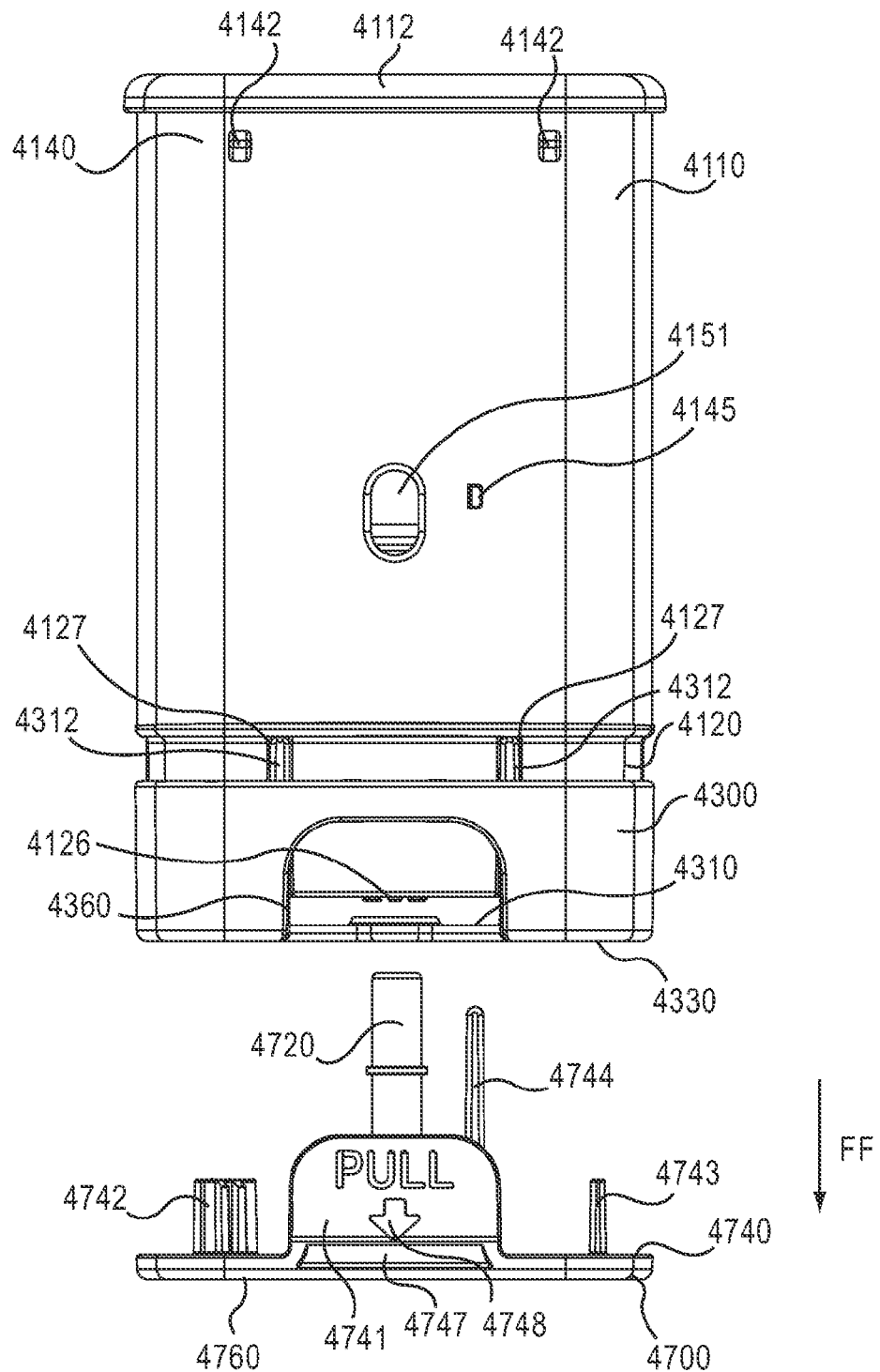
FIG. 33 is a back view of the medical injector illustrated in FIG. 3 in a third configuration.
Figure 34:
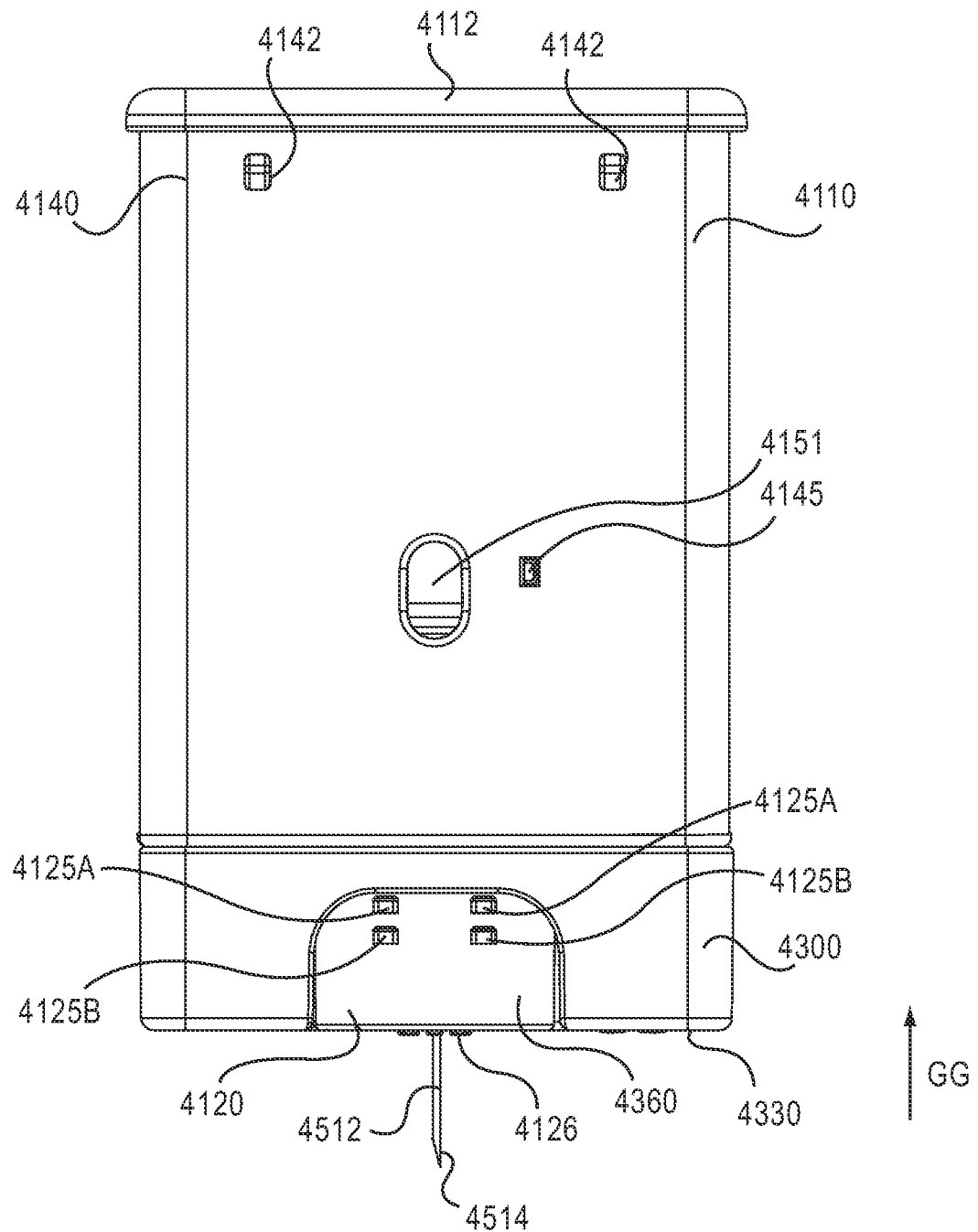
FIG. 34 is a back view of the medical injector illustrated in FIG. 3 in a fourth configuration.

The distal end portion 4724 of the needle sheath 4720 has an angled ridge 4725. The angled ridge 4725 is configured to allow the proximal end portion 4722 of the needle sheath 4720 to irreversibly move through the needle sheath aperture 4770 of the safety lock 4700 in a distal direction. Said another way, the angled ridge 4725 can be configured in such a way as to allow the proximal end portion 4722 of the needle sheath 4720 to move through the needle sheath aperture 4770 in a distal direction, but not in a proximal direction. The needle sheath aperture 4770 has retaining tabs 4771 configured to engage the proximal end of the angled ridge 4725 when the needle sheath 4720 is moved in a proximal direction. In this manner, the retaining tabs 4771 prevent the proximal movement of the needle sheath with respect to the safety lock 4700. Further, the retaining tabs 4771 are configured to engage the proximal end of the angled ridge 4725 when the safety lock 4700 is moved in a distal direction. Said another way, as shown in FIG. 33, the needle sheath 4720 is removed from the needle 4512 when the safety lock 4700 is moved in a distal direction with respect to the housing 4110.

Figure 30:
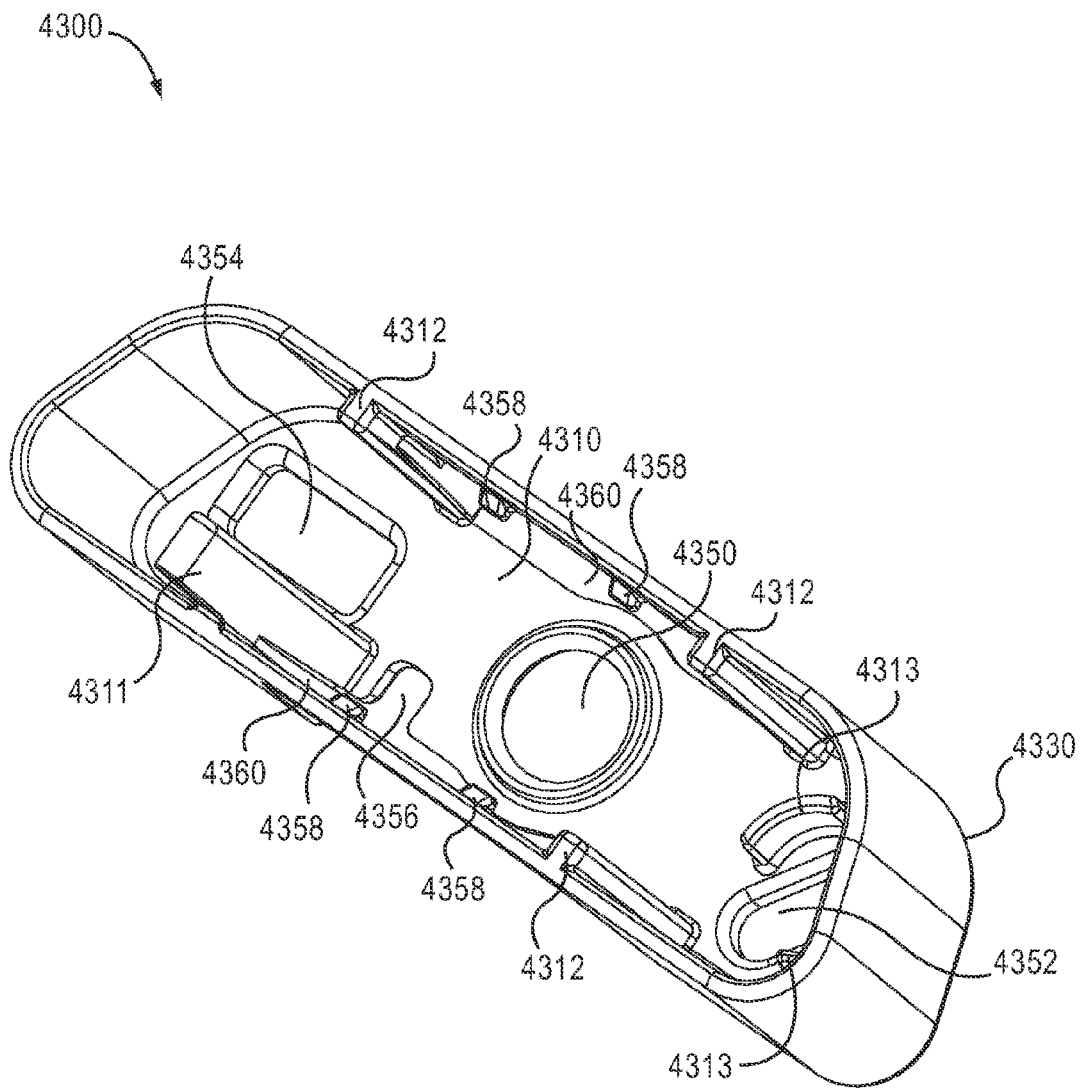
FIG. 30 is a perspective view of a base of the medical injector illustrated in FIG. 3.
Figure 31:
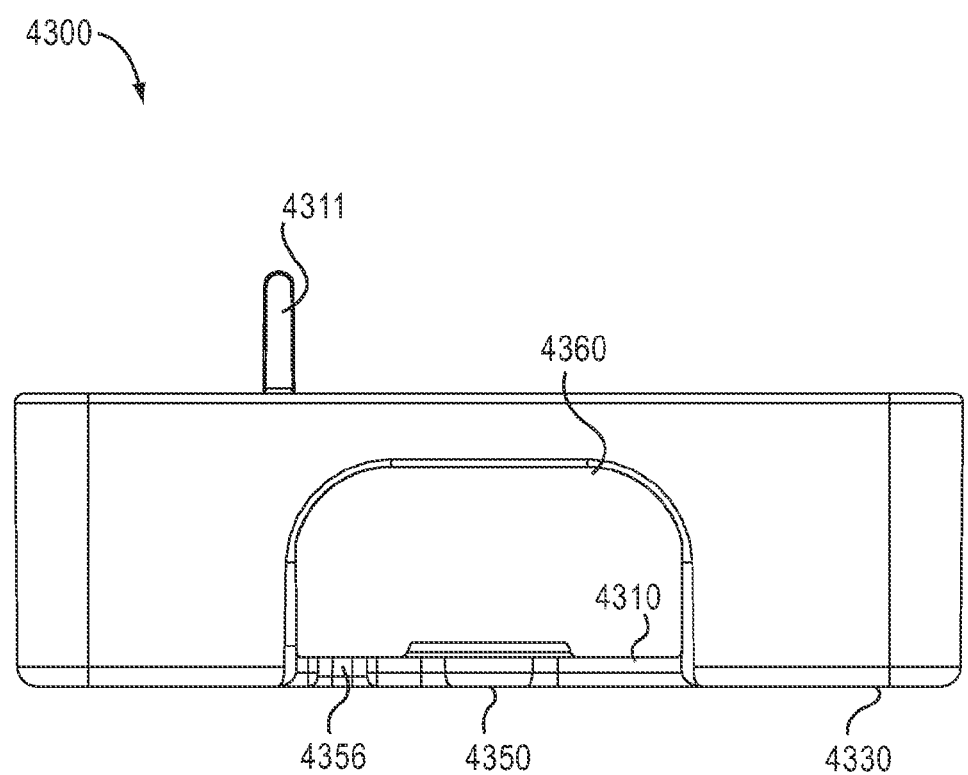
FIG. 31 is a front view of the base of the medical injector illustrated in FIG. 3.

FIGS. 30-31 show the base 4300 of the medical injector 4000. The base 4300 includes a proximal surface 4310, a distal surface 4330 and base connection knobs 4358. The base 4300 defines a needle aperture 4350, a safety lock protrusion aperture 4352, a battery isolation protrusion aperture 4354, a safety lock actuator opening 4356, and pull tab openings 4360. The needle aperture 4350 is configured to receive the needle 4512 when the medical injector 4000 is actuated. The safety lock protrusion aperture 4352 of the base 4300 receives the safety lock protrusion 4742 of the safety lock 4700. The battery isolation protrusion aperture 4354 of the base 4300 receives the battery isolation protrusion 4235 of the cover 4200 and the stopper 4743 of the safety lock 4700. The safety lock actuator opening 4356 receives the safety lock actuator 4744 of the safety lock 4700. The pull tab openings 4360 are configured to receive the pull tabs 4741 of the safety lock 4700.

The proximal surface 4310 of the base 4300 includes an actuator 4311, guide members 4312, and protrusions 4313. The actuator 4311 is an elongate member configured to engage the substrate 4924 of the electronic circuit system 4900. As described above, the opening 4945 of the second actuation portion 4946 is configured to receive the actuator 4311 of the base 4300. The guide members 4312 of the base 4300 are configured to engage and/or slide within the base rail grooves 4127 of the housing 4110, as described above. The protrusions 4313 of the base 4300 are configured to engage the tapered surfaces 4549 of the extensions 4552 of the release member 4540. As described in further detail herein, when the safety lock 4700 is removed and the base 4300 is moved in a proximal direction with respect to the housing 4110, the protrusion 4313 of the base 4300 are configured to move the extensions 4552 of the release member 4540 closer to each other, actuating the medicament delivery mechanism 4500. As described above, the base connection knobs 4358 are configured to engage the base retention recesses 4125A, 4125B in a way that allows proximal movement of the base 4300 but limits distal movement of the base 4300.

Figure 32:
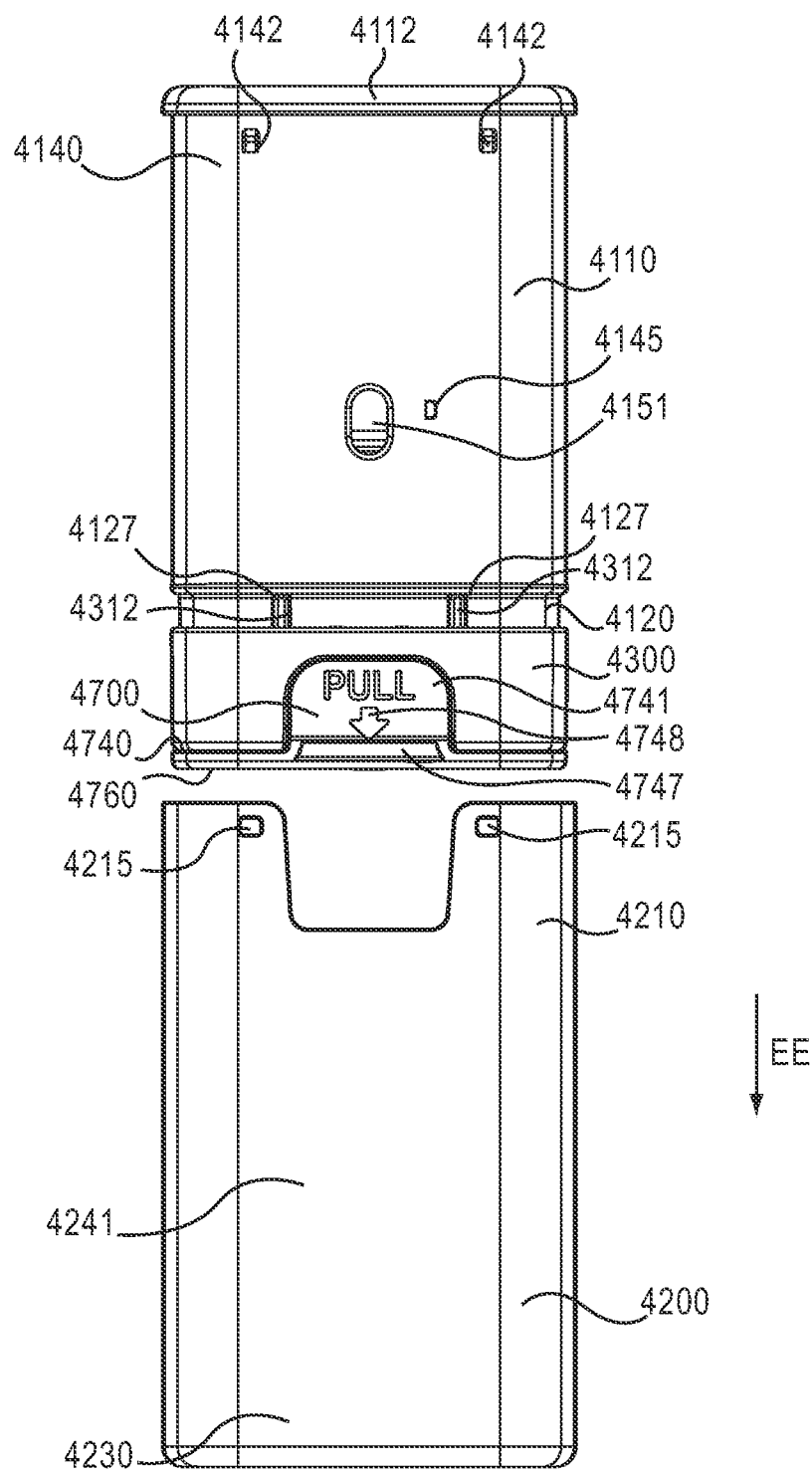
FIG. 32 is a back view of the medical injector illustrated in FIG. 3 in a second configuration.

As shown in FIG. 32, the medical injector 4000 is first enabled by moving the medicament delivery device from a first configuration to a second configuration by moving the cover 4200 from a first position to a second position. The cover 4200 is moved from the first position to the second position by moving it with respect to the housing 4110 in the direction shown by the arrow EE in FIG. 32. When the cover 4200 is moved with respect to the housing 4110 in the direction EE, the battery isolation protrusion 4235 is removed from the area between the battery clip 4910 and the second surface 4966 of the battery assembly 4962. In this manner, the battery assembly 4962 can be operatively coupled to the electronic circuit system 4900 when the cover 4200 is removed, thereby providing power to the electronic circuit system 4900.

When power is provided, as described above, the electronic circuit system 4900 can output one or more predetermined electronic outputs. For example, in some embodiments, the electronic circuit system 4900 can output an electronic signal associated with recorded speech to the audible output device 4956. Such an electronic signal can be, for example, associated with a .WAV file that contains a recorded instruction instructing the user in the operation of the medical injector 4000. Such an instruction can state, for example, "remove the safety tab near the base of the auto-injector." The electronic circuit system 4900 can simultaneously output an electronic signal to one and/or both of the LEDs 4958A, 4958B thereby causing one and/or both of the LEDs 4958A, 4958B to flash a particular color. In this manner, the electronic circuit system 4900 can provide both audible and visual instructions to assist the user in the initial operation of the medical injector 4000.

In other embodiments, the electronic circuit system 4900 can output an electronic output associated with a description and/or status of the medical injector 4000 and/or the medicament contained therein. For example, in some embodiments, the electronic circuit system 4900 can output an audible message indicating the type of medicament contained in the medical injector 4000, the expiration date of the medicament, the dosage of the medicament or the like.

As described above, the medical injector 4000 can be can be repeatedly moved between the first configuration and the second configuration when the cover 4200 is moved repeatedly between the first position and the second position respectively. Said another way, the cover 4200 can be removed and replaced about the housing 4110 any number of times. When the cover 4200 is moved from the second position to the first position, the battery isolation protrusion 4235 is inserted between the battery clip 4910 and the second surface 4966 of the battery assembly 4962, deactivating the electronic circuit system 4900. When the cover is moved from the first position to the second position a second time, the electronic circuit system 4900 is once again activated. In this manner, the cover 4200 can be removed and the electronic circuit system 4900 can output an electronic output without compromising the sterility of the needle 4512.

After the cover 4200 is removed from the housing 4110, the medical injector 4000 can be moved from the second configuration to a third configuration by moving the safety lock 4700 from a first position to a second position. The safety lock 4700 is moved from a first position to a second position by moving the safety lock 4700 with respect to the housing 4110 in the direction shown by the arrow FF in FIG. 33. When the safety lock 4700 is moved from the first position to the second position, the safety lock protrusion 4742 is removed from between the extensions 4552 of the release member 4540, thereby enabling the medicament delivery member 4500. Moreover, as shown in FIGS. 21 and 22, when the safety lock 4700 is moved from the housing 4110, the actuator 4744 of the safety lock 4700 moves in the direction CC as shown in FIG. 22, irreversibly moving the first switch 4972 from a first state (e.g., a state of electrical continuity) to a second state (e.g., a state of electrical discontinuity). When the actuator 4744 of the safety lock 4700 moves irreversibly the first switch 4972 of the electronic circuit system 4900 to the second state, the electronic circuit system 4900 can output one or more predetermined electronic outputs. For example, in some embodiments, a processor (not shown) can output an electronic signal associated with recorded speech to the audible output device 4956. Such an electronic signal can be, for example, associated with a recorded message notifying the user of the status of the medical injector 4000. Such a status message can state, for example, "The medical injector is now enabled." The electronic circuit system 4900 can also simultaneously output an electronic signal to one and/or both of the LEDs 4958A, 4958B, thereby causing one and/or both of the LEDs 4958A, 4958B to stop flashing, change color or the like.

In some embodiments, the first actuation portion 4926 and the actuator 4744 can be configured such that the actuator 4744 must move a predetermined distance before the actuator 4744 engages the boundary 4929 of the opening 4928. For example, in some embodiments, the actuator 4744 must move approximately 0.200 inches before the actuator 4744 engages the boundary 4929 of the opening 4928. In this manner, the safety lock 4700 can be moved slightly without irreversibly moving the first switch 4972 of the electronic circuit system 4900 to the second state. Accordingly, this arrangement will permit the user to inadvertently and/or accidentally move the safety lock 4700 without actuating the electronic circuit system 4900.

In some embodiments, the electronic circuit system 4900 can be configured to output the status message for a predetermined time period, such as, for example, five seconds. After the predetermined time period has elapsed, the electronic circuit system 4900 can output an audible message further instructing the user in the operation of the medical injector 4000. Such an instruction can state, for example, "Place the base of the auto-injector against the patient's thigh. To complete the injection, press the base firmly against the patient's thigh." In some embodiments, the electronic circuit system 4900 can simultaneously output an electronic signal to one and/or both of the LEDs 4958A, 4958B, thereby causing one and/or both of the LEDs 4958A, 4958B to flash a particular color. In this manner, the electronic circuit system 4900 can provide both audible and/or visual instructions to assist the user in the placement and actuation of the medical injector 4000. In some embodiments, the electronic circuit system 4900 can be configured to repeat the instructions after a predetermined time period has elapsed.

As described above, in other embodiments, the medical injector 4000 can have a network interface device (not shown) configured to operatively connect the electronic circuit system 4900 to a remote device (not shown) and/or a communications network (not shown). In this manner, the electronic circuit system 4900 can send a wireless signal notifying a remote device that the safety lock 4700 of the medical injector 4000 has been removed and that the medical injector 4000 has been armed.

After the safety lock 4700 is moved from the first position to the second position, the medical injector 4000 can be moved from the third configuration to a fourth configuration by moving the base 4300 from a first position to a second position. The base 4300 is moved from its first position to its second position by placing the medical injector 4000 against the body of the patient and moving the base 4300 with respect to the housing 4110 in the direction shown by the arrow GG in FIG. 34. Moving the base 4300 from the first position to the second position causes the protrusions 4313 on the proximal surface 4310 of the base 4300 to engage the tapered surfaces 4549 of the extensions 4552 of the release member 4540, causing the release member 4540 to actuate the medicament delivery mechanism 4500 and deliver a medicament to a body of a patient.

When the base 4300 is moved from the first position to the second position, the medicament delivery mechanism 4500 is actuated such that the puncturer 4541 of the release member 4540 is brought in contact with and/or punctures the frangible seal 4573 of the gas container 4570. In some embodiments, the movement of the release member 4540 can be caused by a spring (not shown in FIG. 12). After the frangible seal 4573 has been punctured, an actuating portion of a compressed gas can escape from the gas container 4570 and flow via the gas passageway 4144 into the medicament cavity 4157. The gas applies gas pressure to the movable member 4530 causing the movable member 4530 and the carrier 4520 to move in a distal direction within the medicament cavity 4157. When the carrier 4520 moves distally within the medicament cavity 4157, the carrier 4520 and the medicament container 4560 are in a first configuration. Accordingly, as described above, the medicament container 4560 is connected to the carrier 4520 by a "snap fit" connection. In this manner, the medicament container 4560 and the needle 4512 contemporaneously move with movable member 4530 and/or the carrier 4520 in a distal direction. As described above, the proximal end portion 4516 of the needle 4512 is connected to the distal end portion 4522 of the carrier 4520 and is spaced from the seal 4523 of the medicament container 4560 when the carrier 4520 is in its first configuration. Said another way, the medicament container 4560 and the needle 4512 do not define a medicament delivery path when the carrier 4520 is in the first configuration. The movement of the needle 4512 in a distal direction causes the proximal end portion 4516 of the needle 4512 to exit the housing 4110 and enter the body of a patient prior to administering a medicament.

After the carrier 4520 and/or the needle 4512 have moved within the medicament cavity 4157 a predetermined distance, the carrier 4520 and the medicament container 4560 are moved from the first configuration to a second configuration. In the second configuration of the carrier 4520, the medicament container 4560 is released from the "snap-fit" allowing the medicament container 4560 and the movable member 4530 to continue to move in a distal direction relative to the carrier 4520. Said another way, the medicament container 4560 is configured to slidably move within the carrier 4520 when the carrier is moved from the first configuration to the second configuration. As the medicament container 4560 continues to move within the carrier 4520, the proximal end portion 4516 of the needle 4512 contacts and punctures the seal 4523 of the medicament container 4560. This allows the medicament contained in the medicament container 4560 to flow into the lumen (not shown) defined by the needle 4512, thereby defining a medicament delivery path.

As the medicament container 4560 contacts the distal end of the carrier 4520, the medicament container 4560 stops moving within the carrier 4520 while the movable member 4530 continues to move in a distal direction. This causes the piston portion 4534 of the movable member 4530 to sealingly slide and/or move within the medicament container 4560 containing a liquid medicament. As the piston portion 4534 of the movable member 4530 sealingly slides and/or moves within the medicament container 4560, the piston portion 4534 generates a pressure upon the medicament contained within the medicament container 4560, thereby allowing at least a portion of the medicament to flow out of the medicament container 4560 and into the lumen defined by the needle 4512. The medicament is delivered to a body of a user via the medicament delivery path defined by the medicament container 4560 and the needle 4512.

As described above, the actuator 4538 of the base 4300 actuates the electronic circuit 4900 to trigger a predetermined output or sequence of outputs when the base 4520 is moved from its first position to its second position (see, e.g., FIGS. 19-23). When the actuator 4538 is moved in a proximal direction relative to the opening 4945, as shown by the arrow DD in FIG. 23, the electronic circuit system 4900 is actuated to output one or more predetermined electronic outputs. For example, in some embodiments, the electronic circuit system 4900 can output an electronic signal associated with recorded speech to the audible output device 4956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 4000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 4900 can also simultaneously output an electronic signal to one and/or both LEDs 4958A, 4958B, thereby causing one and/or both LEDs 4958A, 4958B to stop flashing, change color or the like, to provide a visual indication that the injection is complete. In other embodiments, the electronic circuit system 4900 can send a wireless signal notifying a remote device that the injection is complete. In this manner, a patient's compliance can be monitored.

In some embodiments, the second actuation portion 4946 and the actuator 4538 can be configured such that the base 4500 and/or the actuator 4538 must move a predetermined distance before the actuator 4538 engages the boundary 4949 of the opening 4945. For example, in some embodiments, the actuator 4538 must move approximately 0.200 inches before the actuator 4538 engages the boundary 4949 of the opening 4945. In this manner, the base 4700 can be moved slightly without irreversibly moving the second switch 4973 of the electronic circuit system 4900 to the second state. Accordingly, this arrangement will permit the user to inadvertently and/or accidentally move the base 4500 without actuating the electronic circuit system 4900.

Although the electronic circuit system 4900 is shown and described above as having two irreversible switches (e.g., switch 4972 and switch 4973), in other embodiments, an electronic circuit system can have any number of switches. Moreover, such switches can be either reversible or irreversible. For example, FIGS. 35-40 show portions of a medicament delivery device 5000 having an electronic circuit system 5900 having three irreversible switches.

Figure 39:
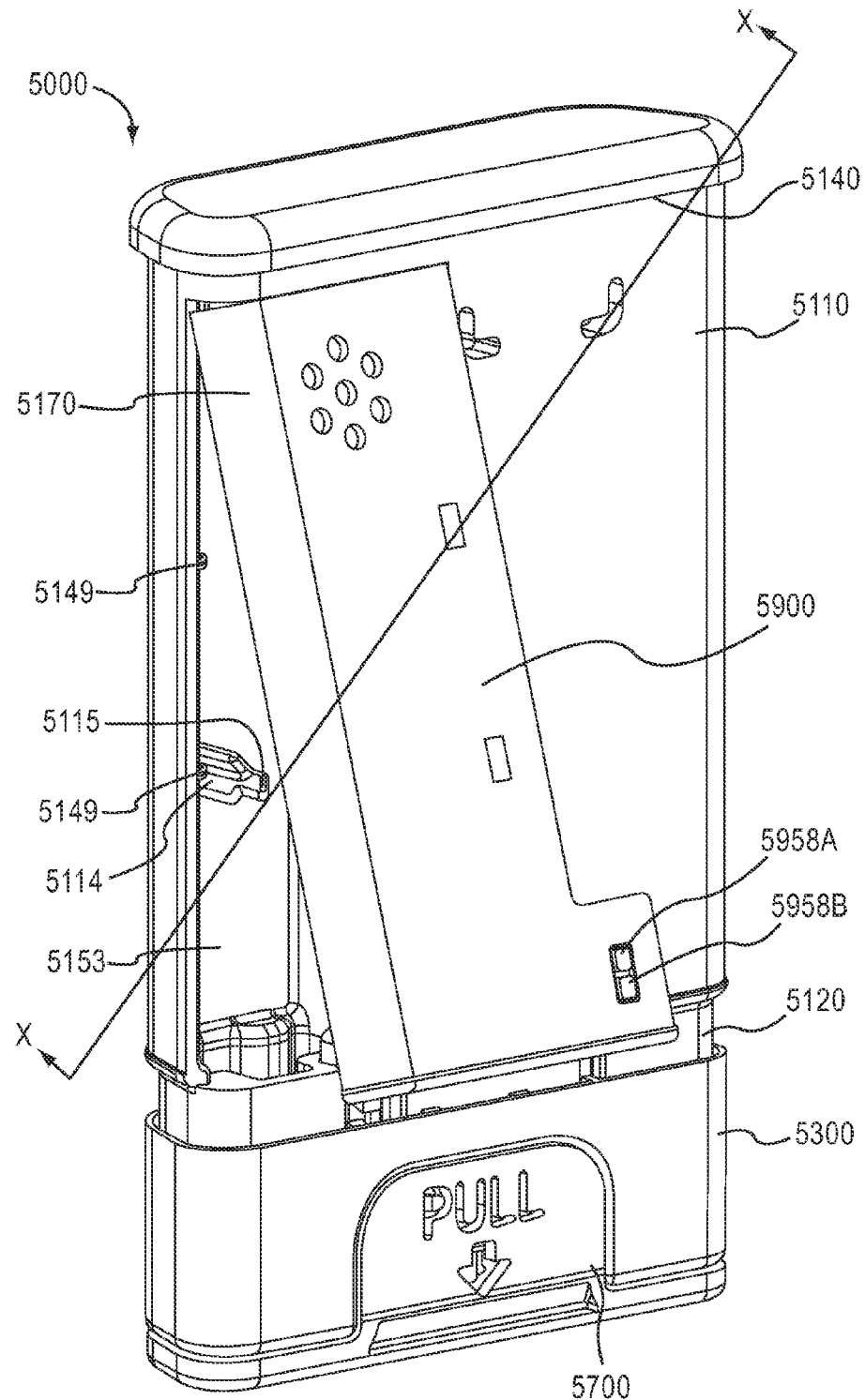
FIG. 39 is a perspective cross-sectional view of the housing and the electronic circuit system illustrated in FIG. 35 and FIG. 36 respectively.

The medicament delivery device 5000 is similar to the medical injector 4000 described above. As shown in FIG. 39, the medicament delivery device 5000 includes a housing 5110, a delivery mechanism (not shown), an electronic circuit system 5900, a cover (not shown), a safety lock 5700 and a base 5300. The structure and operation of the delivery mechanism, the cover, the safety lock 5700 and the base 5300 are similar to the structure and operation of the delivery mechanism 4500, the cover 4200, the safety lock 4700 and the base 4300, respectively. Accordingly, only the electronic circuit system 5900 and the housing 5110 are described in detail below.

Figure 35:
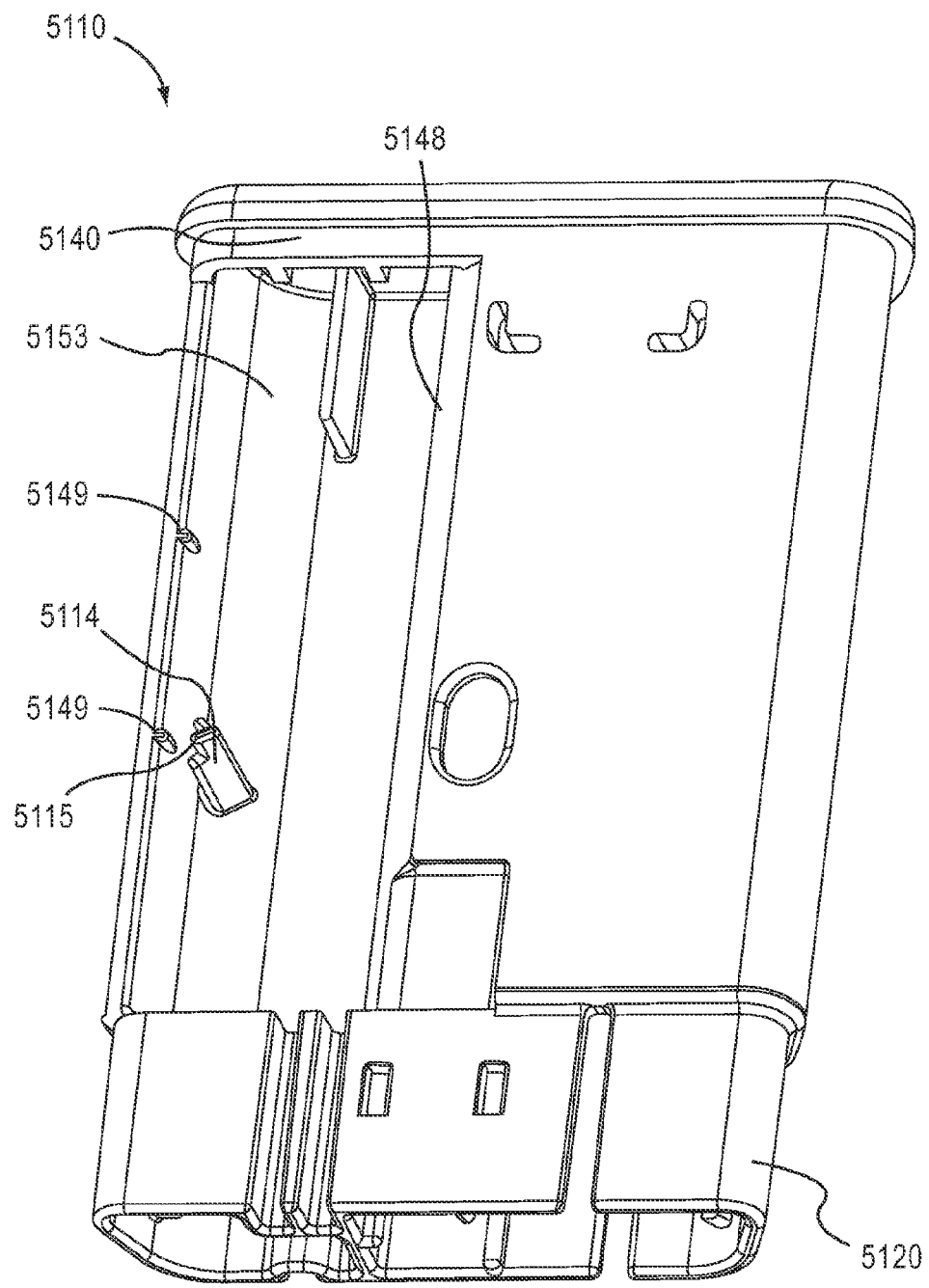
FIG. 35 is a perspective view of a housing of a medical injector according to an embodiment of the invention.

As shown in FIG. 35, the housing 5110 has a proximal end portion 5140 and a distal end portion 5120. The housing 5110 defines a gas cavity (not shown), a medicament cavity (not shown) and an electronic circuit system cavity 5153. The gas cavity and medicament cavity of the housing 5110 of the medicament delivery device 5000 are similar to the gas cavity 4154 and the medicament cavity 4157, shown and described above with reference to FIGS. 9 and 10.

The electronic circuit system cavity 5153 is configured to receive the electronic circuit system 5900. As described above, the electronic circuit system cavity 5153 is fluidically and/or physically isolated from the gas cavity and/or the medicament cavity by a sidewall 5148. The housing 5110 has protrusions 5149 configured to stabilize the electronic circuit system 5900 when the electronic circuit system 5900 is disposed within the electronic circuit system cavity 5153. The housing 5110 also defines connection apertures (not shown) configured to receive connection protrusions 5171 of the electronic circuit system 5900 (see e.g., FIG. 36). In this manner, the electronic circuit system 5900 can be coupled to the housing 5110 within the electronic circuit system cavity 5153 (see e.g., FIG. 39). In other embodiments, the electronic circuit system 5900 can be coupled within the electronic circuit system cavity 5153 by any other suitable means, such as an adhesive, a clip and/or the like.

The housing 5110 includes an actuation protrusion 5114 disposed within the electronic circuit system cavity 5153. As described in more detail herein, an angled end portion 5115 of the actuation protrusion 5114 of the housing 5110 is configured to engage a third actuation portion 5976 of a substrate 5924 of the electronic circuit system 5900 when the electronic circuit system 5900 is coupled to the housing 5110.

As shown in FIG. 39, the electronic circuit system 5900 is configured to fit within the electronic circuit system cavity 5153 of the housing 5110. Accordingly, as described above, the electronic circuit system 5900 is physically and/or fluidically isolated from the medicament cavity, the gas cavity and/or the medicament delivery path within the medicament delivery device 5000 (not shown). As described herein, the electronic circuit system 5900 is configured to output an electronic output associated with a use of the medicament delivery device 5000.

Figure 36:
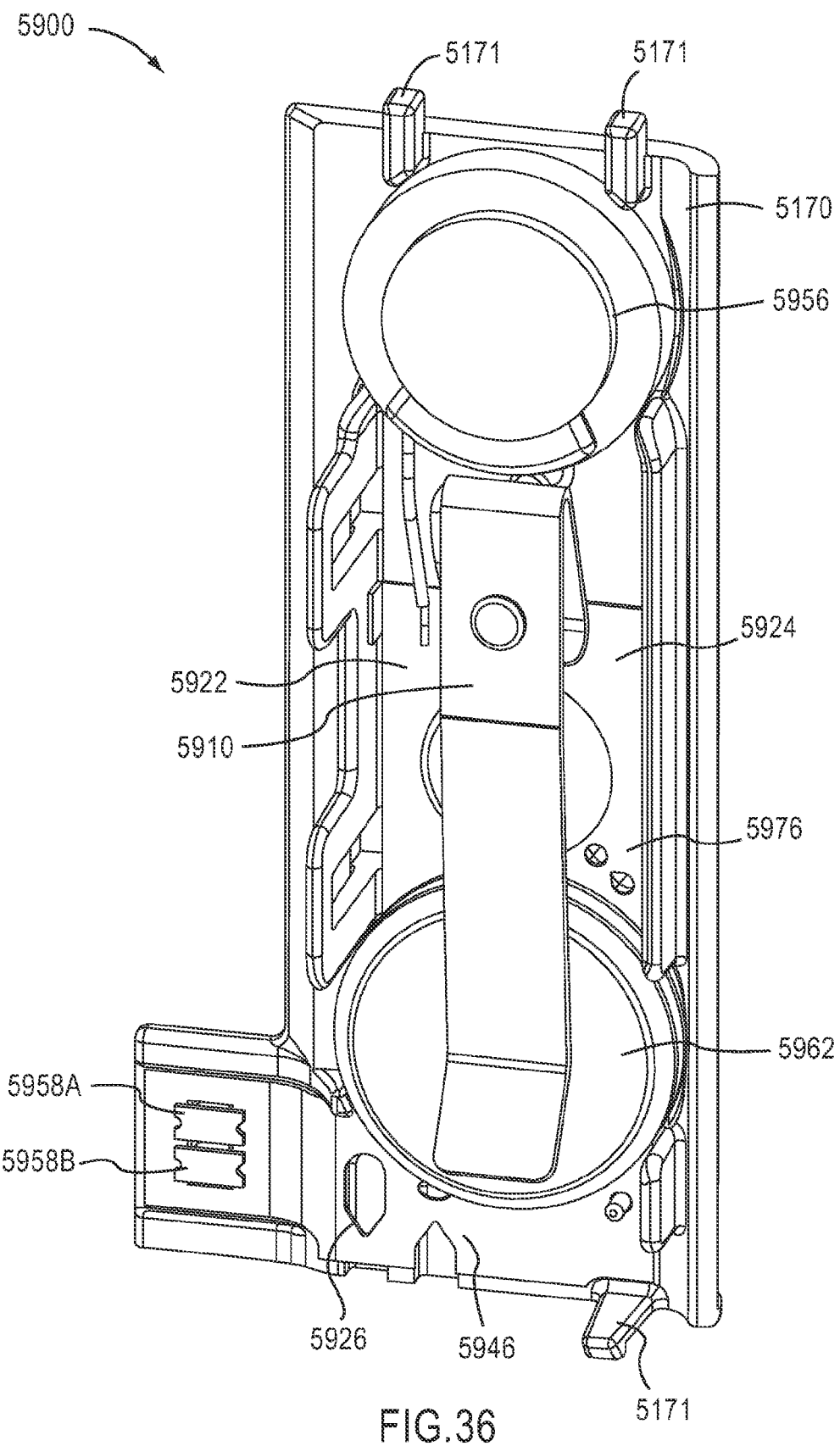
FIG. 36 is a perspective view of an electronic circuit system of a medical injector according to an embodiment of the invention.

As shown in FIG. 36, the electronic circuit system 5900 is similar to the electronic circuit system 4900 described above. The electronic circuit system 5900 of the medicament delivery device 5000 includes an electronic circuit system housing 5170, a printed circuit board 5922, a battery assembly 5962, an audio output device 5956, two light emitting diodes (LEDs) 5958A, 5958B and a battery clip 5910. The electronic circuit system housing 5170, the battery assembly 5962, the audio output device 5956, the two light emitting diodes (LEDs) 5958A, 5958B and the battery clip 5910 are similar to the battery assembly 4962, the audio output device 4956, the two light emitting diodes (LEDs) 4958A, 4958B and the battery clip 4910 of the electronic circuit system 4900 described above. Thus, a detailed discussion of these components is omitted.

The electronic circuit system 5900 also includes a processor 5950 configured to process electronic inputs (e.g., from input switches) and produce electronic outputs. As described herein, such electronic outputs can include audio or visual outputs associated with a use of the medicament delivery device 5000. The processor 5950 can be a commercially-available processing device dedicated to performing one or more specific tasks. For example, in some embodiments, the processor 5950 can be a commercially-available microprocessor, such as the Sonix SNC 12060 voice synthesizer. Alternatively, the processor 5950 can be an application-specific integrated circuit (ASIC) or a combination of ASICs, which are designed to perform one or more specific functions. In yet other embodiments, the processor 5950 can be an analog or digital circuit, or a combination of multiple circuits.

The processor 5950 can include a memory device (not shown) configured to receive and store information, such as a series of instructions, processor-readable code, a digitized signal, or the like. The memory device can include one or more types of memory. For example, the memory device can include a read only memory (ROM) component and a random access memory (RAM) component. The memory device can also include other types of memory suitable for storing data in a form retrievable by the processor 5950, for example, electronically-programmable read only memory (EPROM), erasable electronically-programmable read only memory (EEPROM), or flash memory.

Figure 37:
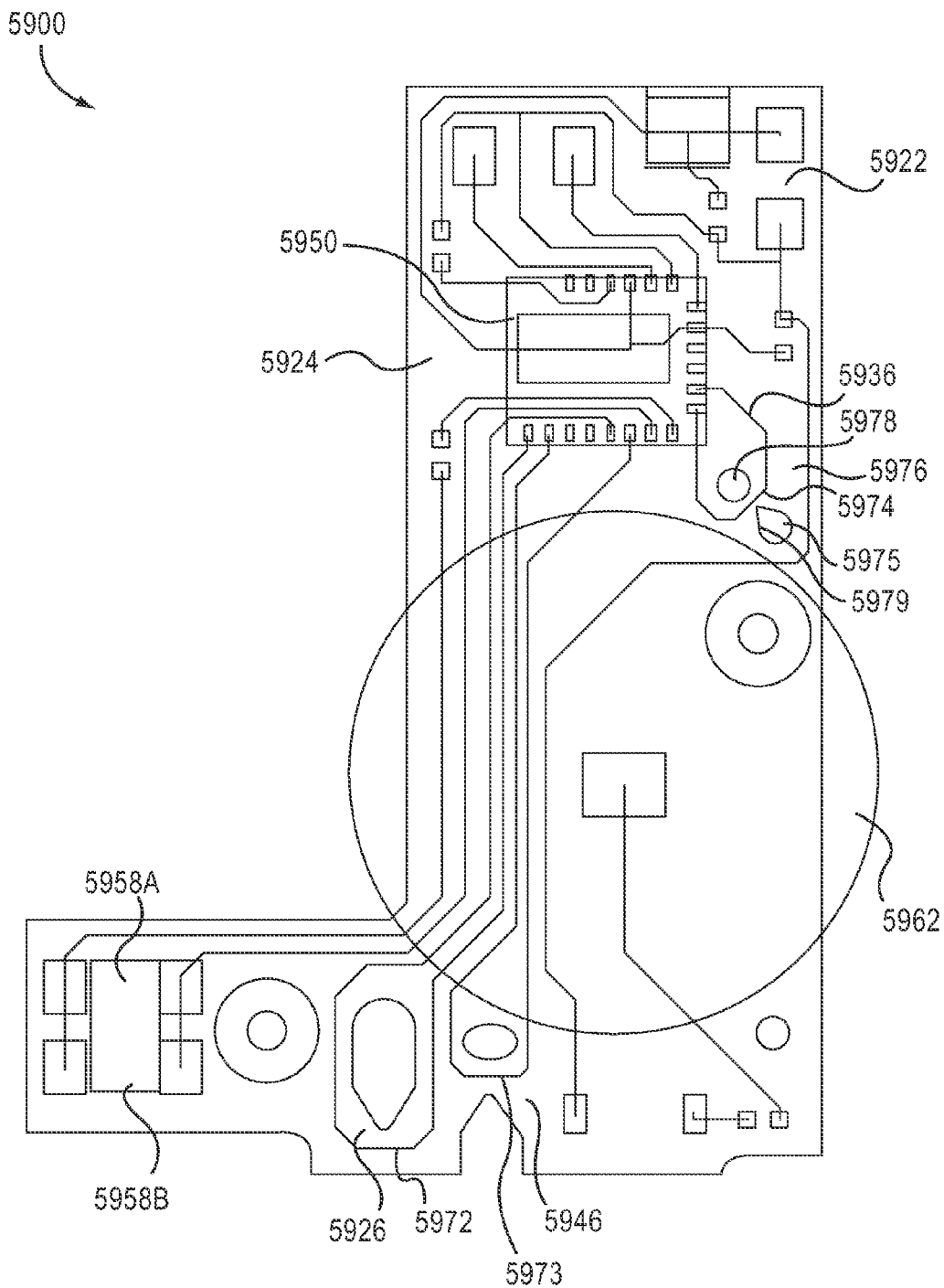
FIG. 37 is a back view of a printed circuit board of the electronic circuit system shown in FIG. 36.
Figure 38:
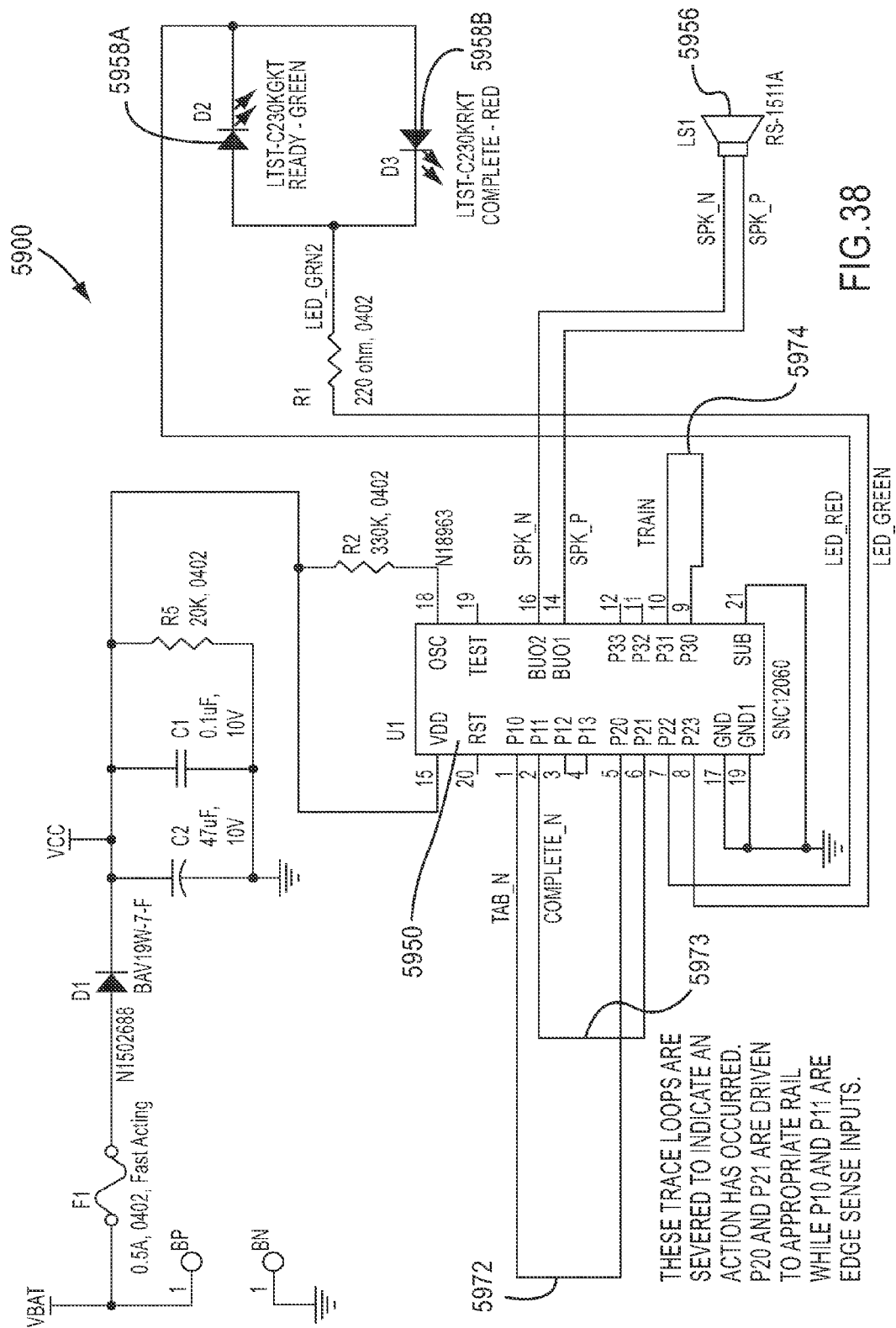
FIG. 38 is a schematic illustration of the electronic circuit system shown in FIG. 36.

FIG. 37 shows the printed circuit board 5922 of the electronic circuit system 5900. FIG. 38 is a schematic illustration of the electronic circuit system 5900. The printed circuit board 5922 of the electronic circuit system 5900 includes a substrate 5924, a first actuation portion 5926 (including a first switch 5972), a second actuation portion 5946 (including a second switch 5973), and a third actuation portion 5976 (including an electronic circuit system configuration switch 5974). The substrate 5924 of the printed circuit board 5922 includes the electrical components necessary for the electronic circuit system 5900 to operate as desired. For example, the electrical components can include resistors, capacitors, inductors, switches, microcontrollers, microprocessors and/or the like.

Figure 40:
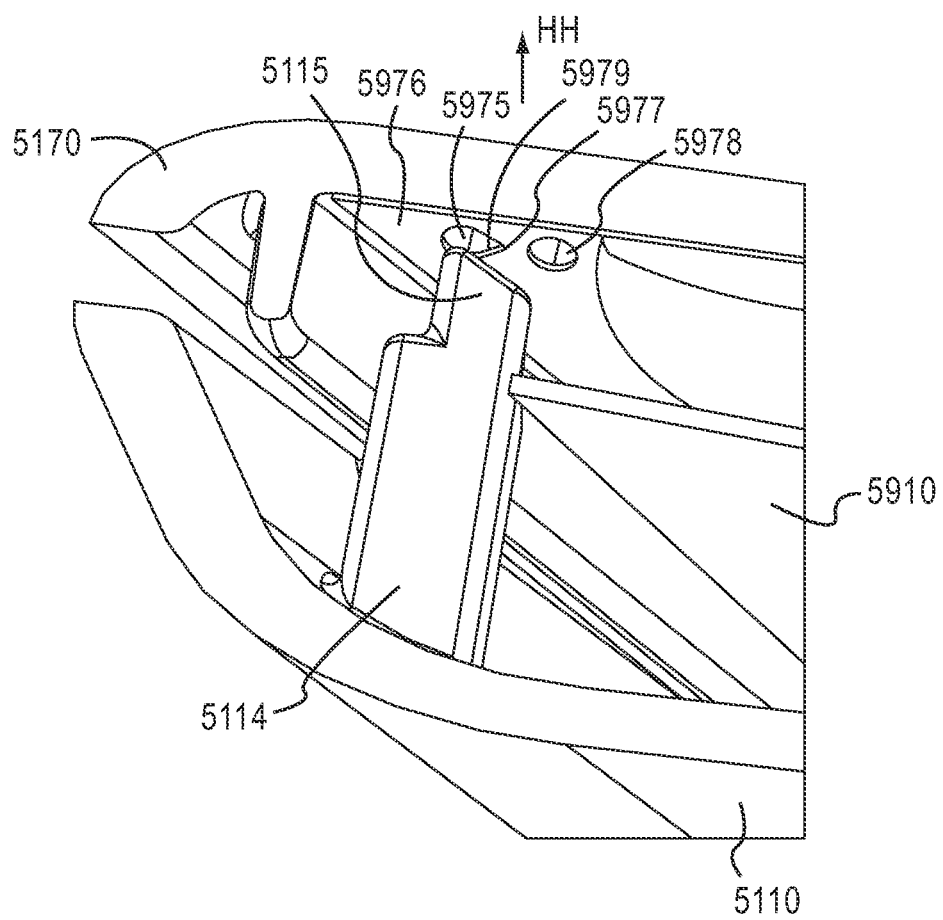
FIG. 40 is a cross-sectional perspective view of a portion of the electronic circuit system illustrated in FIG. 36, taken along line X-X in FIG. 39.

The first actuation portion 5926 and the second actuation portion 5946 are similar to the first actuation portion 4926 and the second actuation portion 4946 of the electronic circuit system 4900, described above (see e.g., FIG. 36), and are therefore not described or labeled in detail. The third actuation portion 5976 includes a third electrical conductor 5936 (see e.g., FIG. 37) and defines an actuation aperture 5975 having a boundary 5979, and a tear propagation limit aperture 5978. As shown in FIGS. 36 and 40, the actuation aperture 5975 of the third actuation portion 5976 is configured to receive the angled end portion 5115 of the actuation protrusion 5114 of the housing 5110 when the electronic circuit system 5900 is disposed within the electronic circuit system cavity 5153. The boundary 5979 of the actuation aperture 5975 has a discontinuous shape, such as, for example, a teardrop shape, that includes a stress concentration riser 5977. The discontinuity and/or the stress concentration riser 5977 of the boundary 5979 can be of any suitable shape to cause the substrate 5924 to deform in a predetermined direction when the angled end portion 5115 of the actuation protrusion 5114 of the housing 5110 is inserted into the actuation aperture 5975 (see e.g., FIG. 40), as described below.

The third electrical conductor 5936 includes the electronic circuit system configuration switch 5974 (see e.g., FIG. 37) disposed between the actuation aperture 5975 and the tear propagation limit aperture 5978, which can be, for example, a frangible portion of the third electrical conductor 5436. As shown in FIGS. 39 and 40, when the electronic circuit system 5900 is attached to the housing 5110, a portion of the angled portion 5115 of the actuation protrusion 5114 is disposed within the actuation aperture 5975 of the third actuation portion 5976, as shown by the arrow HH in FIG. 40. Continued movement of the angled portion 5115 of the actuation protrusion 5114 within the third actuation portion 5976 of the substrate 5924 causes the third actuation portion 5976 of the substrate 5924 to tear, thereby separating the portion of the third electrical conductor 5936 including the electronic circuit system configuration switch 5974. Said another way, when the electronic circuit system 5900 is attached to the housing 5110, the actuation protrusion 5114 moves irreversibly the electronic circuit system configuration switch 5974 from a first state (e.g., a state of electrical continuity) to a second state (e.g., a state of electrical discontinuity).

The tear propagation limit aperture 5978 is configured to limit the propagation of the tear in the substrate 5924. Said another way, the tear propagation limit aperture 5978 is configured to ensure that the tear in the substrate 5924 does not extend beyond the tear propagation limit aperture 5978. The tear propagation limit aperture 5978 can be any shape configured to limit the propagation of a tear and/or disruption of the substrate 5924. For example, the tear propagation limit aperture 5978 can be oval shaped. In other embodiments, the boundary of the tear propagation limit aperture 5978 can be reinforced to ensure that the tear in the substrate 5924 does not extend beyond the tear propagation limit aperture 5978. The angled end portion 5115 of the actuation protrusion 5114 ensures that the tear in the substrate 5924 propagates in the desired direction. Said another way, the angled end portion 5115 of the actuation protrusion 5114 ensures that the tear in the substrate 5924 occurs between the actuation aperture 5975 and the tear propagation limit aperture 5978.

When the actuation protrusion 5114 of the housing 5110 moves irreversibly the electronic circuit system configuration switch 5974 of the electronic circuit system 5900 from the first state to the second state, the electronic circuit system 5900 can be moved between a first configuration and a second configuration. For example, in some embodiments, irreversibly moving the electronic circuit system configuration switch 5974 of the electronic circuit system 5900 to the second state places the electronic circuit system 5900 in the second configuration such that when power is applied to the electronic circuit system 5900, the electronic circuit system 5900 recognizes that the medicament delivery device 5000 is a certain type of medicament delivery device and/or is in a certain configuration. In some embodiments, the housing can be devoid of the actuation protrusion 5114, thus the electronic circuit system configuration switch 5974 is maintained in its first state when the electronic circuit system 5900 is attached to the housing 5110. In this manner, the electronic circuit system configuration switch 5974 can enable the electronic circuit system 5900 to be used in different types and/or configurations of medicament delivery devices. The dual functionality of the electronic circuit system 5900 enables production of the same electronic circuit system 5900 for multiple devices, thereby permitting mass production and decreasing the cost of production of the electronic circuit system 5900.

For example, in some embodiments the electronic circuit system 5900 can be used in either an actual medicament delivery device or a simulated medicament delivery device.

Figure 41:
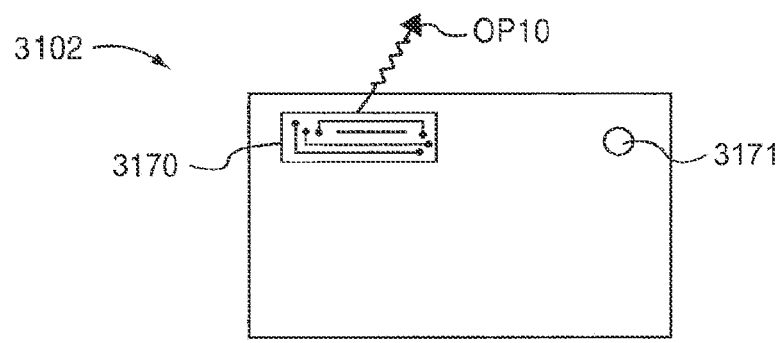
FIG. 41 is a schematic illustration of a simulated medicament delivery device according to an embodiment of the invention.

A simulated medicament delivery device can, for example, correspond to an actual medicament delivery device and can be used, for example, to train a user in the operation of the corresponding actual medicament delivery device. FIG. 41 is a schematic illustration of a simulated medicament delivery device 3102 according to an embodiment of the invention. In some embodiments, the simulated medicament delivery device 3102 can correspond to an actual medicament delivery device (i.e., a device actually configured to deliver a medicament, not shown in FIG. 41) and can be used, for example, to train a user in the operation of the corresponding actual medicament delivery device.

The simulated medicament delivery device 3102 includes an electronic circuit system 3170 configured to output an electronic output OP10 associated with the use of the simulated medicament delivery device 3102. As described herein, in some embodiments, for example, the electronic output OP10 can be associated with an identification of the simulated medicament delivery device 3102, an identification of certain components of the simulated medicament delivery device 3102 (e.g., a top portion, a safety lock, or the like), an identification of a physical condition for which a patient may require the medicament delivery device (not shown in FIG. 41) and/or an instruction for using the simulated medicament delivery device 3102 and/or the corresponding actual medicament delivery device (not shown in FIG. 41).

Moreover, the electronic output OP10 can include any type of electronic output and/or signal discussed herein, such as, for example, a visual output, an audible output and/or a haptic output. For example, in some embodiments, the electronic output OP10 can be a signal associated with an audible message (e.g., recorded speech) identifying the simulated medicament delivery device 3102. Such an audible message can state, for example, "You have removed an auto-injector trainer that will teach you how to use an actual auto-injector. This trainer does not contain any medicament. If this an actual emergency, please dial 911 or locate an actual auto-injector." In some embodiments, an audible output can instruct a user in the use of the simulated medicament delivery device 3102. Such an audible message can state, for example, "The first step in using an actual auto-injector is to identify the key features of the auto-injector. The key features of the auto-injector are the safety lock and the actuator button . . . " In other embodiments, the electronic output OP10 can be associated with a visual indicator that identifies one or more components of the simulated medicament delivery device 3102.

In some embodiments, the user can activate the electronic circuit system 3170 by pushing the start button 3171, which prompts the electronic circuit system 3170 to output at least the electronic output OP10. In some embodiments, for example, when the start button 3171 is actuated, the electronic circuit system 3170 can output a predetermined sequence of electronic outputs. As described above, in some embodiments, the start button 3171 can activate the electronic circuit system 3170 by providing an input to a processor (not shown in FIG. 41). In other embodiments, the start button 3171 can activate the electronic circuit system 3170 by placing a battery (not shown in FIG. 41) in electronic communication with a portion of the electronic circuit system 3170.

The simulated medicament delivery device 3102 can simulate the actual medicament delivery device in any number of ways. For example, in some embodiments, the simulated medicament delivery device 3102 can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device 3102 can include components that correspond to the components of the actual medicament delivery device. In this manner, the simulated medicament delivery device 3102 can simulate the look, feel and sounds of the actual medicament delivery device. For example, in some embodiments, the simulated medicament delivery device 3102 can include external components (e.g., a housing, a needle guard, a sterile cover, a safety lock or the like) that correspond to external components of the actual medicament delivery device. In some embodiments, the simulated medicament delivery device 3102 can include internal components (e.g., an actuation mechanism, a compressed gas source, a medicament container or the like) that correspond to internal components of the actual medicament delivery device.

In some embodiments, however, the simulated medicament delivery device 3102 can be devoid of a medicament and/or those components that cause the medicament to be delivered (e.g., a needle, a nozzle or the like). In this manner, the simulated medicament delivery device 3102 can be used to train a user in the use of the actual medicament delivery device without exposing the user to a needle and/or a medicament. Moreover, the simulated medicament delivery device 3102 can have features to identify it as a training device to prevent a user from mistakenly believing that the simulated medicament delivery device 3102 can be used to deliver a medicament. For example, in some embodiments, the simulated medicament delivery device 3102 can be of a different color than a corresponding actual medicament delivery device. Similarly, in some embodiments, the simulated medicament delivery device 3102 can include a label clearly identifying it as a training device.

The simulated medicament delivery device 3102 can simulate any number of medicament delivery devices. For example, in some embodiments, the simulated medicament delivery device 3102 can simulate a medical injector, such as an auto-injector, a pen injector or the like. In other embodiments, the simulated medicament delivery device 3102 can simulate an inhaler. In yet other embodiments, the simulated medicament delivery device 3102 can simulate a transdermal delivery device.

In some embodiments, the simulated medicament delivery device 3102 can repeatedly simulate the actual medicament delivery device. For example, in some embodiments, after the simulation is complete the electronic circuit system can be reset, for example, by pushing the start button 3171. In this manner, the simulated medicament delivery device 3102 can be configured to repeat the electronic output OP10 or predetermined sequence of electronic outputs during subsequent simulations.

Figure 42:
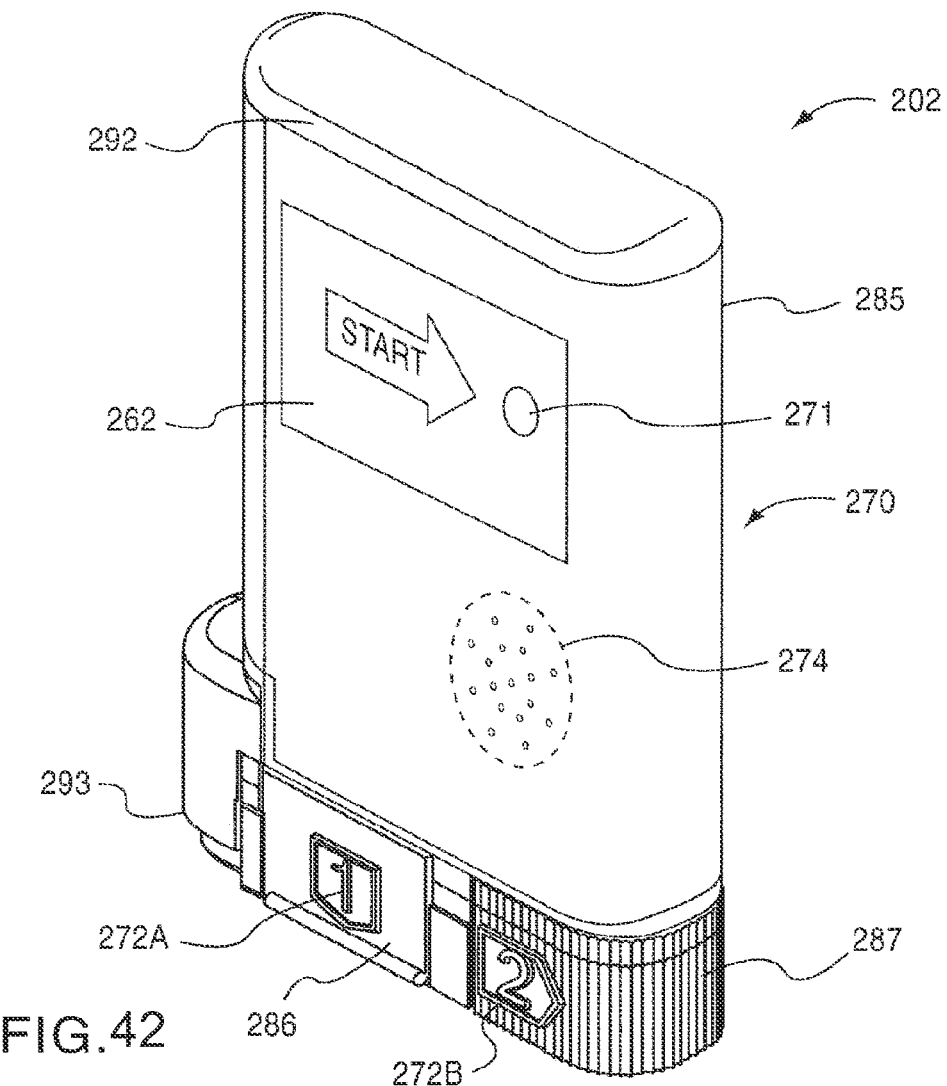
FIG. 42 is a perspective view of a simulated auto-injector according to an embodiment of the invention.
Figure 43:
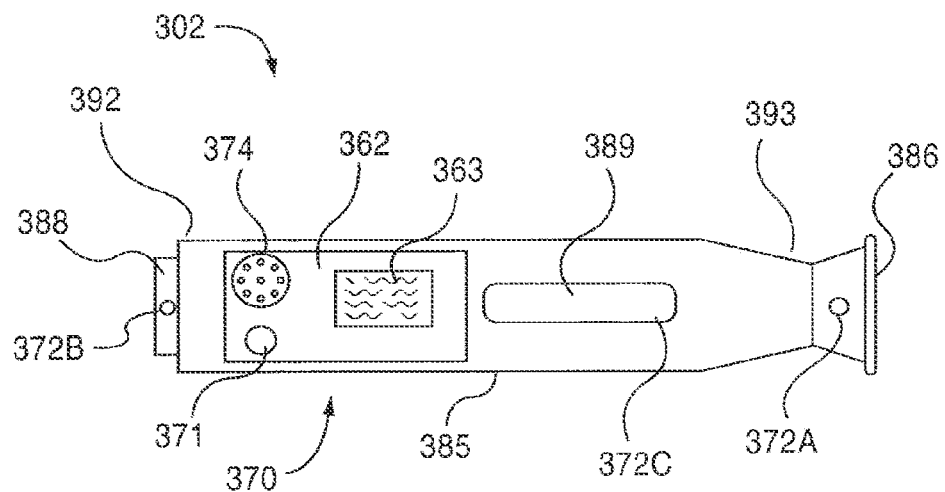
FIGS. 43-47 are front are front views of a simulated auto-injector according to an embodiment of the invention, in a first configuration, second configuration, third configuration, fourth configuration and fifth configuration, respectively.

FIG. 42 is a perspective view of a simulated auto-injector 202 according to an embodiment of the invention. The simulated auto-injector 202 is configured to simulate an auto-injector (not shown in FIG. 42) similar to the auto-injectors described herein and in U.S. patent application Ser. No. 11/562,061, entitled "Devices, Systems and Methods for Medicament Delivery," filed Nov. 21, 2006, which is incorporated herein by reference in its entirety.

The simulated auto-injector 202 includes a housing 285 having a proximal end portion 292 and a distal end portion 293. A simulated needle guard assembly 286 is removably coupled to the distal end portion 293 of the housing 285. The simulated needle guard assembly 286 is configured to simulate an actual needle guard assembly. Similarly, a simulated safety lock 287 is removably coupled to the distal end portion 293 of the housing 285. The simulated safety lock 287 is configured to simulate an actual safety lock.

The simulated auto-injector 202 includes an electronic circuit system 270 and a label 262. The label 262 can be any suitable label of the type described herein. In some embodiments, for example, the label 262 can include at least a portion of the electronic circuit system 270 (i.e., portions of an electronic conductors, portions of a printed circuit board, a battery, an LED or the like). In other embodiments, the label 262 can be devoid of any portion of the electronic circuit system 270.

The electronic circuit system 270 includes a start button 271, a speaker 274 and two LEDs 272A, 272B. The electronic circuit system 270 can be any electronic circuit system of the type shown and described herein. For example, in some embodiments, the electronic circuit system 270 can include a flexible printed circuit board to electronically coupled the components contained therein. Moreover, the electronic circuit system 270 can be disposed in any suitable manner relative to the housing 285. In some embodiments, for example, the electronic circuit system 270 can be integrated with the simulated medicament delivery device 202. Said another way, in some embodiments, the electronic circuit system 270 can be contained within the housing 285 and/or the electronic circuit system 270 can be assembled concurrently and/or using common processes with the simulated medicament delivery device 202. In other embodiments, the electronic circuit system 270 can be partially-integrated with the simulated medicament delivery device 202. Said another way, in some embodiments, at least a portion of the electronic circuit system 270 can be contained within the housing 285 and/or at least a portion of the electronic circuit system 270 can be assembled concurrently and/or using common processes with the simulated medicament delivery device 202. In yet other embodiments, the electronic circuit system 270 can be disposed entirely on an outer surface of the housing 285 and/or the electronic circuit system 270 can be assembled using separate processes from those used to manufacture the simulated medicament delivery device 202. In some embodiments, for example, the electronic circuit system can be included in the label 262. In other embodiments, the label 262 can be used to secure the electronic circuit system to an outer portion of the housing 285.

To activate the electronic circuit system 270, the user first pushes the start button 271. As described above, when actuated, the electronic circuit system 270 can output one or more electronic outputs. For example, in some embodiments, an electronic output can be associated with an audio and/or a visual output used to describe the features of and/or identify component of the simulated medicament delivery device 202. For example, in some embodiments, the first LED 272A, the output of which is shaped as the numeral "1," can output a flashing light of a first color while the speaker 274 simultaneously outputs a recorded voice message stating "the simulated needle guard is identified by the FIRST COLOR flashing light shaped as the numeral one." Similarly, the second LED 272BA, the output of which is shaped as the numeral "2," can output a flashing light of a second color different than the first color while the speaker 274 simultaneously outputs a recorded voice message stating "the simulated safety lock is identified by the SECOND COLOR flashing light shaped as the numeral two." In this manner, the electronic circuit system 270 can provide both audible and visual instructions to assist the user in the operation of the simulated medicament delivery device 202.

In some embodiments, the electronic circuit system 270 can output at least one electronic output in response to a switch (not shown in FIG. 42) being moved between a first state and a second state. For example, the simulated needle guard assembly 286 can include an actuator configured to actuate a switch contained within the electronic circuit system 270. The switch can be any suitable switch of the types shown and described above. For example, in some embodiments, a switch can be a "tear-through" switch configured to move irreversibly from a first state to a second state. In other embodiments, a switch can be a microswitch configured to repeatedly move between a first state and a second state. In this manner, the electronic circuit system 270 can output instructions when the user moves the simulated needle guard assembly 286 relative to the housing 285. Such instructions can state, for example, "You have now removed the needle guard assembly. The next step is to remove the safety lock. Please pull the safety lock as indicated by the flashing arrow."

In a similar manner, the simulated safety lock 287 can include an actuator configured to actuate a switch contained within the electronic circuit system.

Although the simulated medicament delivery device 202 is shown as including a start button 271 to activate the electronic circuit system (not shown in FIG. 42), in other embodiments, an electronic circuit system 270 can be activated by any suitable means. For example, in some embodiments, the electronic circuit system can be activated by removing the simulated needle guard assembly 286, as described above. In other embodiments, the electronic circuit system 270 can be activated by removing the simulated safety lock 287. In yet other embodiments, the electronic circuit system 270 can be activated by removing the simulated medicament delivery device 202 from a container (not shown in FIG. 42).

FIGS. 43-47 are front views of a simulated auto-injector 302 according to an embodiment of the invention. The simulated auto-injector 302 includes a housing 385 having a proximal end portion 392 and a distal end portion 393. The housing defines a window 389, which can, for example, simulate a status window of a corresponding actual auto-injector (not shown in FIGS. 43-47), as described below. A simulated needle guard assembly 386 is removably coupled to the distal end portion 393 of the housing 385. Similarly, a simulated safety lock 387 is disposed at the distal end portion 393 of the housing (see FIG. 44). The proximal end portion 392 of the housing 385 includes a simulated injector actuation button 388. The simulated injector actuation button 388 is configured to simulate an actuation button of the corresponding auto-injector.

The simulated auto-injector 302 includes an electronic circuit system 370 and a label 362. The label 362 can include a textual indicia 363 and can be any suitable label of the type described herein. In some embodiments, for example, the label 362 can include at least a portion of the electronic circuit system 370 (i.e., portions of an electronic conductor, portions of a printed circuit board, a battery, an LED or the like). In other embodiments, the label 362 can be devoid of any portion of the electronic circuit system 370.

The electronic circuit system 370 includes a start button 371, a speaker 374 and three visual output devices 372A, 372B and 372C. The visual output devices 372A, 372B and 372C can be, for example, LEDs, LCDs, organic polymer devices and/or fiber optic devices. The electronic circuit system 370 also includes a force sensor 377 (shown in FIG. 44) and a position sensor (not shown in FIGS. 43-47). The above described components can be electronically coupled together by any suitable mechanism, such as, for example a printed circuit board of the types shown and described herein.

As described above, to activate the electronic circuit system 370, the user pushes the start button 371. When actuated, the electronic circuit system 370 can output one or more electronic outputs. For example, in some embodiments, the first visual output device 372A can output a flashing light while the speaker 374 simultaneously outputs a recorded voice message stating "Please remove the simulated needle guard, which is at the end of the injector as indicated by the flashing light."

Figure 44:
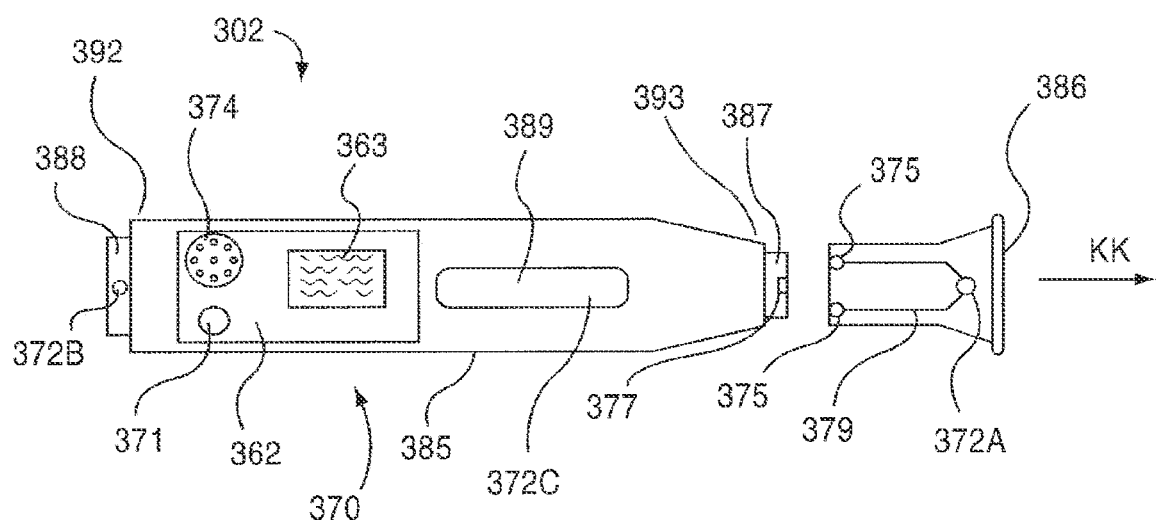

As illustrated by arrow KK in FIG. 44, the simulated needle guard 386 is removed by moving it along the longitudinal axis of the housing 385. When the simulated needle guard 386 is removed, the portion of the electronic circuit system 370 that includes the first visual output device 372A is no longer electronically coupled to the remainder of the electronic circuit system 370. Accordingly, the first visual output device 372A becomes deactivated when the simulated needle guard 386 is removed. Moreover, the terminals 375 of the electronic conductors 379 can form a portion of a switch, such that when the simulated needle guard 386 is removed, the switch changes from a first state to a second state, thereby prompting the electronic circuit system 370 to output an additional electronic output. For example, in some embodiments, the speaker 374 can output a recorded voice message stating "Please place the simulated auto-injector against your thigh. Do not tilt the simulated auto-injector. When in the proper position, please press firmly against the thigh before actuating the auto-injector."

In addition to prompting the electronic circuit system 370 to output additional visual and/or audible outputs, the removal of the simulated needle guard 386 can also activate the position sensor (not shown in FIGS. 43-47). The position sensor can be any suitable sensor for sensing a position, location and/or orientation of the simulated auto-injector 302. For example, in some embodiments, the position sensor can be configured to sense the angle Θ between the longitudinal axis of the housing 385 and the surface of the target T (see FIG. 45). In other embodiments, the position sensor can be configured to sense the absolute angle of the longitudinal axis of the housing based on gravity. In yet other embodiments, the position sensor can be capacitance sensor, a temperature sensor, an optical sensor or any other suitable sensor for determining when the distal end 393 of the simulated medicament delivery device 302 is in contact with the target T. In this manner, the position sensor can provide feedback to the user to ensure that the simulated medicament delivery device 302 is correctly positioned relative to the target T.

Figure 45:
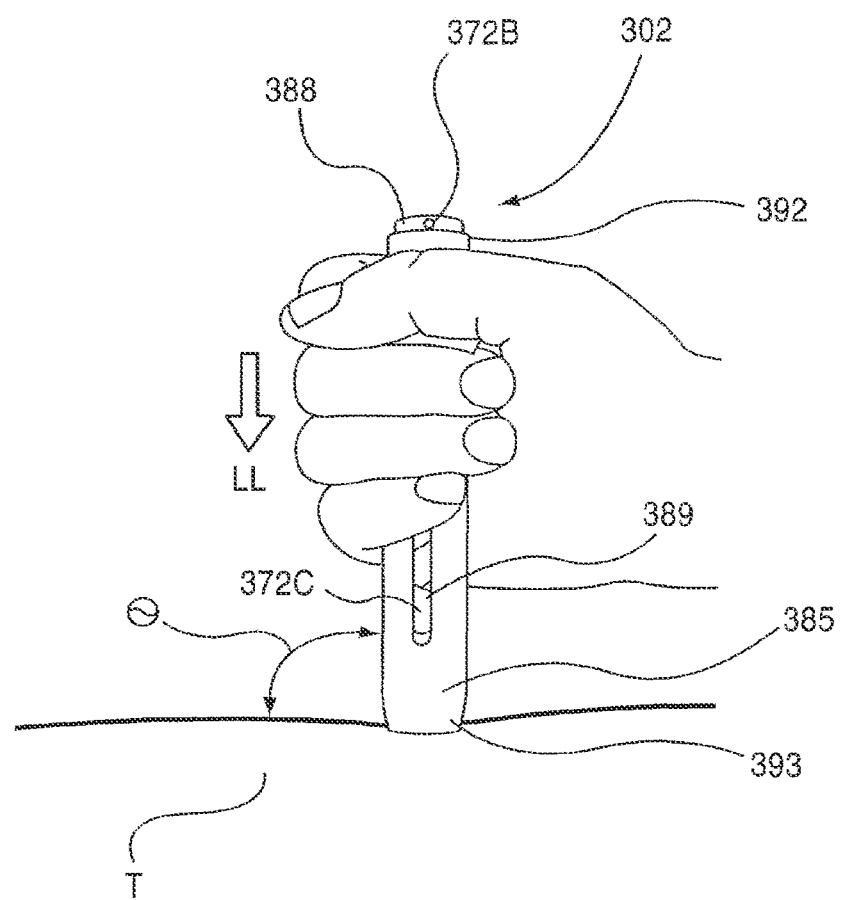
Figure 46:
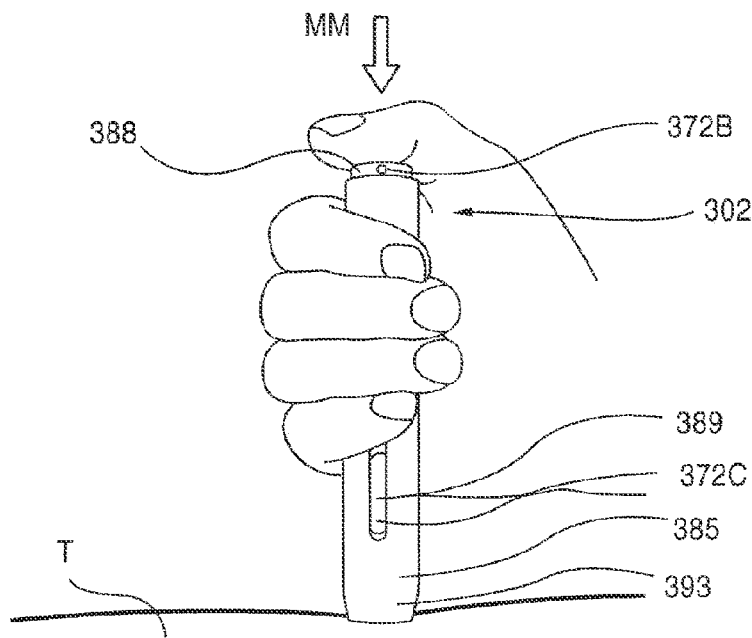

Similarly, when the user presses the simulated medicament delivery device 302 against the target T, as shown by the arrow LL in FIG. 45, the force sensor 377 can sense the force and/or pressure between the target T and the simulated safety lock 387. In this manner, the force sensor 377 can provide feedback to the user to ensure that the simulated medicament delivery device 302 is pressed against the target T with sufficient force to move the safety lock of an actual medicament delivery device (not shown in FIGS. 43-47). The force sensor 377 can also provide feedback to the user to ensure that the simulated medicament delivery device 302 is not pressed too firmly against the target T. The force sensor 377 can be any sensor suitable for sensing a force and/or pressure, such as for example, a strain-gauge load sensor, a piezo-electric sensor or the like.

In some embodiments, after the simulated medicament delivery device 302 is correctly positioned with sufficient force against the target T, the force sensor 377 can prompt the electronic circuit system 370 to output an additional electronic output or sequence of electronic outputs. For example, in some embodiments, the second visual output device 372B can output a flashing light while the speaker 374 simultaneously outputs a recorded voice message stating "The simulated auto-injector is now correctly positioned against your body. Please press the injector actuation button at the top of the auto-injector as indicated by the flashing light."

In some embodiments, the electronic circuit system 370 can include a timer (not shown in FIGS. 43-47) to determine the duration of any of the various operations discussed herein. In this manner, the electronic circuit system 370 can repeat a previous electronic output if no action has been sensed within a predetermined amount of time. For example, in some embodiments, the electronic circuit system 370 can repeat the electronic output prompting the user to remove the simulated needle guard 386 if a predetermined time period has elapsed after the start button 371 is pushed and before the simulated needle guard 386 is removed. In some embodiments, the electronic circuit system 370 can augment the electronic output prompting the user to remove the simulated needle guard 386 if a predetermined time period has elapsed after the start button 371 is pushed and before the simulated needle guard 386 is removed. The electronic output can be augmented, for example, by automatically increasing the volume of the audible output, changing the characteristics (e.g., the color, flash rate or the like) of the visual outputs or the like.

In other embodiments, the electronic circuit system 370 can output an electronic output to instruct the user to move to the next operation after a predetermined amount of time has elapsed. For example, in some embodiments, the speaker 374 can output a recorded voice message stating "Release the actuation button. Do not continue to hold the actuation button down" when the duration between when the user presses the simulated injector actuation button 388 (as shown by arrow MM in FIG. 46) and when the user releases the simulated injector actuation button 388 (as shown by arrow NN in FIG. 47) exceeds a predetermined duration. In this manner, the electronic circuit system 370 can provide feedback to the user to ensure that the simulated medicament delivery device 302 is used properly.

Figure 47:
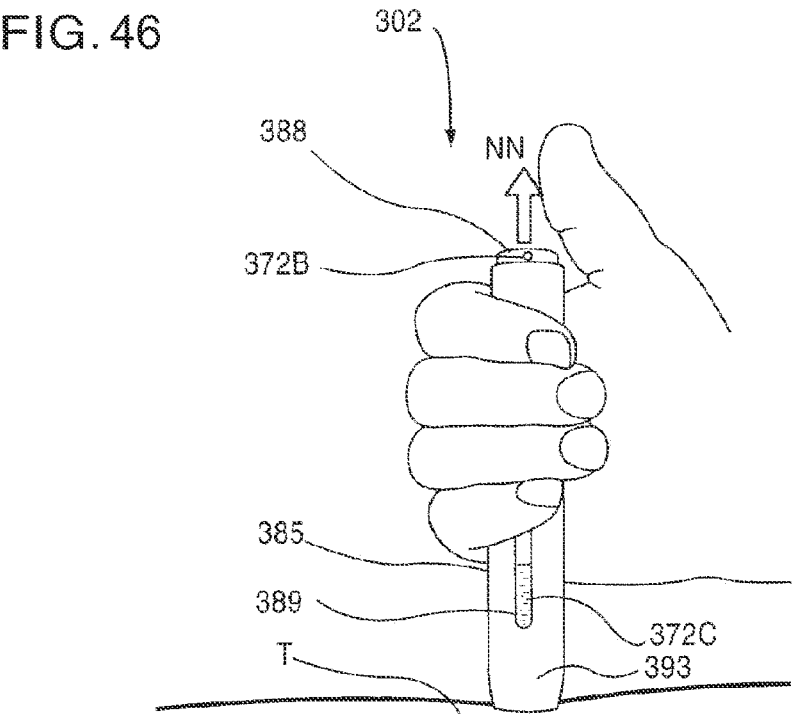

As shown in FIG. 47, the third visual output device 372C is visible through the window 389 defined by the housing 385. In some embodiments, the third visual output device 372C and the window 389 can collectively simulate a status window of the actual medicament delivery device (not shown in FIG. 47). For example, in some embodiments, the third visual output device 372C can gradually change color to simulate an associated color change of a status window that alerts a user when an actual injection is complete.

Although the simulated medicament delivery devices are shown and described as including external components and/or internal components to simulate actual medicament delivery devices, in some embodiments, a simulated medicament delivery device can be devoid of certain components, such as, for example, springs, actuation mechanisms or the like. For example, in some embodiments, a simulated medicament delivery device can include an electronic circuit system configured to output an electronic output to simulate any one of a tactile sensation, an audible sensation, a visual sensation, an olfactory sensation and/or a taste sensation associated with a use of the medicament delivery device. In this manner, the simulated medicament delivery device can simulate a medicament delivery device without mechanical components and/or medicament, which can be make the simulated medicament delivery device expensive, unsafe to use, difficult to use, difficult to reset for repeated use or the like.

Figure 48:
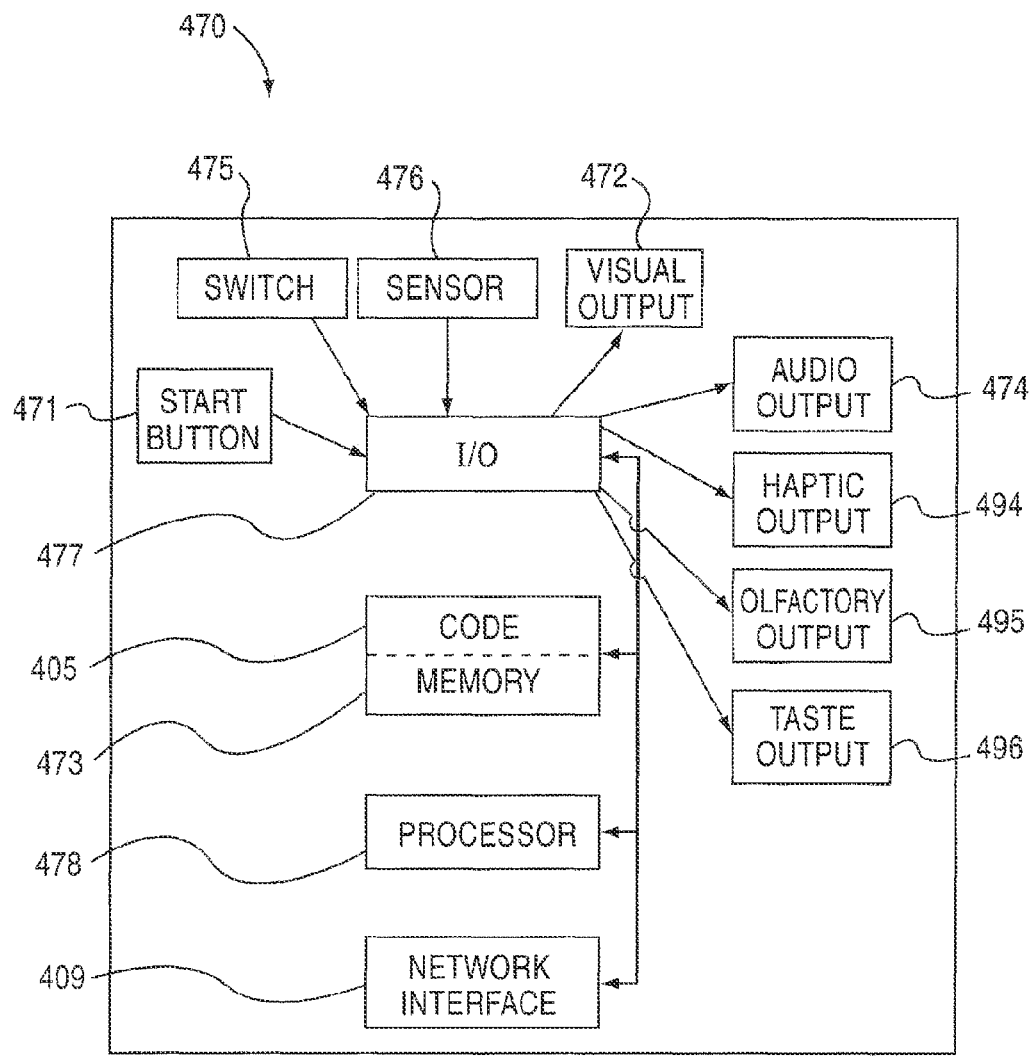
FIG. 48 is a schematic illustration of a medical device according to an embodiment of the invention.

FIG. 48 is a schematic illustration of an electronic circuit system 470 according to an embodiment of the invention configured to cooperate with a housing (not shown in FIG. 48) to simulate a medicament delivery device (not shown in FIG. 48). The electronic circuit system 470 includes a processor 478 operatively coupled to a memory device 473. The memory device 473 can be configured to store processor-readable code 405 instructing the processor 478 to perform the functions described herein. In some embodiments, the processor-readable code 405 can be modified and/or updated as circumstances dictate.

The electronic circuit system 470 includes an input/output device 477 configured to receive electronic inputs from a switch 475 and/or a sensor 476, as described above. In some embodiments, the input/output device 477 can receive inputs from any suitable device, such as an RFID tag (as described above), the user's voice (e.g., through a microphone), a start button 471 or the like. The input/output device 477 is also configured to output electronic signals to various output devices, such as, for example, a visual output device 472, an audio output device 474, a haptic output device 494, an olfactory output device 495, a taste output device 496, a wireless receiver (e.g., an RFID tag, a cellular phone system or the like) and/or a wired receiver (e.g., a wired network).

The visual output device 472 can be any suitable device for producing visual indicia, such as, light-emitting diodes (LEDs), liquid-crystal display (LCD) screens, optical polymers, fiber optic components or the like. In this manner, the electronic circuit system 470 can simulate a particular visual feature of a medicament delivery device, such as, for example, a change in the color of a status window.

Similarly, the audio output device 474 can be any suitable device for producing sound, such as a micro-speaker, a piezo-electric transducer or the like. Such audible output can include, for example, an alarm, a series of beeps, recorded speech or the like. In this manner, the electronic circuit system 470 can simulate a particular audible feature of a medicament delivery device, such as, for example, a series of clicks associated with the actuation of the medicament delivery device and/or the delivery of the medicament.

The haptic output device 494 can be any suitable device for producing a haptic output, such as a vibrator, a piezo-electric device, a heater, a cooler or the like. In this manner, the electronic circuit system 470 can simulate a particular feel of a medicament delivery device. For example, in some embodiments, a simulated medicament delivery device can be configured to simulate a transdermal medicament delivery device by simulating the thermal feel of a medicament delivery area against the skin. In other embodiments, a simulated medicament delivery device can be configured to simulate an auto-injector by simulating the vibration associated with the actuation of the auto-injector.

The olfactory output device 495 can be any suitable device for producing a scent output. In this manner, the electronic circuit system 470 can simulate a particular smell associated with a medicament delivery device. For example, in some embodiments, a simulated medicament delivery device can be configured to simulate an inhaler by simulating the smell of a medicament as it is being delivered orally.

Similarly, the taste output device 495 can be any suitable device for producing a simulated taste. In this manner, the electronic circuit system 470 can simulate a particular taste associated with a medicament delivery device. For example, in some embodiments, a simulated medicament delivery device can be configured to simulate an inhaler by simulating the taste of a medicament as it is being delivered orally.

In some embodiments, the electronic circuit system 470 can include a network interface 409 configured to operatively couple the electronic circuit system 470 to a remote device (not shown in FIG. 48), as described above. The network interface 409 can also be configured to transmit information from the electronic circuit system 470 to a central network, such as, for example, a doctor's office, as described above.

Referring back to FIG. 38, the actuation of the medicament delivery device configuration switch 5974 can configure the electronic circuit system 5900 to output a different electronic output when the medicament delivery device 5000 is a simulated medical injector than when the medicament delivery device 5000 is an actual medical injector. Said yet another way, the electronic circuit system 5900 can be configured to output a first series of electronic outputs when the electronic circuit system configuration switch 5974 is in the first state and a second series of electronic outputs when the electronic circuit system configuration switch 5974 is in the second state. In this manner, the electronic circuit system configuration switch 5974 can enable the same electronic circuit system 5900 to be used in both simulated medicament delivery devices and actual medicament delivery devices. When used on an actual medicament delivery device, for example, the housing can be devoid of the actuation protrusion 5114. The dual functionality of the electronic circuit system 5900 can decrease the cost of production of the electronic circuit system 5900 of the medicament delivery device 5000.

In other embodiments, moving the electronic circuit system configuration switch 5974 to the second state can place the electronic circuit system 5900 in any number of different functional configurations. For example, moving the electronic circuit system configuration switch 5974 from the first state to the second state can indicate the type of medicament in the medicament container, the dosage of the medicament and/or the language of the audible electronic outputs output by the electronic circuit system 5900.

In still other embodiments, any number of electronic circuit system configuration switches can be used. For example, multiple switches can be used to configure the electronic circuit system 5900 to output usage instructions in any number of languages. For example, if an electronic circuit system contained three configuration switches (e.g., switches A, B and C), switch A can correspond to English instructions, switch B to Spanish instructions and switch C to German instructions. Further, moving both switch A and B to the second state might correspond to French instructions. In this manner, a single electronic circuit system 5900 can be configured to output instructions in multiple languages.

Figure 49:
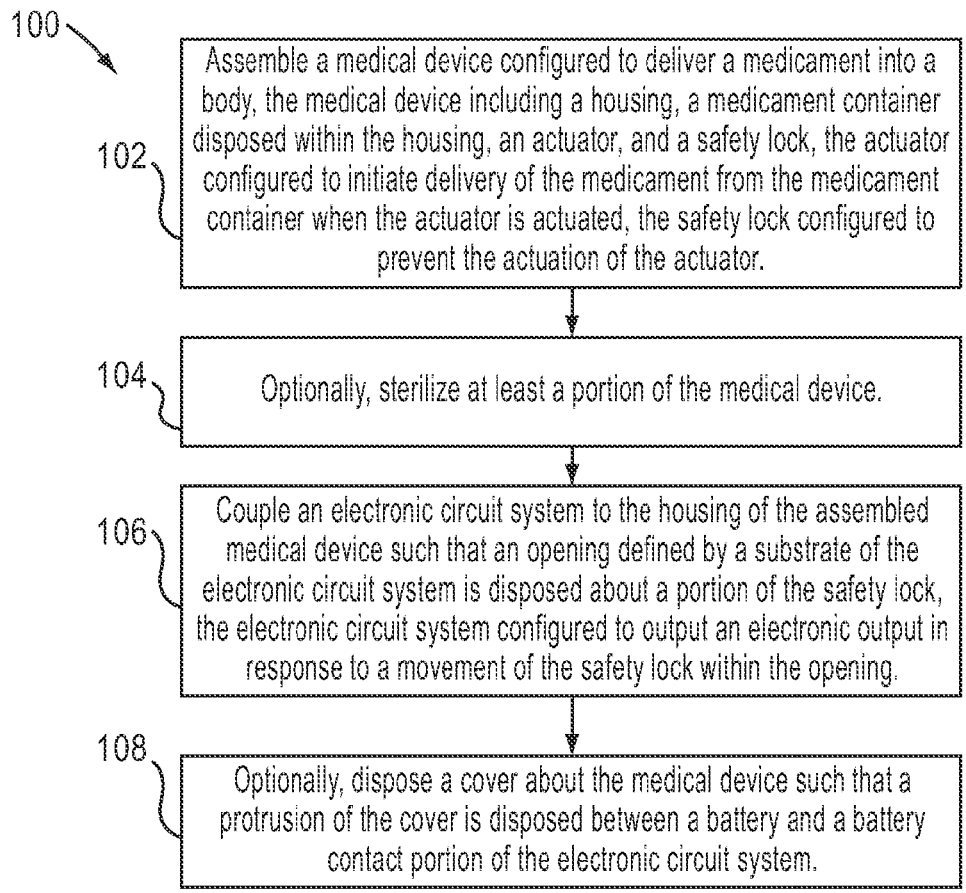
FIG. 49 is a flow chart illustrating a method of assembling a medical injector according to an embodiment of the invention.

FIG. 49 is a flow chart of a method 100 according to an embodiment of the invention. The method includes assembling a medical device configured to deliver a medicament into a body of a patient, 102. The medical device includes a housing, a medicament container disposed within the housing, an actuator, and a safety lock. In some embodiments, the housing, medical container, the actuator, and the safety lock can be similar to the corresponding components in the medical injector 4000 and/or the medicament delivery device 5000, described above. The actuator of the medical device is configured to initiate delivery of the medicament from the medicament container when the actuator is actuated. The safety lock of the medical device is configured to prevent actuation of the actuator.

After the medical device is assembled, at least a portion of the medical device can optionally be sterilized, 104. Various sterilization techniques may be utilized. In some embodiments, a suitable sterilization technique includes the use of one or more of ethylene oxide, gamma radiation, e-beam radiation, ultraviolet radiation, steam, plasma, or hydrogen peroxide. In some embodiments, the needle is sterilized prior to installing the needle cover. In some embodiments, the needle is sterilized after the needle cover is installed. For example, in some embodiments, the needle cover is installed and then a gas sterilant is conveyed through at least a portion of the needle cover. The needle is sterilized using a gas sterilization technique that can penetrate one or more pores of a porous needle cover. In some embodiments, the needle can be sterilized using a gas sterilization technique that can penetrate one or more pores of a porous needle cover, but that will not react with a medicament in a medicament container disposed in the housing.

An electronic circuit system is then coupled to the housing of the assembled medical device, 106. The electronic circuit system is coupled to the housing such that an opening defined by a substrate of the electronic circuit system is disposed about a portion of the safety lock. The electronic circuit system is configured to output an electronic output in response to a movement of the safety lock within the opening. In some embodiments, for example, the electronic circuit system can be similar to the electronic circuit system 4900 of the medical injector 4000 and/or the electronic circuit system 5900 of the medicament delivery device 5000, as described above. In some embodiments, the electronic output can be, for example, a visual output, an audible output, and/or a haptic output, such as those described above. In other embodiments, the electronic output can be a wireless signal configured to be received by a remote device.

After the electronic circuit system is coupled to the housing, a cover can optionally be disposed about the medical device, 108. The cover can have a protrusion disposed between a battery and a battery contact portion of the electronic circuit system. In some embodiments, for example, the cover can be similar to the cover 4200 of the medical injector 4000 and/or the cover 5200 of the medical injector 5000.

Figure 50:
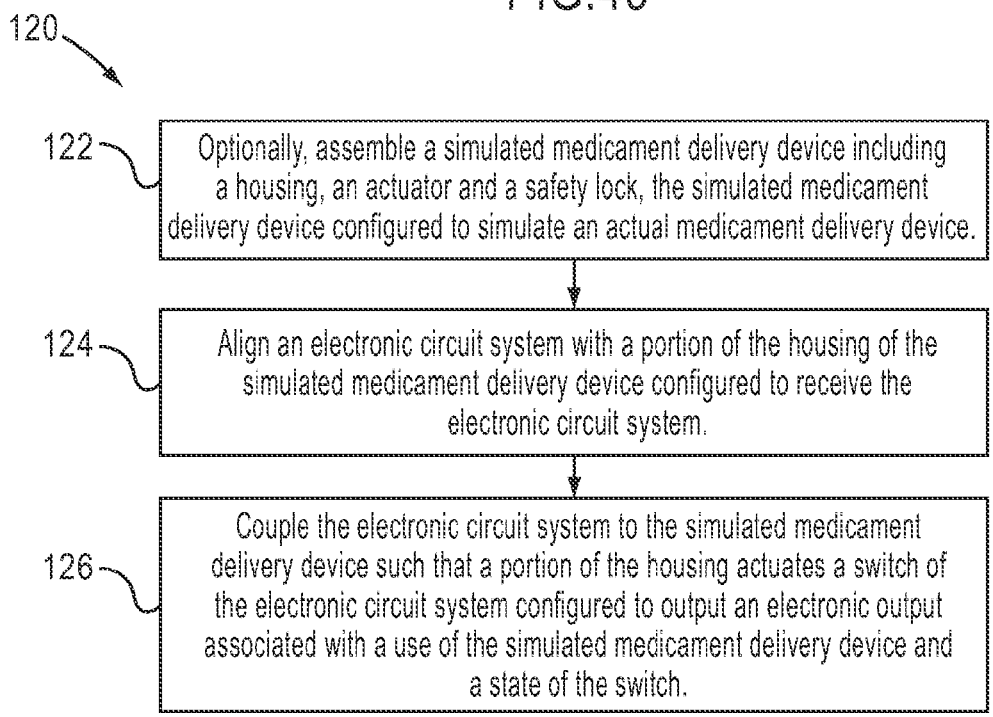
FIG. 50 is a flow chart illustrating a method of assembling a simulated medical injector according to an embodiment of the invention.

FIG. 50 is a flow chart of a method 120 according to an embodiment of the invention. The method includes optionally assembling a simulated medicament delivery device, 122. The medicament delivery device can include a housing, an actuator and a safety lock. The simulated medicament delivery device is configured to simulate an actual medicament delivery device. An electronic circuit system is then aligned with a portion of the housing configured to receive the electronic circuit system, 124. Aligning the electronic circuit system with the housing ensures that portions of the housing align with corresponding portions of the electronic circuit system. If the corresponding portions do not align, a number of issues can arise. For example, the electronic circuit system may not function correctly and/or the electronic circuit system may be damaged as a result of improper alignment.

The electronic circuit system is then coupled to the simulated medicament delivery device such that a portion of the housing actuates a switch of the electronic circuit system, 126. The electronic circuit system is configured to output an electronic output associated with a use of the simulated medicament delivery device and a state of the switch. The switch can be similar to the electronic circuit system configuration switch 5974 of the medicament delivery device 5000. For example, the electronic circuit system can output a first electronic output associated with a use of the simulated medicament delivery device when the switch is in a first state and a second electronic output associated with a use of the simulated medicament delivery device when the switch is in a second state. In some embodiments, the electronic output can be, for example, a visual output, an audible output, and/or a haptic output, such as those described above. In other embodiments, the electronic output can be a wireless signal configured to be received by a remote device. As described above, any number of switches can be disposed on the electronic circuit system.

Figure 51:
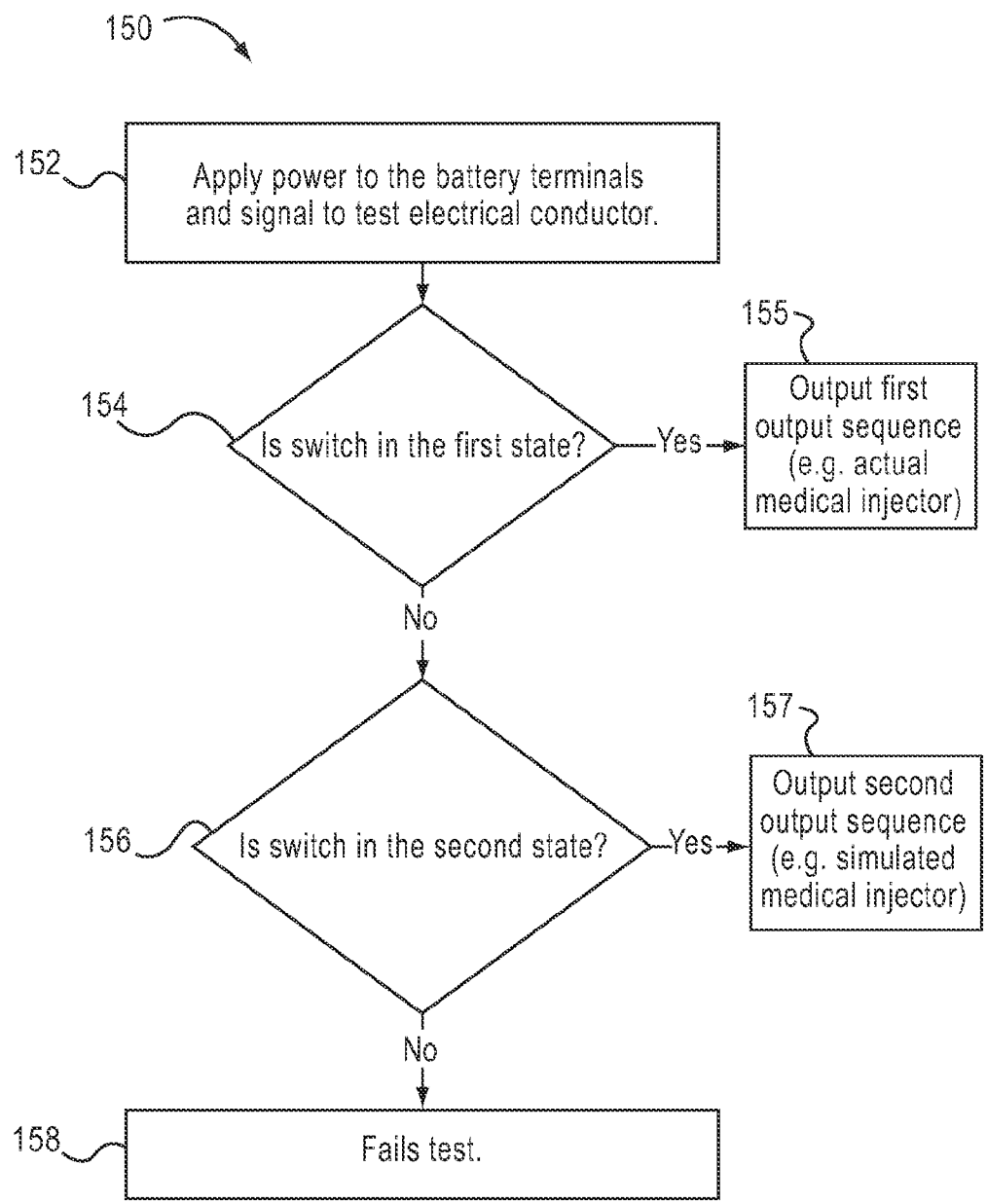
FIG. 51 is a flow chart illustrating a method of testing a medical injector according to an embodiment of the invention.

In some embodiments, an electronic self-test can be used to verify the integrity of an electronic circuit system and/or the switches of a medicament delivery device. FIG. 51 is a flow chart of a self-test method 150 that can be administered to ensure that a switch of the electronic circuit system is in the proper state (i.e., a state that corresponds to the configuration of the medicament delivery device). For example, in some embodiments the method 150 can ensure that the electronic circuit system configuration switch is in the correct state (i.e., a first state if the medicament delivery device is an actual medicament delivery device or a second state if the medicament delivery device is a simulated medicament delivery device). The method includes applying power to the battery terminals, 152 and thus the electronic circuit system. If the electronic circuit system configuration switch is in the first state, 154, the electronic circuit system will output a first output sequence, 155. For example, the first output sequence can consist of the LEDs blinking in a first predetermined sequence (e.g., green-red-green) followed by an audible output. The first output sequence can indicate that the medicament delivery device is an actual medicament delivery device and not a simulated medicament delivery device. If the electronic circuit system configuration switch is in the second state, 156, the electronic circuit system will output a second output sequence, different than the first, 157. For example, the second output sequence can consist of the LEDs blinking in a second predetermined sequence (e.g., red-green-green) followed by an audible output. The second output sequence can indicate that the medicament delivery device is a trainer. If neither the first output sequence or the second output sequence occurs, the medicament injector has failed the test, 158, indicating that an error exists within the electronic circuit system.

In other embodiments, different electronic output sequences can be used to indicate and/or test different modes of the medical injector. For example, the LEDs could blink in a third sequence to indicate a Spanish medical injector. Additionally, any number of self tests can be used to determine the state of each switch of the electronic circuit system. Further, the integrity of any number of electronic components of the medicament delivery device can be tested by the self-test. For example, the integrity of the LEDs and/or audio output device can be tested using a similar self-test as the one described above.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, in some embodiments, the sidewall of the housing of a medicament delivery device can be rigid. In other embodiments, the sidewall can be a movable member such as, for example, a piston. In yet other embodiments, the sidewall can be a flexible member such as, for example, a diaphragm. In some embodiments, the sidewall can be transparent allowing light to pass from the a first region to a second region and vice versa. A transparent sidewall can be used in conjunction with an optical sensor. The sidewall can be integrally formed with the housing or can be separately formed.

In other embodiments, the medicament container can be substantially cylindrical with a substantially round and/or substantially elliptical cross-sectional shape. Thus, the medicament container can define a longitudinal axis, the longitudinal axes of the medicament container can be parallel, non-coaxial, and/or co-planar. The longitudinal axis of the medicament container can be co-axial with a longitudinal axis of the piston portion of a movable member 4530. In still other embodiments, a medicament delivery device can contain multiple medicament containers and thus, multiple doses of medicament.

Although medical devices having two LEDs and an audio output device have been shown, in other embodiments the medical device might have any number of LEDs and/or audio output devices. Additionally, other types of output devices, such as haptic output devices, can be used.

Although various embodiments have been described as having particular features and/or combinations of components, other embodiments are possible having a combination of any features and/or components from any of embodiments where appropriate. For example, electrical circuit system 4900 can include a electronic circuit system configuration switch similar to that of electrical circuit system 5900.

What is claimed is:

1. An apparatus comprising:
a simulated medicament injector configured to simulate an operation of an actual medicament injector, the simulated medicament injector being devoid of at least one of a medicament or a needle, the simulated medicament injector including:
a housing defining an opening;
an electronic circuit system coupled to the housing, the electronic circuit system including a battery, a processor, a start button and a speaker, the electronic circuit system configured to produce a recorded speech output associated with an operation of the simulated medicament injector when the start button is manipulated; and
a battery isolation member moveable between a first position and a second position, a first portion of the battery isolation member disposed through the opening and within the housing to electrically decouple the battery from the processor when the battery isolation member is in the first position, a second portion of the battery isolation member disposed outside the housing when the battery isolation member is in the first position, the first portion of the battery isolation member disposed outside the housing when the battery isolation member is in the second position such that the battery is electrically coupled to the processor.

2. The apparatus of claim 1, wherein:
the housing defines a status aperture; and
the simulated medicament injector includes a status indicator visible through the status aperture, the status indicator configured to display a visual indicia to simulate a status indicator of the actual medicament injector.

3. The apparatus of claim 1, wherein:
the housing defines a status aperture; and
the simulated medicament injector includes a status indicator visible through the status aperture, the status indicator configured to allow a user to determine the activation status of the simulated medicament injector, the status indicator is configured to display a first color visible when the status indicator is in a first configuration and a second color when the status indicator is in a second configuration.

4. The apparatus of claim 1, wherein the electronic circuit system is configured to produce the recorded speech output in a plurality of languages.

5. The apparatus of claim 1, wherein any one of a shape, a size or a weight of the simulated medicament injector corresponds with any one of a shape, a size or a weight of the actual medicament injector.

6. The apparatus of claim 1, wherein the simulated medicament injector includes:
a simulated needle cap removeably coupled to the housing, a portion of the simulated needle cap configured to be disposed within the housing when the simulated needle cap is coupled to the housing.

7. An apparatus comprising:
a simulated medicament injector configured to simulate an operation of an actual medicament injector, the simulated medicament injector being devoid of at least one of a medicament or a needle, the simulated medicament injector including:
a housing defining a first opening and a second opening;
an electronic circuit system coupled to the housing, the electronic circuit system including a speaker at least partially disposed within the first opening; and
a battery isolation member having a portion configured to be disposed through the second opening and within the housing when the battery isolation member is in a first position, the portion disposed outside of the housing when the battery isolation member is in a second position, the electronic circuit system configured to produce a recorded speech output when the battery isolation member is in the second position and the electronic circuit system is actuated.

8. The apparatus of claim 7, wherein the housing defines a status aperture, the simulated medicament injector includes:
a visual output assembly disposed within the housing, the visual output assembly configured to allow a user to determine an activation status of the simulated medicament injector.

9. The apparatus of claim 7, wherein the housing defines a status aperture, the simulated medicament injector includes:
a visual output assembly disposed within the housing the visual output assembly associated with simulated injection of the medicament.

10. The apparatus of claim 7, wherein:
the recorded speech output is a first recorded speech output; and
the electronic circuit system is configured to produce a second recorded speech output at a predetermined time period after the first recorded speech output.

11. The apparatus of claim 7, wherein the electronic circuit system includes a flexible printed circuit.

12. The apparatus of claim 7, wherein the simulated medicament injector includes:
a system actuator configured to actuate the simulated medicament injector, the simulated medicament injector configured to produce an audible output that simulates the actuation of the actual medicament injector when the system actuator is manipulated.

13. The apparatus of claim 7, wherein the simulated medicament injector includes a simulated delivery mechanism including:
a rod, an end portion of the rod including two projections;
a spring;
a spring retainer configured to engage the two projections to maintain the rod in a fixed position; and
a system actuator configured to actuate the simulated medicament injector to simulate an operation of the actual medicament injector, the system actuator configured to move the two projections inwardly to decouple the rod from the spring retainer.

14. An apparatus comprising:
a simulated medicament injector configured to simulate an operation of an actual medicament injector, the simulated medicament injector being devoid of at least one of a medicament or a needle, the simulated medicament injector including:
a housing defining a first aperture and a second aperture;
an electronic circuit system coupled to the housing, the electronic circuit system including a printed circuit board, a battery, and a speaker, the electronic circuit system configured to produce a recorded speech output associated with an operation of the simulated medicament injector;
a battery isolation member, a portion of the battery isolation member configured to be removeably disposed through the first aperture, the battery isolation member configured to disable the electronic circuit system when the portion of the battery isolation member is disposed through the first aperture, the electronic circuit system being enabled to produce the recorded speech output when the portion of the battery isolation member is removed via the first aperture; and a simulated needle cap, a protrusion of the simulated needle cap configured to be removeably disposed through the second aperture.

15. The apparatus of claim 14, wherein the simulated needle cap is configured to be removed from the housing to simulate the operation of the actual medicament injector.

16. The apparatus of claim 14, wherein the simulated needle cap includes an indication indicating a direction for removing the simulated needle cap from the housing.

17. The apparatus of claim 14, wherein the simulated medicament injector is configured to repeatedly simulate the delivery of the actual medicament injector.

18. The apparatus of claim 14, wherein the simulated medicament injector includes a status indicator configured to allow a user to determine the activation status of the simulated medicament injector, the status indicator is configured to display a first color visible when the status indicator is in a first configuration and a second color when the status indicator is in a second configuration.

19. The apparatus of claim 1, wherein:
the housing is a first housing, the first housing defines a cavity; and
the speaker is coupled to a second housing, the second housing configured to be coupled to the first housing such that the second housing covers the cavity.

20. The apparatus of claim 1, wherein:
the housing is a first housing; and
the speaker is coupled to a second housing, the second housing configured to be coupled to the first housing.

21. The apparatus of claim 20, wherein the second housing includes a protrusion configured to matingly engage a connection aperture defined by the first housing.

22. The apparatus of claim 1, wherein the electronic circuit system includes a biased electrical contact member, the first portion of the battery isolation member configured to maintain the biased electrical contact member in a first contact configuration when the battery isolation member is in the first position, the biased electrical contact member configured to transition to a second contact configuration when the battery isolation member is in the second position.

23. The apparatus of claim 7, wherein the electronic circuit system includes a battery, a processor and a biased electrical contact member, the first portion of the battery isolation member configured to maintain the biased electrical contact member in a first contact configuration when the battery isolation member is in the first position such that battery is electrically isolated from the processor, the biased electrical contact member configured to transition to a second contact configuration to electrically couple the battery to the processor when the battery isolation member is in the second position.

24. The apparatus of claim 7, wherein:
the housing is a first housing; and
the speaker is coupled to a second housing, the second housing configured to be coupled to the first housing to maintain the speaker at least partially within the first opening.

25. The apparatus of claim 24, wherein the second housing includes a protrusion configured to matingly engage a connection aperture defined by the first housing.

26. The apparatus of claim 14, wherein electronic circuit system includes a biased electrical contact member, the first portion of the battery isolation member configured to maintain the biased electrical contact member in a first contact configuration when the battery isolation member is in the first position, the biased electrical contact member configured to transition to a second contact configuration when the battery isolation member is in the second position.

27. The apparatus of claim 14, wherein:
the housing is a first housing; and
the speaker is coupled to a second housing, the second housing configured to be coupled to the first housing to maintain the speaker within a cavity defined by the first housing.

28. The apparatus of claim 27, wherein the second housing includes a protrusion configured to matingly engage a connection aperture defined by the first housing.

* * * * *